(12) United States Patent
Joncyk et al.

(10) Patent No.: US 8,586,545 B2
(45) Date of Patent: Nov. 19, 2013

(54) SOLID MATERIALS OF {[(2S, 5R,8S,11S)-5-BENZYL-11-(3-GUANIDINO-PROPYL)-8-ISOPROPYL-7-METHYL-3,6,9,12,15-PENTAOXO-1,4,7,10,13-PENTAAZA-CYCLOPENTADEC-2-YL]-ACID} AND METHODS FOR OBTAINING THEM

(75) Inventors: Alfred Joncyk, Darmstadt (DE);
Clemens Kuehn, Darmstadt (DE);
Kerstin Seemann, Darmstadt (DE);
Christoph Saal, Otzberg (DE); Gerald Scholz, Bensheim (DE); Soenke Petersen, Darmstadt (DE); Harald Untenecker, Solms (DE); Michael Lange, Hochkirch (DE)

(73) Assignee: Merck Patent GmbH, Darmstadt (DE)

(*) Notice: Subject to any disclaimer, the term of this patent is extended or adjusted under 35 U.S.C. 154(b) by 0 days.

(21) Appl. No.: 13/321,001

(22) PCT Filed: May 20, 2010

(86) PCT No.: PCT/EP2010/003100
§ 371 (c)(1),
(2), (4) Date: Nov. 17, 2011

(87) PCT Pub. No.: WO2010/133367
PCT Pub. Date: Nov. 25, 2010

(65) Prior Publication Data
US 2012/0065142 A1  Mar. 15, 2012

(30) Foreign Application Priority Data

May 20, 2009 (EP) .................................. 09006790

(51) Int. Cl.
*A61P 35/00* (2006.01)
*A61K 38/12* (2006.01)

(52) U.S. Cl.
USPC ........... 514/19.3; 530/317; 530/321; 530/344

(58) Field of Classification Search
None
See application file for complete search history.

(56) References Cited

U.S. PATENT DOCUMENTS 6,001,961 A  12/1999  Jonczyk et al.
6,822,074 B1 * 11/2004  Jonczyk et al. ............... 530/330

FOREIGN PATENT DOCUMENTS

| EP | 0770622 | 8/1996 |
| WO | WO 98/57648 | 12/1998 |
| WO | WO 00/53627 | 9/2000 |
| WO | WO 2011/069629 | 6/2011 |

OTHER PUBLICATIONS

Creighton et al., Bioorganic & Medicinal Chemistry Letters 16: 3971-3974 (2006).

* cited by examiner

Primary Examiner — Nashaat Nashed
(74) Attorney, Agent, or Firm — Perkins Coie LLP

(57) ABSTRACT

The instant invention relates to novel solid materials of {[(2S, 5R,8S,11S)-5-Benzyl-11-(3-guanidino-propyl)-8-isopropyl-7-methyl-3,6,9,12,15-pentaoxo-1,4,7,10,13-pentaaza-cyclopentadec-2-yl]-acetic acid}, methods for producing them, and the use of said solid materials in pharmaceuticals.

15 Claims, 41 Drawing Sheets

Single crystal structure of form A1

DSC scan of form A1 (Mettler-Toledo DSC 821, 5 K/min, nitrogen purge gas 50 ml/min)

Single crystal structure of form A1

DSC scan of form S1 (Mettler-Toledo DSC 821, 5 K/min, nitrogen purge gas 50 ml/min)

Powder X-ray diffractogram of crystalline form S1

FTIR spectrum of form S1

FT Raman spectrum of form S1

Water Vapour Sorption Isotherm (25 °C) of form S2
(SMS DVS Intrinsic)

Powder X-ray diffractogram of crystalline form S3

Single crystal structure of form S3

Zig-zag chain formation of the Cilengitide molecules in the lattice of form S3

Crystal structure with the voids (green) between the API molecules of Cilengitide, form S3

Structure of voids in crystal lattice of Cilengitide, form S3

FTIR spectrum of form S3

Stoichiometries of samples obtained from conditioning experiments of amorphous material or hydrate forms of compound according to formula I under mixed water-ethanol atmospheres. x-axes = number of molecules water per molecule of formula I; y-axes = number of molecules ethanol per molecule of formula I.

Figure 31
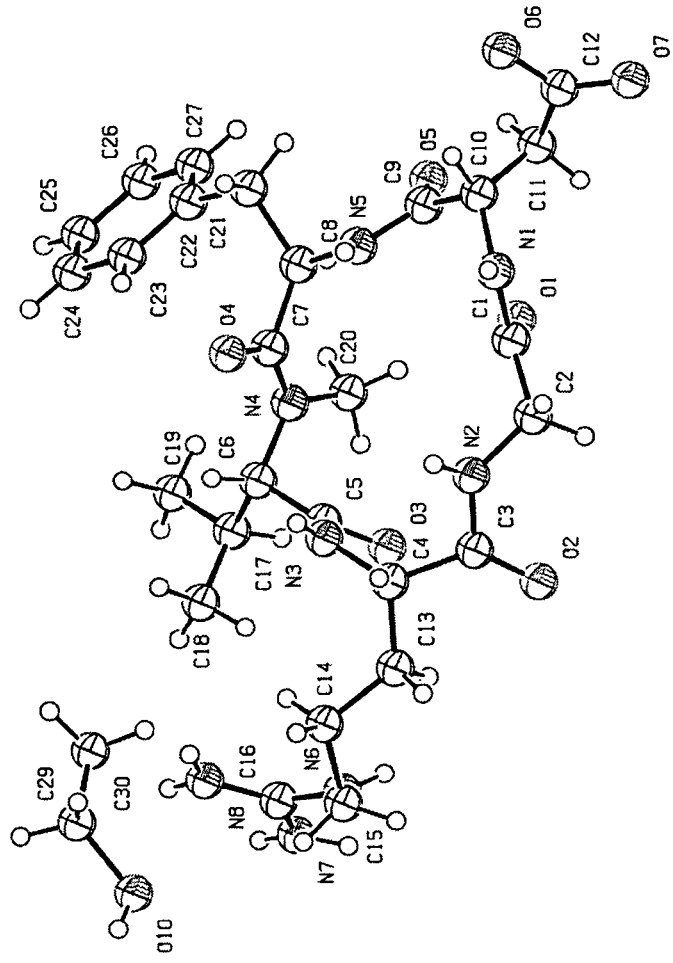
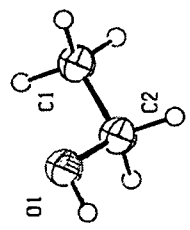
Powder pattern structure solution of form S2 – di-ethanol solvate or diethanolate Single crystal structure solution of form S2 – mono-ethanol solvate dihydrate Single crystal structure solution of form H1 - heptahydrate

SOLID MATERIALS OF {[(2S, 5R,8S,11S)-5-BENZYL-11-(3-GUANIDINO-PROPYL)-8-ISOPROPYL-7-METHYL-3,6,9,12,15-PENTAOXO-1,4,7,10,13-PENTAAZA-CYCLOPENTADEC-2-YL]-ACID} AND METHODS FOR OBTAINING THEM

This application is a 371 of PCT/EP2010/003100 filed May 20, 2010, which claims priority to European App. No. 09006790.1 filed May 20, 2009. The entire contents of the above-identified applications are hereby incorporated by reference.

The instant invention relates to novel solid materials of {[(2S,5R,8S,11S)-5-Benzyl-11-(3-guanidino-propyl)-8-isopropyl-7-methyl-3,6,9,12,15-pentaoxo-1,4,7,10,13-pentaaza-cyclopentadec-2-yl]-acetic acid}, methods for producing them, and the use of said solid materials in pharmaceuticals.

{[(2S,5R,8S,11S)-5-Benzyl-11-(3-guanidino-propyl)-8-isopropyl-7-methyl-3,6,9,12,15-pentaoxo-1,4,7,10,13-pentaaza-cyclopentadec-2-yl]-acetic acid} or cyclo-(Arg-Gly-Asp-DPhe-NMe-Val) was first described in the patents/patent applications U.S. Pat. No. 6,001,961 and EP 0 770 622, which were first published in 1997. In said patents, various salt forms of said compound were described, e.g. the hydrochloride, the acetate and the methansulfonate. Later, an improved method of manufacture that led to the inner salt of cyclo-(Arg-Gly-Asp-DPhe-NMe-Val) was described in WO 00/53627. However, the solids obtained according to the described procedures appeared to be amorphous material.

Pharmaceutical activity is of course the basic prerequisite to be fulfilled by a pharmaceutically active agent, pharmaceutically active principle or active pharmaceutical ingredient (API) before same is approved as a medicament on the market. However, there are a variety of additional requirements a pharmaceutically active agent has to comply with. These requirements are based on various parameters which are connected with the nature of the active substance itself. Without being restrictive, examples of these parameters are the stability of the active agent or active ingredient under various environmental conditions, its stability during production of the pharmaceutical formulation and the stability of the active agent or active ingredient in the final medicament compositions. The pharmaceutically active substance used for preparing the pharmaceutical compositions should be as pure as possible and its stability in long-term storage must be guaranteed under various environmental conditions. This is absolutely essential to prevent the use of pharmaceutical compositions which contain, in addition to the actual active substance, breakdown or decomposition products thereof, for example. In such cases the content of active substance in the medicament might be less than that specified and/or the medicament might fail quality control.

Technical factors like the particle size or uniform distribution of the active principle or active ingredient in the formulation can be critical factor, particularly when the medicament is a complex formulation and/or the medicament has to be given in low doses. To enable complex formulation systems and/or to ensure uniform distribution, the particle size of the active substance can be adjusted to a suitable level, e.g. by grinding. Since breakdown of the pharmaceutically active substance as a side effect of processing steps, such as purification, dissolution, melting, grinding, micronising, mixing and/or extruding has to be minimized, despite the harsh conditions required during said processing steps, it is absolutely essential that the active substance is highly stable throughout said processing steps. Only if the active substance is sufficiently stable during the processing steps, it is possible to produce a homogeneous pharmaceutical formulation which always fulfils the quality requirements and contains the specified amount of active substance in reproducible manner.

Another problem which may arise in the grinding process for preparing the desired pharmaceutical formulation is the input of energy and/or pressure caused by the process steps, such as the stress on the surface of the particles of the API, no matter whether it is amorphous or crystalline. This may in certain circumstances lead to polymorphic changes, to a change in the amorphous configuration or to a change in the crystal lattice, depending on the solid material or form employed in the processing steps. Since the pharmaceutical quality of a pharmaceutical formulation requires that the active substance should always have the same morphology, preferably the same crystalline morphology, the stability and properties of the solid API are subject to stringent requirements from this point of view as well. Thus, the stability and also a long shelf life of the API itself is of real importance.

Many pharmaceutical solids can exist in different physical forms. Polymorphism is preferably characterized as the ability of a compound, such as a drug substance, to exist in two or more crystalline modifications that have different arrangements and/or conformations of the molecules in the crystal lattice (D. J. W. Grant. Theory and origin of polymorphism. In H. G. Brittain (ed.) Polymorphism in Pharmaceutical Solids. Marcel Dekker, Inc., New York, 1999, pp. 1-34, the disclosure of which is incorporated into this application by reference in its entirety). Amorphous solids consist of disordered arrangements of molecules and do not possess a crystal lattice and/or a long range order. Solvates are crystalline solids containing either stoichiometric or non-stoichiometric amounts of a solvent incorporated within the crystal structure. If the incorporated solvent is water, the solvates are also commonly known as hydrates. Polymorphism refers to the occurrence of different crystalline modifications of the same compound or drug substance. Polymorphism in this commentary is defined as in the International Conference on Harmonization (ICH) Guideline Q6A (International Conference on Harmonization Q6A Guideline: Specifications for New Drug Substances and Products: Chemical Substances, October 1999, the disclosure of which is incorporated into this application by reference in its entirety), to include solvates and amorphous forms.

Stoichiometric solvates are preferably regarded as molecular compounds. The term preferably implies a fixed, although not necessarily integral, ratio of solvent to compound. Non-stoichiometric solvates preferably are a type of inclusion compound. The most important feature of this class of solvates is that the structure is retained, while the solvent content can potentially take on all values between possibly zero and a multiple of the molar compound ratio. The amount of solvent in the structure depends on the partial pressure of the solvent in the environment of the solid and the temperature (see: U. J. Griesser, "The Importance of Solvates" in R. Hilfiker (Editor) "Polymorphism in the Pharmaceutical Industry", Wiley VCH, 2006, the disclosure of which is incorporated into this application in its entirety).

Polymorphs and/or solvates of a pharmaceutical solid can have different chemical and physical properties such as melting point, hygroscopicity, chemical reactivity, apparent solubility, dissolution rate, optical and electrical properties, vapor pressure and/or density. These properties can have a direct impact on the processability of drug substances and the quality/performance of drug products, such as stability, dissolution and/or bioavailability. A metastable pharmaceutical solid state form can change crystalline structure or solvate/desolvate in response to changes in environmental conditions, processing, or over time.

The stability of an API is also important in pharmaceutical compositions for determining the shelf life of the particular medicament; the shelf life is the time period during which a drug product is expected to remain within the approved specification, provided that it is stored under the defined conditions. Within the defined shelf life, a medicament can be administered without any risk for the patient. High stability of a medicament in the abovementioned pharmaceutical compositions under various storage conditions is therefore an additional advantage for both the patient and the manufacturer.

Apart from the requirements indicated above, it should be generally borne in mind that any change of the solid state form of a pharmaceutical composition which is capable of improving its physical and chemical stability gives a significant advantage over less stable forms of the same medicament. The aim of the invention is thus to provide a new, stable solid material of the compound cyclo-(Arg-Gly-Asp-DPhe-NMe-Val) which meets the stringent requirements imposed on pharmaceutically active substances as mentioned above. Thus, one goal of the present invention is the provision of novel solid materials or forms of cyclo-(Arg-Gly-Asp-DPhe-NMe-Val) with improved solid-state properties.

BRIEF DESCRIPTION OF THE DRAWINGS

FIG. 31 depicts the powder pattern structure solution of crystalline form S2.

Figure 1:
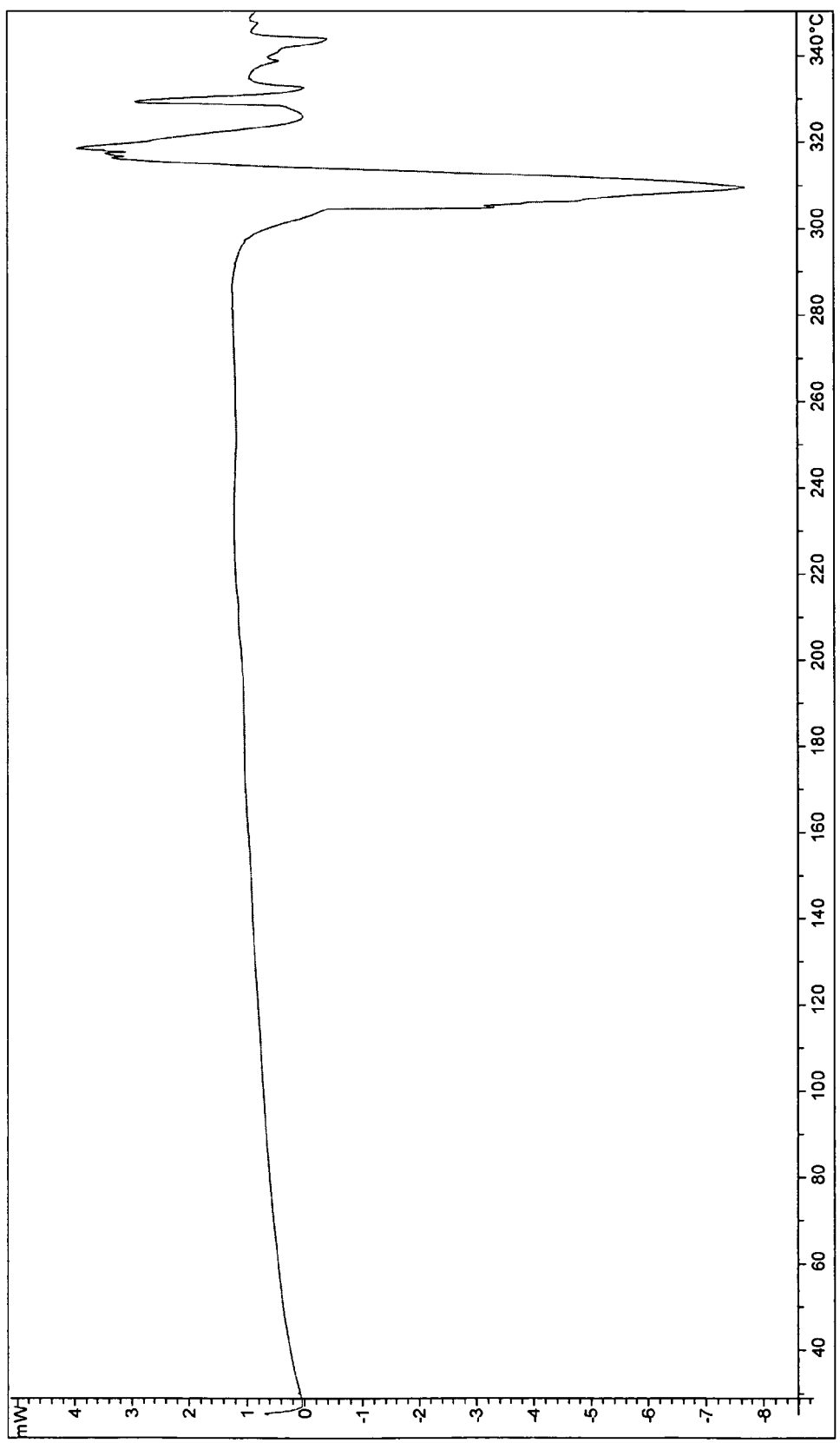
FIG. 1 depicts the DSC measurements of crystalline form A1.

It was now found that cyclo-(Arg-Gly-Asp-DPhe-NMe-Val) and especially the inner salt thereof can be obtained as a crystalline material and also in special crystalline forms. Surprisingly a whole class of novel crystalline forms of similar structural types (further on also to be named pseudopolymorphic forms, PP) of cyclo-(Arg-Gly-Asp-DPhe-NMe-Val) have been found, which in fact exhibit beneficial solid state properties and preferably also possess advantageous combinations of beneficial solid state properties, e.g. combined beneficial properties of the known material with beneficial properties of the new material according to the invention.

Additionally, it was surprisingly found that different methods for obtaining the novel crystalline material preferably lead to different crystalline forms or modifications within said class of crystalline forms. These crystalline forms or modifications of the compound cyclo-(Arg-Gly-Asp-DPhe-NMe-Val) and especially the inner salt thereof and the methods of making them are preferred the subject of the instant application.

Said novel solid material and said crystalline forms or modifications show valuable properties and advantages in comparison to the amorphous materials previously known, including, but not limited to a higher thermodynamic stability, reduced hygroscopicity, a higher crystallinity, improved handling properties, advantageous dissolution properties and/or an improved storage stability.

The compound {[(2S,5R,8S,11S)-5-Benzyl-11-(3-guanidino-propyl)-8-isopropyl-7-methyl-3,6,9,12,15-pentaoxo-1,4,7,10,13-pentaaza-cyclopentadec-2-yl]-acetic acid} or cyclo-(Arg-Gly-Asp-DPhe-NMe-Val), also known under the INN (International Non-proprietary Name) Cilengitide, shows an advantageous biological activity, including, but not limited to its integrin inhibitory activity, anti-angiogenic activity and radiotherapy enhancing activity, it is widely employed as an active principle in pharmaceutical applications.

For use as an active principle in pharmaceutical applications or short for use as API, factors such as high purity, excellent handling properties, sufficient stability and reliable manufacturing processes are crucial. Additionally, for such a peptidic compound having both basic and acidic centres or moieties, an exact stoichiometry in salt formation is another crucial factor and therefore a task for the production of the API. Acidic salts of cyclo-(Arg-Gly-Asp-DPhe-NMe-Val) have been found to be easily produced, but found to be less stable due to acid catalysed degradation. Basic salts generally have been found to possess undesirable dissolution and handling properties. The previously known and described amorphous forms of cyclo-(Arg-Gly-Asp-DPhe-NMe-Val) have been found to be unfavourably hygroscopic, one major drawback in the production of dosage forms and also in the development of suitable pharmaceutical formulations.

Thus, a solid form with improved stability, improved handling, higher purity and/or higher purification rate of the API, in comparison to the known amorphous form, is generally highly desirous and a real need for a reliable technical large-scale manufacture of the API. This is even more so if a solid dosage formulation or suspension formulation of the API has to be provided.

Thus, subjects of the instant invention are:

A solid material of a compound according to formula I, $$\text{cyclo-(Arg-Gly-Asp-DPhe-NMeVal)} \quad (I)$$

wherein said solid material comprises one or more crystalline forms of the compound of formula I, characterised by a unit cell with the lattice parameters $$a=9.5\pm0.5 \text{ Å},$$

$$b=23.0\pm5.0 \text{ Å},$$

and $$c=14.7\pm1.0 \text{ Å}.$$

Said unit cell is preferably a crystallographic unit cell or a crystallographically determined unit cell.

In said unit cell, the angle $\alpha$ preferably is $90°\pm2°$, the angle $\beta$ preferably is $90°\pm2°$ and/or the angle $\gamma$ preferably is $90°\pm2°$.

Preferably, the solid material comprises at least 10% by weight, more preferably at least 30% by weight, even more preferably 60% by weight and especially at least 90% by weight or at least 95% by weight, of one or more crystalline forms of the compound of formula I as defined above and/or below. For example, the solid material comprises about 25, about 50, about 75, about 95, about 99 or about 100% by weight of one or more crystalline forms of the compound of formula I as defined above and/or below.

Especially preferably, the solid material comprises at least 10 mole %, more preferably at least 30 mole %, even more preferably 60 mole % and especially at least 90 mole % or at least 95 mole %, of one or more crystalline forms of the compound of formula I as defined above and/or below. For example, the solid material comprises about 25, about 50, about 75, about 95, about 99 or about 100 mole % of one or more crystalline forms of the compound of formula I as defined above and/or below.

The percentages by weight given for the solid material according to the invention preferably relate to the ratio between the weight of the one or more crystalline forms as defined above/below contained in said solid material and the total amount by weight of the compound of formula I contained in said solid material. In other words, the percentages by weight given preferably are the weight percentages of the sum of the one or more crystalline forms as defined above and/or below based on the total amount by weight of the compound of formula I. Thus, the weight percentages given for the content of the one or more crystalline forms with in the solid material according to the invention are preferably independent of the amount or content of compounds or impurities other than the compound according to formula I contained in said solid material. Thus, the percentages by weight given for the solid material are preferably corrected for the contained solvent molecules, i.e. the percentages by weight given for the solid material are preferably independent of or calculated without the solvent molecules in said solid material.

The mole percentages (mole %) given for the solid material according to the invention preferably relate to the molar ratio between the one or more crystalline forms as defined above/below contained in said solid material and the total molar amount of the compound of formula I contained in said solid material. In other words, the mole percentages given preferably are the mole percentages of the sum of the one or more crystalline forms as defined above and/or below based on the total molar amount of the compound of formula I. Thus, the mole percentages given for the content of the one or more crystalline forms with in the solid material according to the invention are preferably independent of the amount or content of compounds or impurities other than the compound according to formula I contained in said solid material. Thus, the mole percentages (mole %) given for the solid material are preferably corrected for the contained solvent molecules, i.e. the mole percentages (mole %) given for the solid material are preferably independent of or calculated without the solvent molecules in said solid material.

One or more crystalline forms in regard to said solid material preferably means that the solid material comprises at least one or more crystalline form or modification of the compound of formula I having a unit cell within the lattice parameters as defined above and/or below, or that the solid material comprises mixtures of two or more, for example two or three, crystalline forms or modifications of the compound of formula I, each having a unit cell within the lattice parameters as defined above and/or below.

Preferably, the solid material comprises one, two, three or four crystalline forms of the compound of formula I as defined above and/or below.

More preferably, the solid material comprises one or more, preferably one, two, three or four, even more preferably one or two, crystalline forms of the compound of formula I, each having a unit cell with lattice parameters (ULP) selected from a group consisting of

ULP1:

$$a1=9.5\pm0.5 \text{ Å},$$

$$b1=26.0\pm1.5 \text{ Å},$$

and $$c1=14.3\pm0.7 \text{ Å},$$

and

ULP2:

$$a2=9.8\pm0.5 \text{ Å},$$

$$b2=20.0\pm1.5 \text{ Å},$$

and $$c2=15.4\pm0.7 \text{ Å}.$$

More preferably, the solid material comprises one or more, preferably one, two, three or four, even more preferably one or two, crystalline forms of the compound of formula I, each having a unit cell with lattice parameters (ULP) selected from a group consisting of
ULP1:

$a1=9.5\pm0.3$ Å, $b1=26.0\pm1.0$ Å, and $c1=14.3\pm0.5$ Å, and
ULP2:

$a2=9.8\pm0.3$ Å, $b2=20.0\pm1.0$ Å, and $c2=15.4\pm0.5$ Å.

In the unit cell with lattice parameters ULP1 and/or ULP2, the angle $\alpha$ preferably is $90°\pm2°$, the angle $\beta$ preferably is $90°\pm2°$ and/or the angle $\gamma$ preferably is $90°\pm2°$.

Preferably, the unit cell with lattice parameters ULP1 can be characterised, alternatively or additionally, preferably additionally, by a content of about 4 molecules of the compound of formula I within said unit cell.

In the unit cell with lattice parameters ULP2, the angle $\alpha$ preferably is $90°\pm0.5°$, the angle $\beta$ preferably is $90°\pm0.5°$ and/or the angle $\gamma$ preferably is $90°\pm0.5°$. In the unit cell with lattice parameters ULP2, the angles $\alpha$, $\beta$ and $\gamma$ more preferably are $90°\pm0.1°$.

Preferably, the unit cell with lattice parameters ULP2 can be characterised, alternatively or additionally, preferably additionally, by a content of about 4 molecules of the compound of formula I within said unit cell.

More preferably, the solid material comprises one or more, preferably one, two, three or four, even more preferably one or two, crystalline forms of the compound of formula I, selected from
crystalline form A1, characterised by a unit cell with the lattice parameters $a=9.8\pm0.1$ Å, $b=19.5\pm0.5$ Å, and $c=15.4\pm0.1$ Å,
crystalline form S1, characterised by a unit cell with the lattice parameters $a=9.4\pm0.1$ Å, $b=25.9\pm0.5$ Å, and $c=14.1\pm0.1$ Å,
crystalline form S2, characterised by a unit cell with the lattice parameters $a=9.3\pm0.1$ Å, $b=26.6\pm0.5$ Å, and $c=14.7\pm0.1$ Å, and
crystalline form S3, characterised by a unit cell with the lattice parameters $a=9.6\pm0.1$ Å, $b=25.9\pm0.5$ Å, and $c=13.9\pm0.1$ Å.

More preferably, the solid material comprises one or more, preferably one, two, three or four, even more preferably one or two, crystalline forms of the compound of formula I, selected from
crystalline form A1, characterised by a unit cell with the lattice parameters $a=9.8\pm0.1$ Å, $b=19.5\pm0.5$ Å, and $c=15.4\pm0.1$ Å, preferably with $\alpha=\beta=\gamma=90°\pm1°$ and especially with $\alpha=\beta=\gamma=90°$;
crystalline form S1, characterised by a unit cell with the lattice parameters $a=9.4+0.1$ Å, $b=25.9\pm0.5$ Å, and $c=14.1\pm0.1$ Å, preferably with $\alpha=\beta=\gamma=90°\pm2°$, and especially with $\alpha=90°\pm1°$, $\beta=91°\pm1$, $\gamma=90°\pm1°$ and especially with $\alpha=90°$, $\beta=91.2°$, $\gamma=90°$;
crystalline form S2, characterised by a unit cell with the lattice parameters $a=9.3\pm0.1$ Å, $b=26.6\pm0.5$ Å, and $c=14.7\pm0.1$ Å, preferably with $\alpha=\beta=\gamma=90°\pm1°$ and especially with $\alpha=\beta=\gamma=90°$; and
crystalline form S3, characterised by a unit cell with the lattice parameters $a=9.6\pm0.1$ Å, $b=25.9\pm0.5$ Å, and $c=13.9\pm0.1$ Å, preferably with $\alpha=\beta=\gamma=90°\pm1°$ and especially with $\alpha=\beta=\gamma=90°$.

Preferably, the crystalline forms S1, S2 and S3 can be characterised, alternatively or additionally, preferably additionally, by a content of about 4 molecules of the compound of formula I within said unit cells.

The crystalline forms S1, S2 and S3 are preferably further characterised as solvates.

In the context of the present invention, solvates preferably are crystalline solid adducts containing either stoichiometric or non-stoichiometric amounts of a solvent incorporated within the crystal structure, i.e. the solvent molecules preferably form a part of the crystal structure. If the incorporated solvent is water, the solvates are also commonly known as hydrates.

As a result, the solvent in the solvates preferably forms a part of the crystal structure and thus is in general detectable by X-ray methods and preferably detectable by X-ray methods as described herein.

In general, for a given crystal structure, there is an upper limit for the amount of solvent incorporated into said structure (without inducing a transition into another crystal structure). In some cases, however, it is possible to remove at least a part of the incorporated solvent by physical treatment of the crystal structure, for example by drying procedures, e.g. by storage at elevated temperatures (but preferably below a melting or other phase transition point), and/or reduced pressure, preferably including applying vacuum and reduced partial pressure. In principal in such cases, the solvent can be partly or fully removed from the crystal structure, thus introducing voids into said crystal structure. The likelihood of a phase transition and/or polymorphic transition, e.g. the transition into a different polymorphic form or especially the transition into an amorphous form, a solvate or hydrate containing less solvent or water molecules or an anhydrate form, increases with the amount of incorporated solvent converging to zero.

In such cases, the solvent contained and/or the amount thereof and thus the composition of the respective solvates or solvate structure can preferably be varied by adequate treatment, including, but not limited to conditioning and/or recrystallisation. For example, one solvent can be partly or fully removed from such a solvate, one solvent can be partly or fully substituted by a different solvent in such a solvate and/or the amount of solvent in such a solvate can be increased or decreased. Thus, a solvate containing a specific solvent can potentially be transformed into a solvate containing a solvate mixture, and vice versa.

Conditioning in this regard preferably relates to physical treatments, wherein the original crystal structure of the respective solvate is essentially retained. Suitable methods, and means and/or parameters for conditioning of solvates are in principle known to the skilled artisan. Examples of suitable conditioning methods are disclosed in the instant application and preferably include, but are not limited to, exposure to solvent vapour, exposure to thermal conditions (for example by differential scanning calorimetry, thermogravimetry and/or storage at specific temperatures or temperature gradients), slurrying (e.g. forming and/or treating a suspension of a solvate in a liquid that comprises or one or more solvents), exposure to variable partial pressure of one or more solvents, exposure to specific partial pressure and/or specific partial pressure gradients of one or more solvents, and combinations thereof. For example the slurrying and/or the exposure to variable partial pressure of one or more solvents can be realised at specific temperatures or temperature gradients. A preferred form of conditioning is solvating or desolvating. Slurries and working techniques for slurries or slurrying are known in the art, for example from Martyn D. Ticehurst,* Richard A. Storey, Claire Watt, International Journal of Pharmaceutics 247 (2002) 1-10, the disclosure of which is incorporated into this application in its entirety.

Additionally or alternatively, the solvent contained and/or the amount thereof and thus the composition of the respective solvates or solvate structure can preferably be also varied by recrystallisation, especially by recrystallisation from a different solvent or solvent mixture, provided the original crystal structure of the solvate is reproduced or essentially reproduced.

In this regard, solvate preferably means that the unit cell or crystallographic unit cell contains an about stoichiometric—integer or non integer—amount of solvent molecules of one or more solvents per molecule of the compound of formula I contained in said unit cell. The about stoichiometric amount of solvent molecules in said unit cell per molecule of the compound of formula I contained in said unit cell preferably lies in the range of about 0.01 solvent molecules to about 8 solvent molecules, more preferably in the range of about 0.1 solvent molecules to about 7 solvent molecules and even more preferably in a range of about 1.5 solvent molecules up to about 4.5 solvent molecules, for example about 0.1 solvent molecules, about 0.5 solvent molecules, about 1.5 solvent molecules, about 3 solvent molecules, about 4 solvent molecules or about 7 solvent molecules per molecule of the compound according to formula I. Especially preferred are solvates having about four solvent molecules per molecule of the compound according to formula I contained in said unit cell. If the unit cell or crystallographic unit cell contains about 4 solvent molecules of one or more solvents per molecule of the compound of formula I contained in said unit cell, it is preferably regarded as a tetrasolvate, and if it contains about 7 solvent molecules of one or more solvents per molecule of the compound of formula I contained in said unit cell, it is preferably regarded as a heptasolvate.

In this regard, solvate preferably means that the unit cell or crystallographic unit cell contains an about stoichiometric, preferably integer or non-integer, more preferably about integer, amount of solvent molecules of one or more solvents per molecule of the compound of formula I contained in said unit cell. The about stoichiometric amount of solvent molecules in said unit cell per molecule of the compound of formula I contained in said unit cell preferably lies in the range of about 0.5 solvent molecules to about 6 solvent molecules, more preferably in the range of about 0.5 solvent molecules to about 4.5 solvent molecules and even more preferably in a range of about 1.5 solvent molecules up to about 4 solvent molecules per molecule of the compound according to formula I contained in said unit cell, for example about 0.5 solvent molecules, about 1.5 solvent molecules, about 4 solvent molecules or about 6 solvent molecules per molecule of the compound according to formula I contained in said unit cell. Especially preferred are solvates having about four solvent molecules per molecule of the compound according to formula I contained in said unit cell. If the unit cell or crystallographic unit cell contains about 4 solvent molecules of one or more solvents per molecule of the compound of formula I contained in said unit cell, it is preferably regarded as a tetrasolvate.

Preferred solvents or solvent molecules in this regard are selected from the group consisting of water and alcohols, and more preferably selected from the group consisting of water, methanol and ethanol.

For example, if the unit cell of a crystalline form contains one molecule of the compound according to the formula I and about four solvent molecules, said form is preferably to be regarded as a tetrasolvate. If the unit cell of a crystalline form contains two molecules of the compound of formula I and about eight solvent molecules, said form is preferably also to be regarded as a tetrasolvate. If the unit cell of a crystalline form contains four molecules of the compound of formula I and about sixteen solvent molecules, said form is preferably also to be regarded as a tetrasolvate. The same holds true, if the unit cell of a crystalline form contains 2½ molecules of the compound according to a formula I and about 10 solvent molecules.

Thus, solvate more preferably means that the respective crystalline form contains an about stoichiometric—integer or non-integer—amount of solvent molecules of one or more solvents per molecule of the compound of formula I. The about stoichiometric amount of (the one or more) solvent molecules in said solvate preferably lies in the range of about 0.1 solvent molecules to about 7 solvent molecules per molecule of the compound according to formula I, more preferably in the range of about 0.5 solvent molecules per molecule of the compound according to formula I up to about 4.5 solvent molecules per molecule of the compound according to formula I and even more preferably in a range of about 1.5 solvent molecules per molecule of the compound according to formula I up to about 4 solvent molecules per molecule of the compound according to formula I, for example about 0.5 solvent molecules, about 1.5 solvent molecules, about 3 solvent molecules, about 4 solvent molecules or about 7 solvent molecules per molecule of the compound according to formula I contained in said unit cell. Especially preferred are solvates having about four solvent molecules per molecule of the compound according to formula I.

Thus, solvate more preferably means that the respective crystalline form contains an about stoichiometric amount of solvent molecules of one or more solvents per molecule of the compound of formula I. The about stoichiometric amount of (the one or more) solvent molecules in said solvate preferably lies in the range of about 0.5 solvent molecules to about 6 solvent molecules per molecule of the compound according to formula I, more preferably in the range of about 0.5 solvent molecules up to about 4.5 solvent molecules per molecule of the compound according to formula I and even more preferably in a range of about 1.5 solvent molecules per molecule of the compound according to formula I up to about 4 solvent molecules per molecule of the compound according to formula I, for example about 0.5 solvent molecules, about 1.5 solvent molecules, about 4 solvent molecules or about 6 solvent molecules per molecule of the compound according to formula I. Especially preferred are solvates having about four solvent molecules per molecule of the compound according to formula I.

Figure 34:
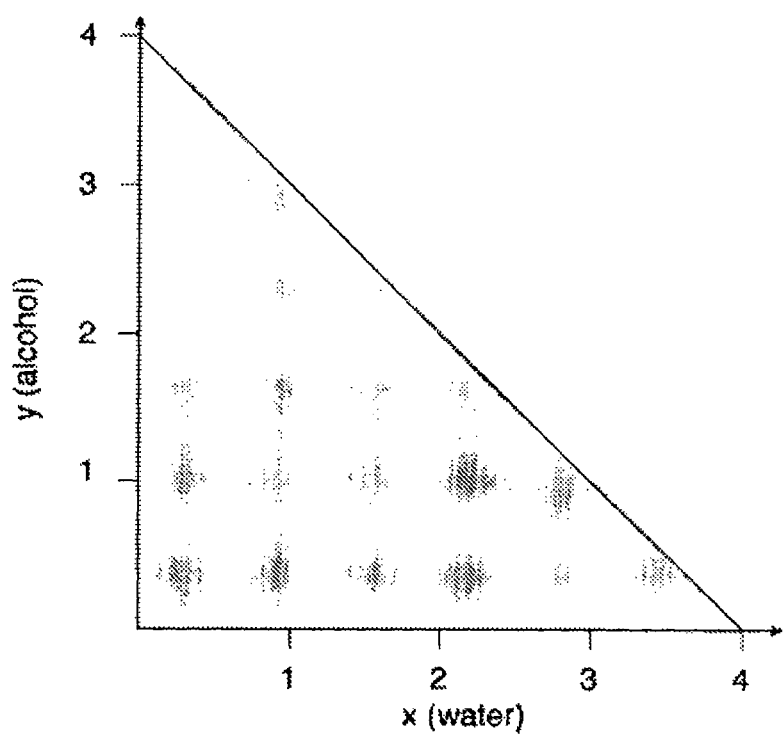
FIGS. 34-36 depict stoichiometries of several embodiments of the invention.

More preferred stoichiometries of the solvate are defined as depicted in the area shaded in grey in FIG. 34.

In FIG. 34 x is the number of water molecules per molecule of the compound according to formula I (which might be integer or non-integer) and y is the number of molecules of alcohol, preferably either methanol or ethanol or mixtures thereof, and might be integer or non-integer. Accordingly, preferably the number of alcohol molecules per molecule of the compound according to formula I is in between 0 and about 4, and preferably between 0.1 and 4, and the number of water molecules is in between 0 and about 4, and preferably between 0.1 and 4.

Figure 35:
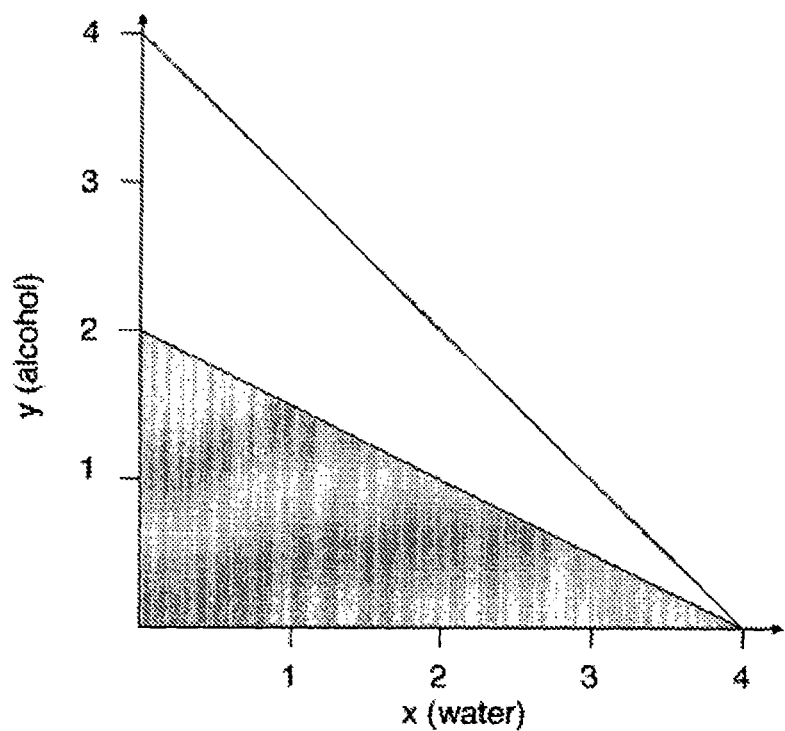

Even more preferred stoichiometries of the solvate are defined as depicted in the area shaded in grey in FIG. 35.

In FIG. 35 x is the number of water molecules per molecule of the compound according to formula I (which might be integer or non-integer) and y is the number of molecules of alcohol, preferably either methanol or ethanol or mixtures thereof, and might be integer or non-integer. Accordingly, preferably the number of alcohol molecules per molecule of the compound according to formula I is in between 0 and about 2, and preferably between 0.1 and 2, and the number of water molecules is in between 0 and about 4, and preferably between 0.1 and 4.

Figure 36:
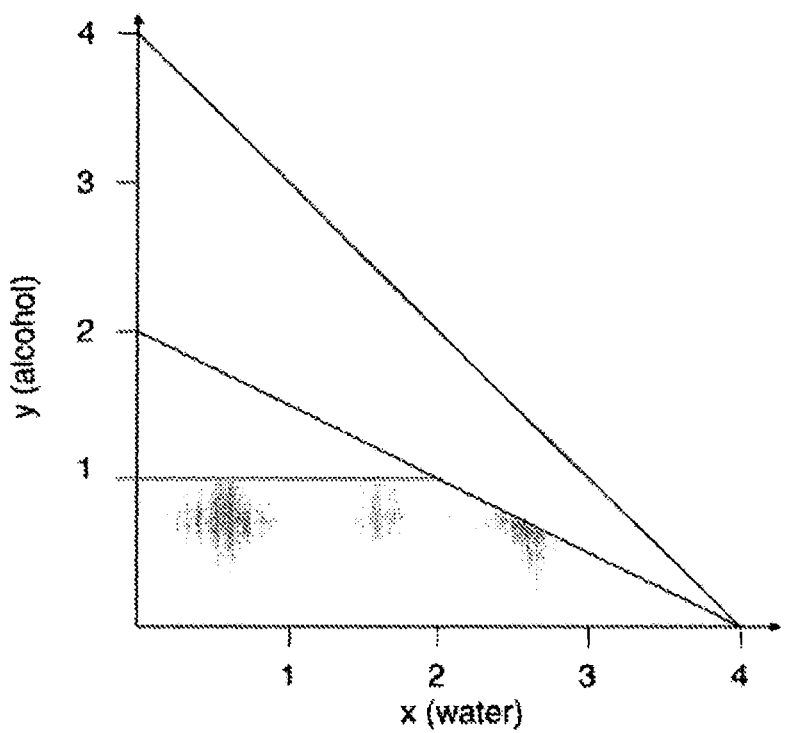

Still even more preferred stoichiometries of the solvate are defined as depicted in the area shaded in grey in FIG. 36.

In FIG. 36 x is the number of water molecules per molecule of the compound according to formula I (which might be integer or non-integer) and y is the number of molecules of alcohol, preferably either methanol or ethanol or mixtures thereof, and might be integer or non-integer. Accordingly, preferably the number of alcohol molecules per molecule of the compound according to formula I is in between 0 and about 1, more preferably between 0.1 and 1, and the number of water molecules is in between 0 and about 4, and preferably between 0.1 and 4.

Especially preferred solvents or solvent molecules in this regard are selected from the group consisting of water and alcohols, and more preferably selected from the group consisting of water, methanol and ethanol.

Solvates of the compound according to formulae I having the composition or stoichiometry as described in FIG. 34, FIG. 35 and/or FIG. 36 and preferably also as described in the paragraphs relating thereto, respectively, are especially preferred subject of the instant invention. The above and/or below described solvates are especially preferred examples for said solvates having a composition or stoichiometry within the ranges as described in FIG. 34, FIG. 35 and/or FIG. 36 and thus are also especially preferred subjects of the instant invention.

Based on the description given above and/or below and preferably also on the description of the solvates or crystalline forms S1, S2 and/or S3, it becomes apparent that the solvates or crystalline forms characterised by a unit cell with the unit cell parameters ULP1 can comprise 0 to about 4 solvent molecules per molecule of the compound of formula I within said unit cell, more preferably 0.01 to about 4 solvent molecules per molecule of the compound of formula I within said unit cell and especially 0.5 to 4 solvent molecules per molecule of the compound of formula I within said unit cell.

Thus, a common feature or characteristic of the solvates or crystalline forms characterised by a unit cell with the unit cell parameters ULP1 is the upper limit of the solvent content of about four molecules of one or more solvents, preferably solvents as described herein, per molecule of the compound according to formula I. In accordance with the art, the solvates or crystalline forms characterised by an upper limit of the solvent content of about four molecules of one or more solvents per molecule of the compound of formula I in said unit cell are preferably referred to as tetrasolvates.

However, as is extensively described herein, said solvates or crystalline forms characterised by a unit cell with the unit cell parameters ULP1 can be desolvated to a solvent content of about 3 or less solvent molecules per molecule of the compound of formula I within said unit cell, to a solvent content of about 2 or less solvent molecules per molecule of the compound of formula I within said unit cell, to a solvent content of about 1 or less solvent molecules per molecule of the compound of formula I within said unit cell, or even to a solvent content of close to 0.5, 0.1 or 0 solvent molecules per molecule of the compound of formula I within said unit cell. These desolvates of the solvates or crystalline forms characterised by a unit cell with the unit cell parameters ULP1 are also at preferred subject of the instant invention.

As a result, the term "tetrasolvate" and/or "tetrahydrate" as used herein preferably also includes the partly or totally desolvated forms of said tetrasolvates and/or tetrahydrates, preferably as long as the respective crystal structure of the original tetrasolvate or tetrahydrate is retained or essentially retained.

As a further result, the term "tetrasolvate" as used herein preferably also includes alcohol solvates (or alcoholates) or mixed water-alcohol solvates, preferably including, but not limited to the Dihydrate-dialcoholate, the Dihydrate-alcoholate and the Dihydrate-monoalcoholate, and/or the partly or totally desolvated forms thereof, preferably as long as the respective crystal structure of the original tetrasolvate and especially preferably the original crystal structure of the tetrahydrate S3 is retained or essentially retained.

As a further result, the term "tetrasolvate" as used herein preferably also includes alcohol solvates (or alcoholates) or mixed water-alcohol solvates, preferably including, but not limited to the Dihydrate-dialcoholate, the Dihydrate-alcoholate, the Dihydrate-monoalcoholate and the Dialcoholate (preferably given by the formula $(Cil)_1(Alcohol)_2(H_2O)_0$), and/or the partly or totally desolvated forms thereof, preferably as long as the respective crystal structure of the original tetrasolvate and especially preferably the original crystal structure of the tetrahydrate S3 is retained or essentially retained. Thus, all crystalline forms within the unit cell parameters according to ULP1 as defined herein are preferably regarded as tetrasolvates according to the instant invention.

Preferably, the Dialcoholates according to the invention are to be regarded as tetrasolvates and/or desolvates thereof, which preferably contain about two alcohol molecules per molecule of the compound of formula I, but which preferably contain less than one molecule, more preferably less than 0.5 molecules and especially less than 0.1 water molecules per molecule of the compound of formula I. Thus, preferred dialcoholates according to the invention contain about 4 molecules of the compound of formula I and about 8 molecules of alcohol in the unit cell, but preferably less than one molecule of water. Preferably, the alcohol in said dialcoholates is selected from methanol and ethanol and mixtures thereof. Thus, the dialcoholates according to the invention can preferably also be regarded as desolvates or more specifically as dehydrates of the Dihydrate-dialcoholates according to the invention.

The crystalline form A1 preferably is further characterised as an anhydrate or ansolvate.

In this regard, anhydrate or ansolvate preferably means that the unit cell is free or essentially free of about stoichiometric amounts of solvent molecules of one or more solvents. In this regard, anhydrate or ansolvate more preferably means that the unit cell is essentially free of water and solvent molecules. Essentially free of solvent molecules in this regard preferably means that the amount of solvent molecules in the unit cell is lower than 0.5, more preferably lower than 0.1, even more preferably lower than 0.01 and especially lower than 0.001.

Since both ansolvates and an anhydrates are characterised by the absence of the respective solvents and thus characterised by the absence of any solvent, the terms anhydrate and ansolvate are preferably to be regarded as synonyms in the context of the present invention.

The amount of molecules in the unit cell is preferably determined by crystallographic methods, more preferably by single crystal X-ray diffraction and/or powder X-ray diffraction.

Alternatively, the amount of solvent in said crystalline forms, said solvates and/or in the respective unit cell can be determined or estimated by elemental analysis, gas chromatography or Karl-Fischer titration. In this context, essentially free of solvent molecules preferably means a solvent content of less than 5%, even more preferably less than 2%, even more preferably less than 1% and especially less than 0.1%, for example 5% to 0.1% or 2% to 0.01%. In this regard, the given percentages (%) are preferably selected from mole % and % by weight and especially preferably are % by weight.

The crystalline forms A1, S2 and/or S3 are preferably further characterised by orthorhombic unit cell.

The crystalline form S1 is preferably further characterised by a monoclinic unit cell.

The unit cell and the lattice parameters, preferably including, but not limited to a, b, c, α, β and/or γ, are crystallographic parameters known to the ones skilled in the art. Hence, they can be determined according to methods known in the art. The same preferably holds true for the orthorhombic and/or monoclinic form of the unit cell.

The above given unit cells and the lattice parameters relating thereto are preferably determined by X-Ray Diffraction, more preferably Single Crystal X-Ray Diffraction and/or Powder X-Ray Diffraction, according to standard methods, for example methods or techniques as described in the European Pharmacopeia 6$^{th}$ Edition chapter 2.9.33, and/or as described in Rolf Hilfiker, 'Polymorphism in the Pharmaceutical Industry', Wiley-VCH. Weinheim 2006 (Chapter 6: X-Ray Diffraction), and/or H. G. Brittain, 'Polymorphism in Pharmaceutical Solids, Vol. 95, Marcel Dekker Inc., New York 1999 (Chapter 6 and references therein).

Alternatively preferably, the above given unit cells and the lattice parameters relating thereto can be obtained by single crystal X-Ray, optionally together with additional structure data, preferably conducted on a XCalibur diffractometer from Oxford Diffraction equipped with graphite monochromator and CCD Detector using Mo K$_\alpha$ radiation, preferably at a temperature of 298K±5 K; and/or on a CAD4 four circle diffractometer from Nonius equipped with graphite monochromator and scintillation counter using Mo K$_\alpha$ radiation, preferably at a temperature of 298 K±5 K.

The above given unit cells and the lattice parameters relating thereto are preferably determined by X-Ray Diffraction, more preferably Powder X-Ray Diffraction, according to standard methods, for example methods or techniques as described in the European Pharmacopeia 6$^{th}$ Edition chapter 2.9.33, and/or as described in Rolf Hilfiker, 'Polymorphism in the Pharmaceutical Industry', Wiley-VCH. Weinheim 2006 (Chapter 6: X-Ray Diffraction), and/or H. G. Brittain, 'Polymorphism in Pharmaceutical Solids, Vol. 95, Marcel Dekker Inc., New York 1999 (Chapter 6 and references therein).

Higher contents of the one or more crystalline forms as defined above and/or below in the solid material as described above and/or below are generally preferred.

A solid material as described above and/or below, essentially consisting of one or more crystalline forms of the compound of formula I, characterised by a unit cell with the lattice parameters $$a=9.5\pm0.5\ \text{Å},$$

$$b=23.0\pm5.0\ \text{Å},$$

and $$c=14.7\pm1.0\ \text{Å},$$

and especially characterised as described above and/or below.

Essentially consisting of one or more crystalline forms of the compound of formula I preferably means that the compound of formula I contained in said solid material is essentially selected from said one or more crystalline forms of the compound of formula I, or in other words, that the one or more crystalline forms in said solid form provide for the essential amount of compound of formula I in said solid form. More specifically, essentially in this regard preferably means that the one or more crystalline forms in said solid form provide for 90% or more, preferably 95% or more, even more preferably 99% or more and especially 99.9% or more, of the amount of compound of formula I in said solid form. In this regard, the given percentages (%) are preferably selected from mole % and % by weight and especially preferably are mole %.

Said amounts can be provided by one single crystalline form as described herein, or by mixtures of two or more crystalline forms as described herein. Preferably, said amounts are provided by one single crystalline form as described herein. More preferably, said amounts are provided by one single crystalline form, selected from crystalline form A1, crystalline form S1, crystalline form S2 and crystalline form S3 as described herein.

If the solid material comprises two or more of the crystalline forms as described herein, one of these crystalline forms is preferably the major crystalline form and the one or more further crystalline forms present are present in minor amounts. The major crystalline form preferably provides for 60% by weight or more, more preferably 75% or more, even more preferably 90% or more and especially 95 or 99% or more, of the total amount of the crystalline forms present. In this regard, the given percentages (%) are preferably selected from mole % and % by weight and especially preferably are mole %.

If not specified otherwise, percentages (or %) given herein for compounds and/or solvents are preferably either percentages by weight or mole percent, preferably mole percent. Since the content of the one or more crystalline forms in the solid material according to the invention, and, if applicable, the ratio of two or more crystalline forms in the solid material according to the invention, can advantageously be determined via methods including, but not limited to, Powder X-Ray-Diffraction, Raman-spectroscopy and infrared spectroscopy, and more preferably are determined by Powder X-Ray-Diffraction, Raman-spectroscopy and/or infrared spectroscopy, percent values related thereto are especially preferably mole percent values, if not explicitly stated otherwise.

Preferably, if not specified otherwise, percentages (or %) given herein
  i) for spectral data, such as transmission, especially IR transmission, Raman intensity;
  ii) Powder X-Ray diffraction intensities (PXRD intensities); and/or
  iii) analytical parameters, such as relative humidity (rh or r.h.), and the like,
are preferably relative percentages (i.e. percent of the respective maximum value).

A preferred subject of the invention are the one or more crystalline forms of the compound of formula I as described herein and especially as described above and/or below.

Preferably, the one or more crystalline forms of the compound of formula I are selected from the crystalline forms as described above and/or below having a monoclinic unit cell or a orthorhombic unit cell.

Preferably, the one or more crystalline forms of the compound of formula I are selected from anhydrates or ansolvates and solvates.

Preferably, the solvates are selected from hydrates, methanolates (methanol solvates), and ethanolates (ethanol solvates), and mixtures thereof. Said mixtures are preferably selected from mixed water-methanol solvates, mixed water ethanol solvates, mixed methanol-ethanol solvates, and mixed methanol-ethanol-water-solvates.

Preferably, the anhydrates or ansolvates according to the invention and especially the crystalline form A1 can be characterised, alternatively or additionally, by a melting/decomposition temperature of >282° C., more preferably 288±5° C. or higher, and especially 288±5° C.

The melting/decomposition temperatures and/or thermal behaviors described herein are preferably determined by DSC (Differential Scanning calorimetry) and TGA (Thermo-Gravimetric Analysis). DSC and/or TGA methods or generally thermoanalytic methods and suitable devices for determining them are known in the art, for examples from European Pharmacopeia 6$^{th}$ Edition chapter 2.02.34, wherein suitable standard techniques are described. More preferably, for the melting/decomposition temperatures or behaviors and/or the thermoanalysis in generally, a Mettler Toledo DSC 821 and/or Mettler Toledo TGA 851 are used, preferably as described in the European Pharmacopeia 6$^{th}$ Edition chapter 2.02.34.

Figure 2:
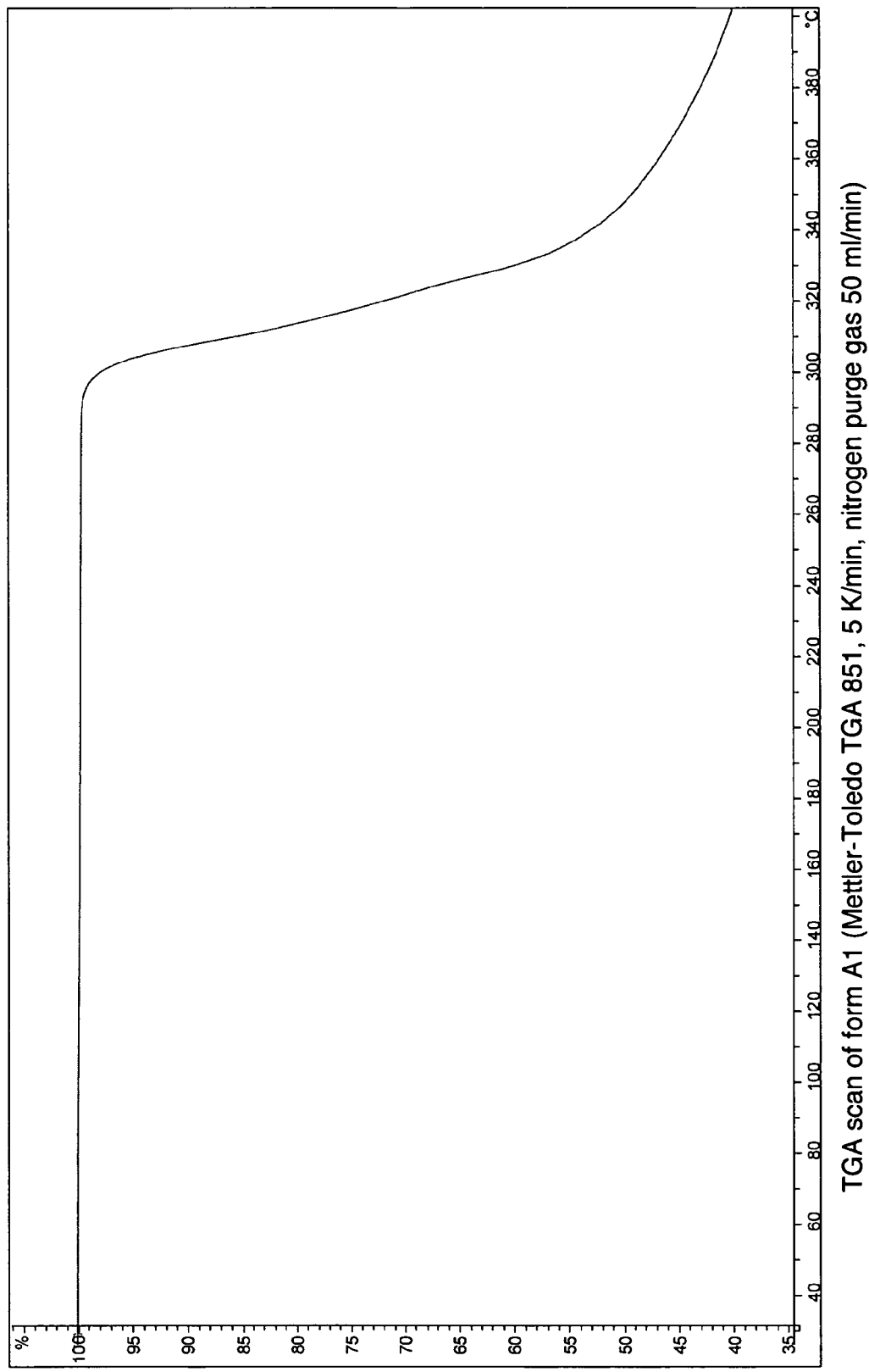
FIG. 2 depicts the TGA measurements of crystalline form A1.

The DSC and TGA measurements showing the thermal analysis (Mettler-Toledo DSC 821, 5 K/min, nitrogen purge gas 50 ml/min; Mettler-Toledo TGA 851, K/min, nitrogen purge gas 50 ml/min) and the melting/decomposition temperature given above is shown in FIG. 1 and FIG. 2.

Preferably, the anhydrates or ansolvates according to the invention and especially the crystalline form A1 can be characterised, alternatively or additionally, by Powder X-Ray Diffraction and more preferably by the Powder X-Ray Diffraction pattern comprising one or more of the Powder X-ray peaks given below, more preferably comprising 6 or more of the Powder X-ray peaks given below, even more preferably 8 or more of the Powder X-ray peaks given below, and especially comprising all of the of the Powder X-ray peaks given below:

| | a) | | | | |
|---|---|---|---|---|---|
| | D ± 0.1 | °2 θ (Cu-Kα$_1$, | Miller indices | | |
| No. | [Å] | radiation) ± 0.1° | h | k | l |
| 1 | 12.08 | 7.3 | 0 | 1 | 1 |
| 2 | 9.75 | 9.1 | 0 | 0 | 2 |
| 4 | 8.24 | 10.7 | 1 | 1 | 0 |
| 7 | 6.91 | 12.8 | 1 | 0 | 2 |
| 8 | 6.05 | 14.6 | 1 | 2 | 0 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.2 | 2 | 0 | 2 |
| 13 | 4.21 | 21.1 | 2 | 1 | 2 |
| 14 | 4.12 | 21.2 | 2 | 2 | 0 |
| 15 | 3.79 | 23.4 | 2 | 1 | 3 | or more preferably

| | b) | | | | |
|---|---|---|---|---|---|
| | D ± 0.1 | °2 θ (Cu-Kα$_1$, | Miller indices | | |
| No. | [Å] | radiation) ± 0.1° | h | k | l |
| 1 | 12.08 | 7.3 | 0 | 1 | 1 |
| 2 | 9.75 | 9.1 | 0 | 0 | 2 |
| 4 | 8.24 | 10.7 | 1 | 1 | 0 |
| 7 | 6.91 | 12.8 | 1 | 0 | 2 |
| 8 | 6.05 | 14.7 | 0 | 2 | 2 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.3 | 2 | 0 | 2 |
| 13 | 4.21 | 21.1 | 2 | 1 | 2 |
| 14 | 4.12 | 21.5 | 2 | 2 | 0 |
| 15 | 3.79 | 23.4 | 2 | 1 | 3 |

Preferably, the anhydrates or ansolvates according to the invention and especially the crystalline form A1 can be characterised, alternatively or additionally, by Powder X-Ray Diffraction and more preferably by the Powder X-Ray Diffraction pattern comprising the Powder X-ray peaks given below:

| | a) | | | | |
|---|---|---|---|---|---|
| | D | °2 θ (Cu-Kα$_1$, | Miller indices | | |
| No. | [Å] | radiation) ± 0.1° | h | k | l |
| 1 | 12.08 | 7.3 | 0 | 1 | 1 |
| 2 | 9.75 | 9.1 | 0 | 0 | 2 |
| 4 | 8.24 | 10.7 | 1 | 1 | 0 |
| 7 | 6.91 | 12.8 | 1 | 0 | 2 |
| 8 | 6.05 | 14.6 | 1 | 2 | 0 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.2 | 2 | 0 | 2 |
| 13 | 4.21 | 21.1 | 2 | 1 | 2 |
| 14 | 4.12 | 21.2 | 2 | 2 | 0 |
| 15 | 3.79 | 23.4 | 2 | 1 | 3 | or more preferably

| | b) | | | | |
|---|---|---|---|---|---|
| | D | °2 θ (Cu-Kα$_1$, | Miller indices | | |
| No. | [Å] | radiation) ± 0.1° | h | k | l |
| 1 | 12.08 | 7.3 | 0 | 1 | 1 |
| 2 | 9.75 | 9.1 | 0 | 0 | 2 |
| 4 | 8.24 | 10.7 | 1 | 1 | 0 |
| 7 | 6.91 | 12.8 | 1 | 0 | 2 |

-continued

| b) | | | | | |
|---|---|---|---|---|---|
| No. | D [Å] | °2θ (Cu-Kα₁, radiation) ± 0.1° | Miller indices h | k | l |
| 8 | 6.05 | 14.7 | 0 | 2 | 2 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.3 | 2 | 0 | 2 |
| 13 | 4.21 | 21.1 | 2 | 1 | 2 |
| 14 | 4.12 | 21.5 | 2 | 2 | 0 |
| 15 | 3.79 | 23.4 | 2 | 1 | 3 |

Preferably, the anhydrates or ansolvates according to the invention and especially the crystalline form A1 can be characterised, alternatively or additionally, by Powder X-Ray Diffraction and more preferably by the Powder X-Ray Diffraction pattern comprising one or more of the Powder X-ray peaks given below, more preferably comprising 10 or more of the Powder X-ray peaks given below, even more preferably 12 or more of the Powder X-ray peaks given below, and especially comprising all of the of the Powder X-ray peaks given below:

| a) | | | | | |
|---|---|---|---|---|---|
| No. | D ± 0.1 [Å] | °2θ (Cu-Kα₁, radiation) ± 0.1° | Miller indices h | k | l |
| 1 | 12.08 | 7.3 | 0 | 1 | 1 |
| 2 | 9.75 | 9.1 | 0 | 0 | 2 |
| 3 | 8.75 | 10.1 | 1 | 0 | 1 |
| 4 | 8.24 | 10.7 | 1 | 1 | 0 |
| 5 | 7.69 | 11.5 | 0 | 2 | 0 |
| 6 | 7.16 | 12.4 | 0 | 2 | 1 |
| 7 | 6.91 | 12.8 | 1 | 0 | 2 |
| 8 | 6.05 | 14.6 | 1 | 2 | 0 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.2 | 2 | 0 | 2 |
| 13 | 4.21 | 21.1 | 2 | 1 | 2 |
| 14 | 4.12 | 21.2 | 2 | 2 | 0 |
| 15 | 3.79 | 23.4 | 2 | 1 | 3 | or more preferably

| b) | | | | | |
|---|---|---|---|---|---|
| No. | D ± 0.1 [Å] | °2θ (Cu—Kα₁ radiation) ± 0.1° | Miller indices h | k | l |
| 1 | 12.08 | 7.3 | 0 | 1 | 1 |
| 2 | 9.75 | 9.1 | 0 | 0 | 2 |
| 3 | 8.75 | 10.1 | 1 | 0 | 1 |
| 4 | 8.24 | 10.7 | 1 | 1 | 0 |
| 5 | 7.69 | 11.5 | 0 | 2 | 0 |
| 6 | 7.16 | 12.4 | 0 | 2 | 1 |
| 7 | 6.91 | 12.8 | 1 | 0 | 2 |
| 8 | 6.05 | 14.7 | 0 | 2 | 2 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.3 | 2 | 0 | 2 |
| 13 | 4.21 | 21.1 | 2 | 1 | 2 |
| 14 | 4.12 | 21.5 | 2 | 2 | 0 |
| 15 | 3.79 | 23.4 | 2 | 1 | 3 |

The Powder X-Ray Diffraction and more preferably the Powder X-Ray Diffraction pattern is preferably performed or determined as described herein and especially performed or determined by standard techniques as described in the European Pharmacopeia 6$^{th}$ Edition chapter 2.9.33, and is even more preferably obtained with the parameters Cu—Kα₁ radiation and/or λ=1.5406 Å, preferably on a Stoe StadiP 611 KL diffractometer.

Figure 3:
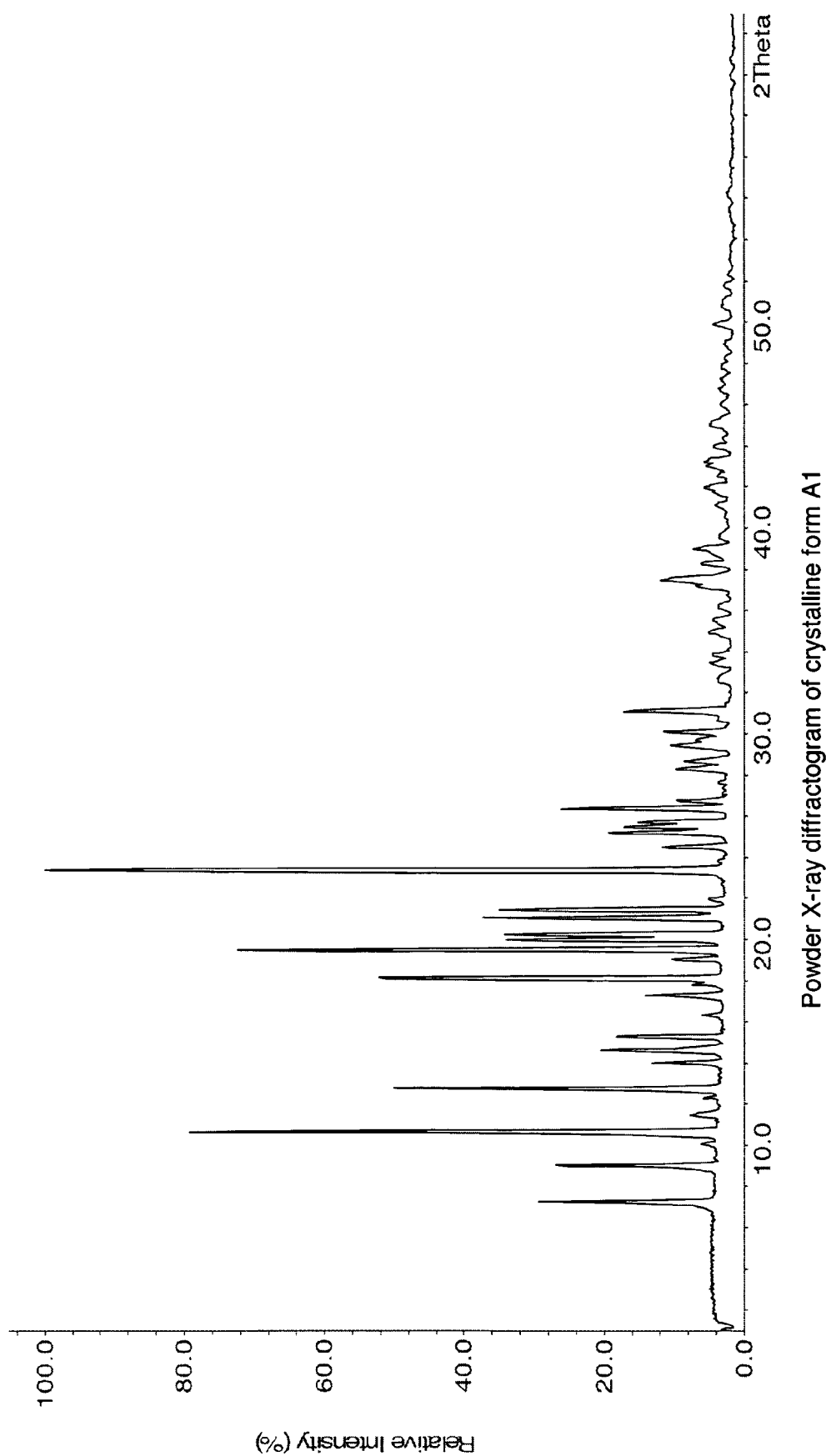
FIG. 3 depicts the powder x-ray diffractogram of crystalline form A1.

FIG. 3 shows the Powder X-ray diffractogram of crystalline form A1

Preferably, the anhydrates or ansolvates according to the invention and especially the crystalline form A1 can be characterised, alternatively or additionally, by Single Crystal X-Ray Structure Data, for example Single Crystal X-Ray Structure Data obtained on a diffractometer preferably equipped with a graphite monochromator and CCD Detector, preferably using Mo K$_α$ radiation, preferably at a temperature of 298 K±5 K, and even more preferably on a XCalibur diffractometer from Oxford Diffraction equipped with graphite monochromator and CCD Detector using Mo K$_α$ radiation at about 298 K.

According to the Single Crystal X-Ray Structure Data obtained, the anhydrate of the compound of formula I and especially crystalline form A1 crystallises in the orthorhombic space group P 2₁ 2₁ 2₁ with the lattice parameters a=9.8 Å, b=15.4 Å, c=19.5 Å (±0.1 Å) and the unit cell volume is preferably 2940 (±10) Å³

From the single crystal structure it is obvious that form A1 represents an anhydrate or ansolvate.

Figure 4:
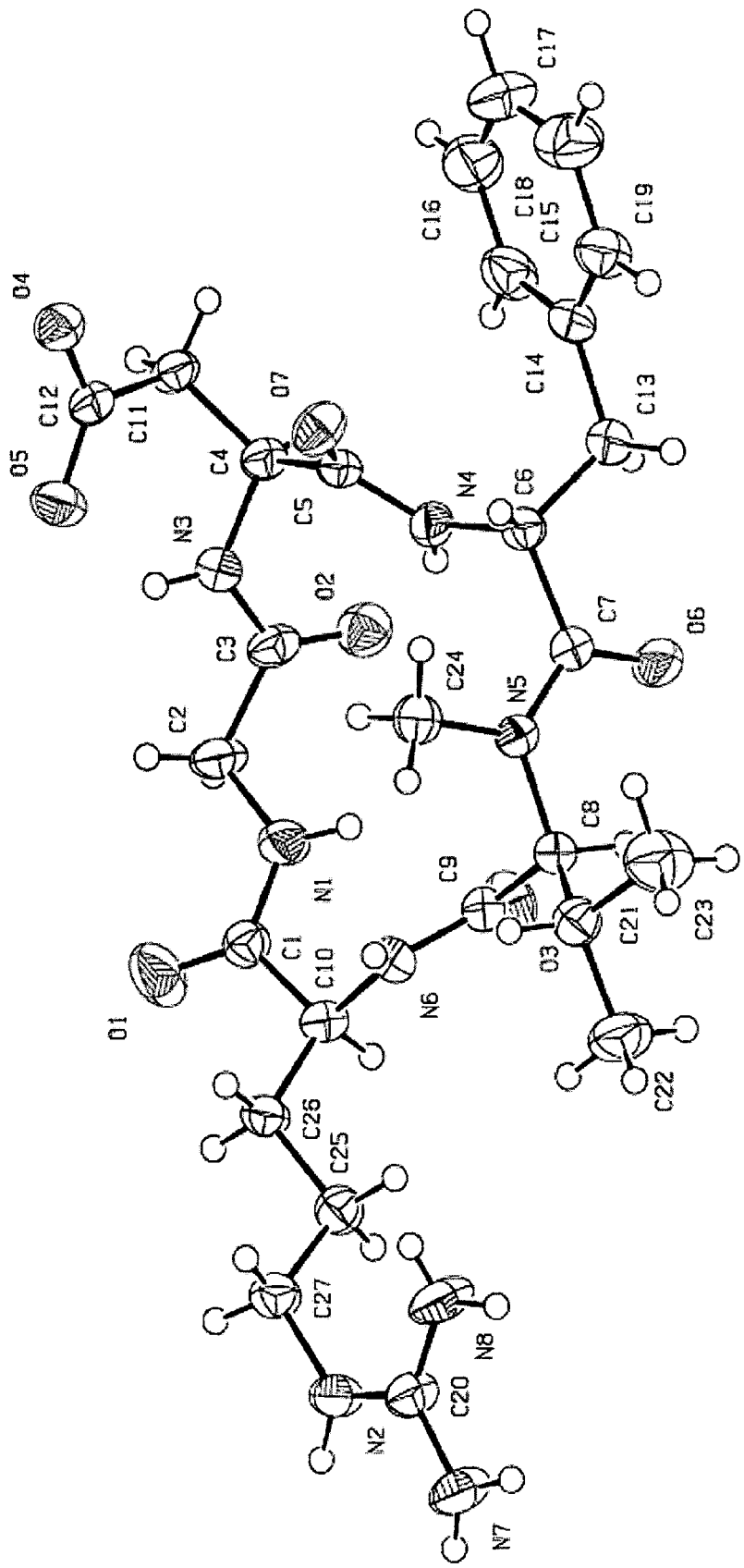
FIG. 4 depicts a single crystal x-ray structure of crystalline form A1.

The Single Crystal X-Ray Structure is depicted in FIG. 4.

Preferably, the anhydrates and ansolvates according to the invention and especially the crystalline form A1 can be characterised, alternatively or additionally, by the infrared-spectroscopy data comprising one or more of the band positions (±2 cm$^{-1}$) given below, more preferably comprising 6 or more of the band positions (±2 cm$^{-1}$) given below, even more preferably comprising 9 or more of the band positions (±2 cm$^{-1}$) given below, and especially comprising all the band positions (±2 cm$^{-1}$) given below, preferably together with the relative intensities given in brackets:

3431 cm$^{-1}$ (s), 3339 cm$^{-1}$ (s), 3189 cm$^{-1}$ (s), 2962 cm$^{-1}$ (m), 2872 cm$^{-1}$ (m), 1676 cm$^{-1}$ (s), 1660 cm$^{-1}$ (s), 1617 cm$^{-1}$ (s), 1407 cm$^{-1}$ (s), 1316 cm$^{-1}$ (m), 1224 cm$^{-1}$ (m), 1186 cm$^{-1}$ (m), 711 cm$^{-1}$ (m).

More preferably, the anhydrates and ansolvates according to the invention and especially the crystalline form A1 can be characterised, alternatively or additionally, by the infrared-spectroscopy data comprising one or more of the band positions (±2 cm$^{-1}$) given below, more preferably comprising 9 or more of the band positions (±2 cm$^{-1}$) given below, even more preferably comprising 12 or more of the band positions (±2 cm$^{-1}$) given below, and especially comprising all the band positions (±2 cm$^{-1}$) given below, preferably together with the relative intensities given in brackets:

3431 cm$^{-1}$ (s), 3339 cm$^{-1}$ (s), 3189 cm$^{-1}$ (s), 3031 cm$^{-1}$ (m), 2962 cm$^{-1}$ (m), 2872 cm$^{-1}$ (m), 1676 cm$^{-1}$ (s), 1660 cm$^{-1}$ (s), 1617 cm$^{-1}$ (s), 1539 cm$^{-1}$ (s), 1493 cm$^{-1}$ (s), 1407 cm$^{-1}$ (s), 1358 cm$^{-1}$ (m), 1316 cm$^{-1}$ (m), 1247 cm$^{-1}$ (m), 1224 cm$^{-1}$ (m), 1186 cm$^{-1}$ (m), 994 cm$^{-1}$ (w), 921 cm$^{-1}$ (w), 711 cm$^{-1}$ (m), 599 cm$^{-1}$ (m).

The relative intensities given in brackets are preferably defined as follows: *"s"=strong (transmittance preferably ≤50%), "m"=medium (preferably 50%<transmittance≤70%), "w"=weak (transmittance preferably >70%)

The IR or FT-IR spectrum is preferably obtained using a KBr pellet as sample preparation technique.

The IR-spectroscopy data is preferably obtained by FT-IR-spectroscopy, The IR-spectroscopy data or FT-IR-spectroscopy data is preferably obtained by standard techniques as described in the European Pharmacopeia 6$^{th}$ Edition chapter 2.02.24. For the measurement of the FT-IR-spectra, preferably a Bruker Vector 22 spectrometer is used. FT-IR spectra are preferably base-line corrected, preferably using Bruker OPUS software.

Figure 5:
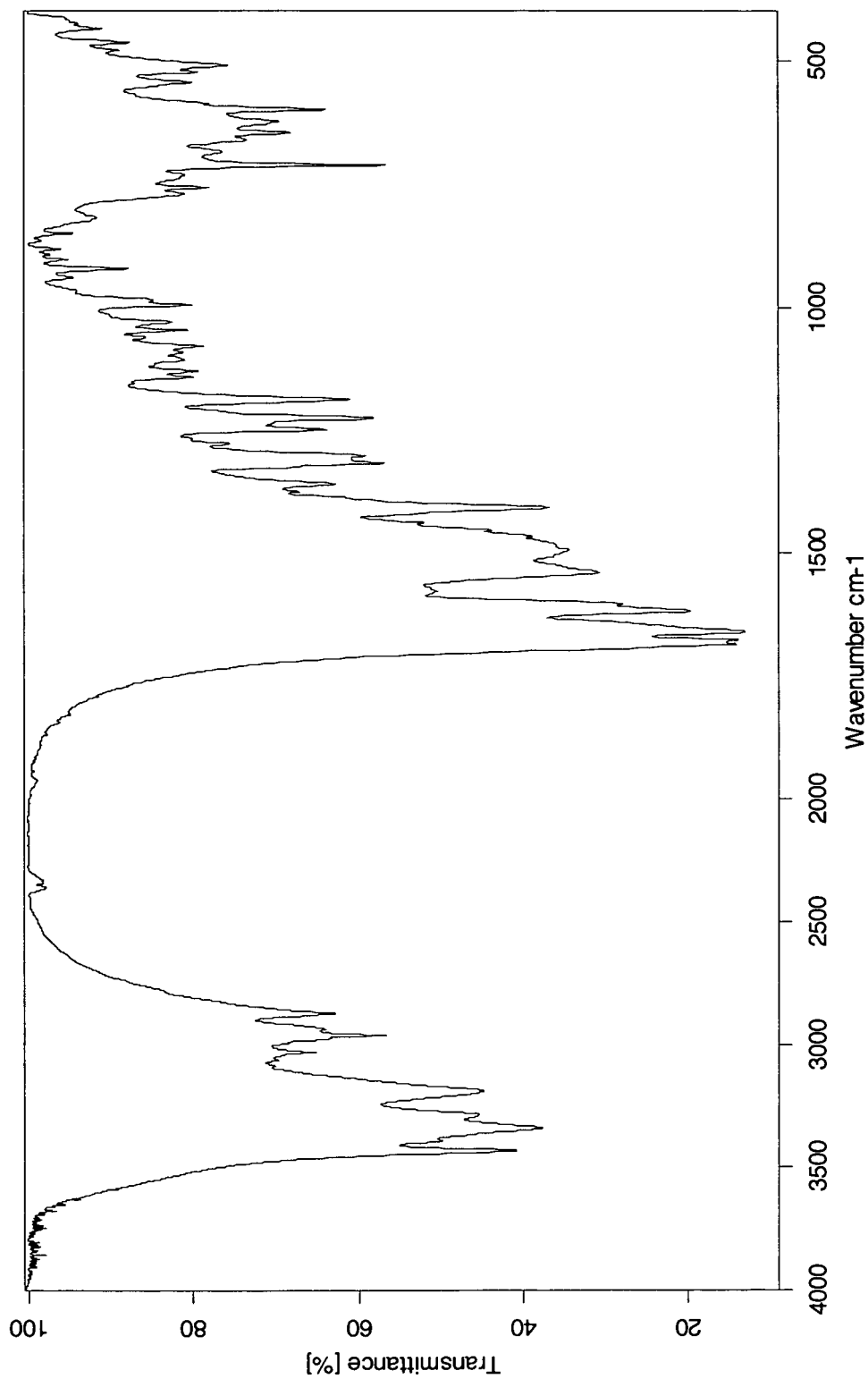
FIG. 5 depicts the FT-IR spectrum of crystalline form A1.

The FT-IR spectra of the anhydrates according to the invention and especially the crystalline form A1 is given in FIG. 5.

Preferably, the anhydrates or ansolvates according to the invention and especially the crystalline form A1 can be characterised, alternatively or additionally, by the Raman-spectroscopy data comprising one or more of the band positions (±2 cm$^{-1}$) given below, more preferably comprising 9 or more of the band positions (±2 cm$^{-1}$) given below, even more preferably comprising 9 or more of the band positions (±2 cm$^{-1}$) given below, and especially comprising all the band positions (±2 cm$^{-1}$) given below, preferably together with the relative intensities given in brackets:
3064 cm$^{-1}$ (w), 2976 cm$^{-1}$ (m), 2934 cm$^{-1}$ (m), 2912 cm$^{-1}$ (m), 2881 cm$^{-1}$ (m), 1603 cm$^{-1}$ (w), 1209 cm$^{-1}$ (w), 1029 cm$^{-1}$ (w), 1003 cm$^{-1}$ (m), 852 cm$^{-1}$ (w).

More preferably, the anhydrates or ansolvates according to the invention and especially the crystalline form A1 can be characterised, alternatively or additionally, by the Raman-spectroscopy data comprising one or more of the band positions (±2 cm$^{-1}$) given below, more preferably comprising 12 or more of the band positions (±2 cm$^{-1}$) given below, even more preferably comprising 18 or more of the band positions (±2 cm$^{-1}$) given below, and especially comprising all the band positions (±2 cm$^{-1}$) given below, preferably together with the relative intensities given in brackets:
3064 cm$^{-1}$ (w), 2976 cm$^{-1}$ (m), 2934 cm$^{-1}$ (m), 2912 cm$^{-1}$ (m), 2881 cm$^{-1}$ (m), 1677 cm$^{-1}$ (w), 1648 cm$^{-1}$ (w), 1603 cm$^{-1}$ (w), 1584 cm$^{-1}$ (w), 1465 cm$^{-1}$ (w), 1407 cm$^{-1}$ (w), 1314 cm$^{-1}$ (w), 1242 cm$^{-1}$ (w), 1209 cm$^{-1}$ (w), 1129 cm$^{-1}$ (w), 1029 cm$^{-1}$ (w), 1003 cm$^{-1}$ (m), 943 cm$^{-1}$ (w), 901 cm$^{-1}$ (w), 852 cm$^{-1}$ (w), 623 cm$^{-1}$ (w), 589 cm$^{-1}$ (w).

The relative intensities given in brackets are preferably defined as follows: "s"=strong (relative Raman intensity preferably ≥0.04), "m"=medium (preferably 0.04>relative Raman intensity≥0.02), "w"=weak (relative Raman intensity preferably <0.02)

The Raman or FT-Raman spectrum is preferably obtained using Aluminium-cups as sample holders for the respective solid material.

The Raman-spectroscopy data is preferably obtained by FT-Raman-spectroscopy, The Raman-spectroscopy data or FT-Raman-spectroscopy data is preferably obtained by standard techniques as described in the European Pharmacopeia 6$^{th}$ Edition chapter 2.02.48. For the measurement of the FT-Raman-spectra, preferably a Bruker RFS 100 spectrometer is used. FT-Raman spectra are preferably base-line corrected, preferably using Bruker OPUS software.

Figure 6:
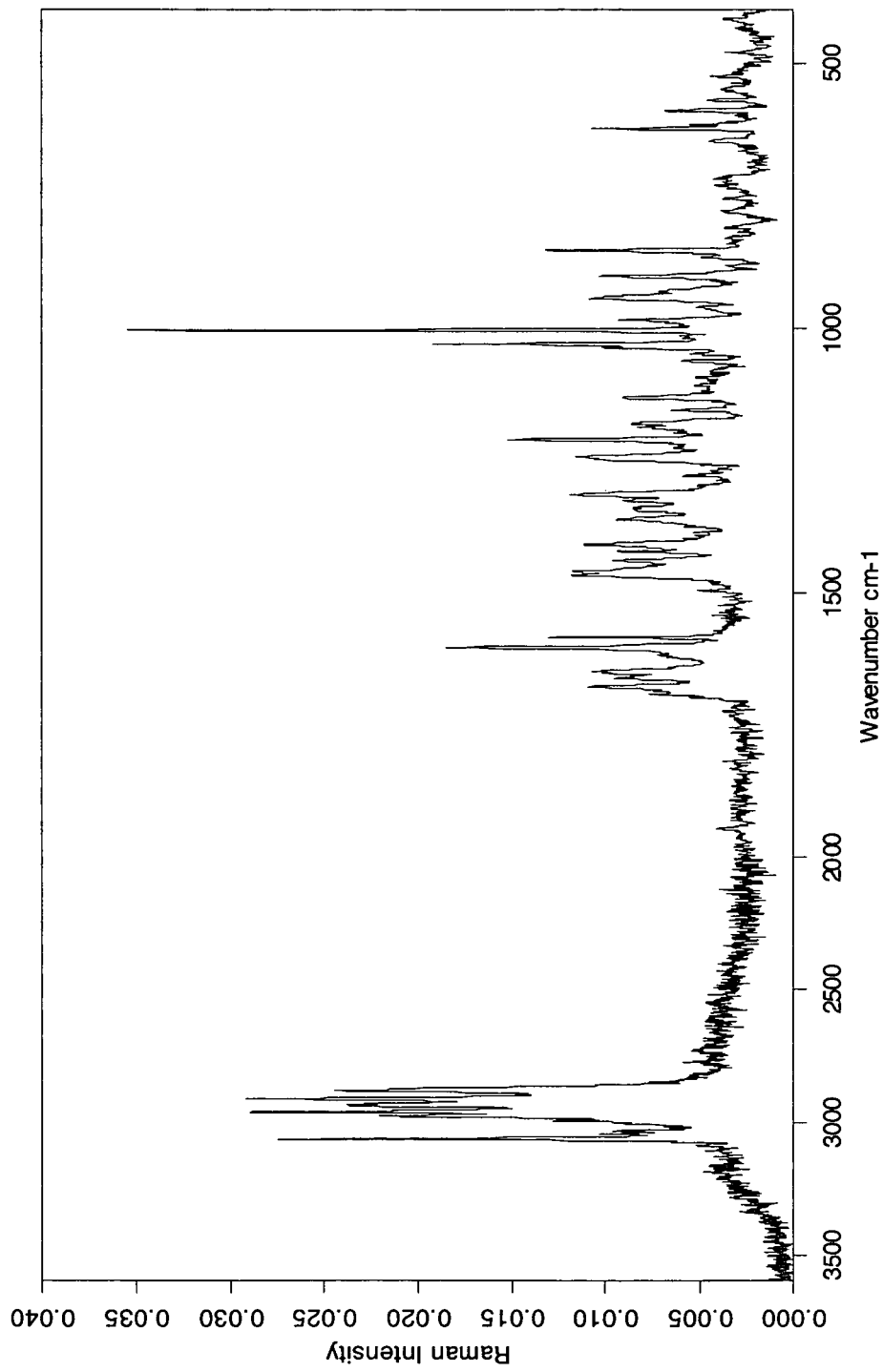
FIG. 6 depicts the FT-Raman spectrum of crystalline form A1.

The FT-Raman spectra of the anhydrates according to the invention and especially the crystalline form A1 is given in FIG. 6.

Figure 7:
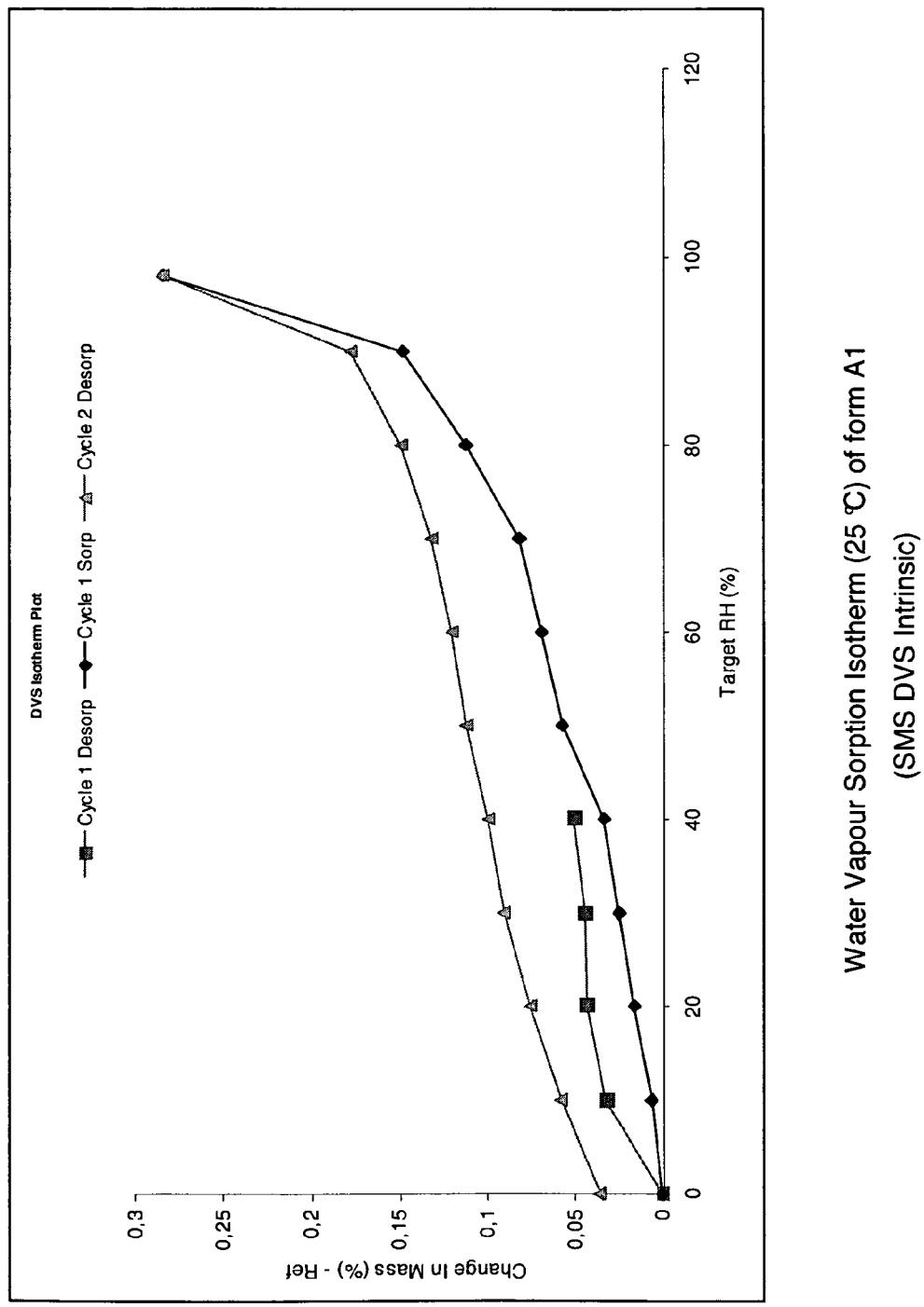
FIG. 7 depicts the water vapour sorption isotherm of crystalline form A1.

Preferably, the anhydrates or ansolvates according to the invention and especially the crystalline form A1 can be characterised, alternatively or additionally, by dynamic vapour sorption experiments. The results can be obtained by standard techniques as described in Rolf Hilfiker, 'Polymorphism in the Pharmaceutical Industry', Wiley-VCH. Weinheim 2006 (Chapter 9: Water Vapour Sorption, and references therein). The Water Vapour Sorption behaviour shows small water uptake levels up to 98% relative humidity (rh or r.h.), and the anhydrates or ansolvates according to the invention and especially the crystalline form A1 can be classified as non-hygroscopic acc. to Ph. Eur. criteria. No formation or conversion to a hydrate is observed. Water Vapor Sorption isotherm (25° C.) of crystallin e form A1 (SMS DVS Intrinsic) is given in FIG. 7.

The anhydrates or ansolvates according to the invention and especially the crystalline form A1 shows one or more properties selected from the advantageous properties discussed above. More specifically, the anhydrates or ansolvates according to the invention and especially the crystalline form A1 can be shown to be the thermodynamically stable ansolvated form and/or thermodynamic stable form and surprisingly the thermodynamically stable form in the presence of aqueous based solvents, preferably including, but not limited to, suspensions and wetted material, and especially in essentially aqueous systems, such as water saline and the like, such as, but not limited to, suspensions and wetted material, and especially in such aqueous systems in the absence of methanol and/or ethanol. Wetted material in this regard is preferably a mixture of the respective anhydrate or ansolvate with at least 5% by weight, more preferably at least 10% by weight and especially 20% by weight, of the respective aqueous system.

More specifically, the anhydrates or ansolvates according to the invention and especially the crystalline form A1 can shown to be the thermodynamically stable ansolvated form and/or thermodynamic stable form and surprisingly the thermodynamically stable form even in the presence of high relative humidity.

Furthermore, the anhydrates according to the invention and especially the crystalline form A1 shows superior properties in terms of hygroscopicity behaviour, with physical stability of the crystal form throughout the entire relative humidity range (0-98%) and/or the crystallinity and thermal behaviour are excellent.

This results in excellent properties for processing (e.g. phase separation by filtration, drying, milling, micronisation) and storage, thus being i.a. superior for the formulation of suspensions. The anhydrates or ansolvates according to the invention and especially the crystalline form A1 exhibit superior properties for the purification of the compound of formula I, since a reduction of structurally related impurities, ionic compounds and residual solvent can be easily achieved. Thus, purificitation can be achieved in one step, where the solid forms, e.g. amorphous forms according to the conventional, prior known processes, and/or other, non-anhydrate polymorhic cyrstalline forms require significantly higher effort for a purity in line with GMP standards, e.g. three or more subsequent purification procedures.

The compound of formula I also forms a class of pseudopolymorphs which incorporate different solvents in variable amounts and/or ratios, preferably ratios, and thus are solvates. These solvates are structurally closely related as shown, e.g. by Powder X-Ray Diffraction data, including indexing of these forms, which leads to similar unit cells.

Also, selected examples for the structures will be discussed based on single-crystal structure and structure solutions based on powder data. Finally a discussion on the specific beneficial properties of this pseudopolymorphic class will be given.

Following, three preferred examples for the pseudopolymorphic forms of the compound according to formula I are described:

S1 (preferably also referred to as methanol-water solvate and/or methanol solvate), S2 (preferably also referred to as ethanol-water solvate and/or ethanol solvate), and S3 (preferably also referred to as hydrate and/or tetrahydrate).

These preferred examples can be further characterised as tetrasolvates.

Thus, the solid crystalline forms having a unit cell with lattice parameters ULP1 as defined before are preferably further characterised herein as solvates and more preferably as tetrasolvates. The solvates and/or tetrasolvates preferably include one or more crystalline forms selected from S1, S2 and S3 as defined herein, and preferably also mixtures thereof.

The crystalline forms S1, S2 and/or S3 are preferably further characterised as solvates and especially as tetrasolvates, i.e. they preferably show an about stoichiometric amount of solvent molecules in the respective unit cell, which is about up to 4 solvent molecules per unit cell and per molecule of the compound according to formula I.

In these solvates and more preferably in these tetrasolvates, the solvent molecules are preferably selected from molecules of water and alcohols and more preferably selected from water, methanol and ethanol, and mixtures thereof.

Accordingly, the solvates can preferably be further characterised as hydrates, alcohol solvates (or alcoholates) or mixed water-alcohol solvates, and more preferably as hydrates, methanol solvates (or methanolates), ethanol solvates (or ethanolates), mixed water-methanol solvates, mixed water-ethanol solvates or mixed water-methanol-ethanol solvates. More specifically, if said solvates are produced from or contacted with mixtures of solvents, e.g. recrystallised from or conditioned with mixtures of solvents, mixed solvates can be obtained. Especially preferably, mixed water alcohol solvates and especially mixed water methanol solvates, mixed water ethanol solvates and/or mixed water-methanol-ethanol solvates can be thus obtained. Additionally, the solvent molecules within one solvate are partially or completely interchangeable for a the solvent molecules of another solvent. Thus, it is clear that the solvates, more preferably the tetrasolvates and especially the crystalline forms S1, S2 and S3 all belong to a specific class of solid crystalline forms.

Preferably, the tetrasolvates according to the invention, more preferably the tetrasolvates according to the invention, more preferably the tetrahydrates according to the invention and especially the crystalline form S3 can be characterised, alternatively or additionally, by a melting/decomposition temperature of >210° C., more preferably 217±5° C. melting/decomposition or higher, and especially 217±5° C. melting/decomposition. Preferably, the melting/decomposition temperature obtained for the tetrasolvates according to the invention, more preferably the tetrahydrates according to the invention and especially obtained for the crystalline form S3 is <250° C.

The melting/decomposition temperatures and/or thermal behaviors described herein are preferably determined by DSC (Differential Scanning calorimetry) and TGA (Thermo-Gravimetric Analysis). DSC and/or TGA methods or generally thermoanalysis methods and suitable devices for determining them are known in the art, for examples from European Pharmacopeia 6th Edition chapter 2.02.34, wherein suitable standard techniques are described. More preferably, for the melting/decomposition temperatures or behaviors and/or the thermoanalysis in general, a Mettler Toledo DSC 821 and/or Mettler Toledo TGA 851 are used, preferably as described in the European Pharmacopeia 6th Edition chapter 2.02.34.

Figure 23:
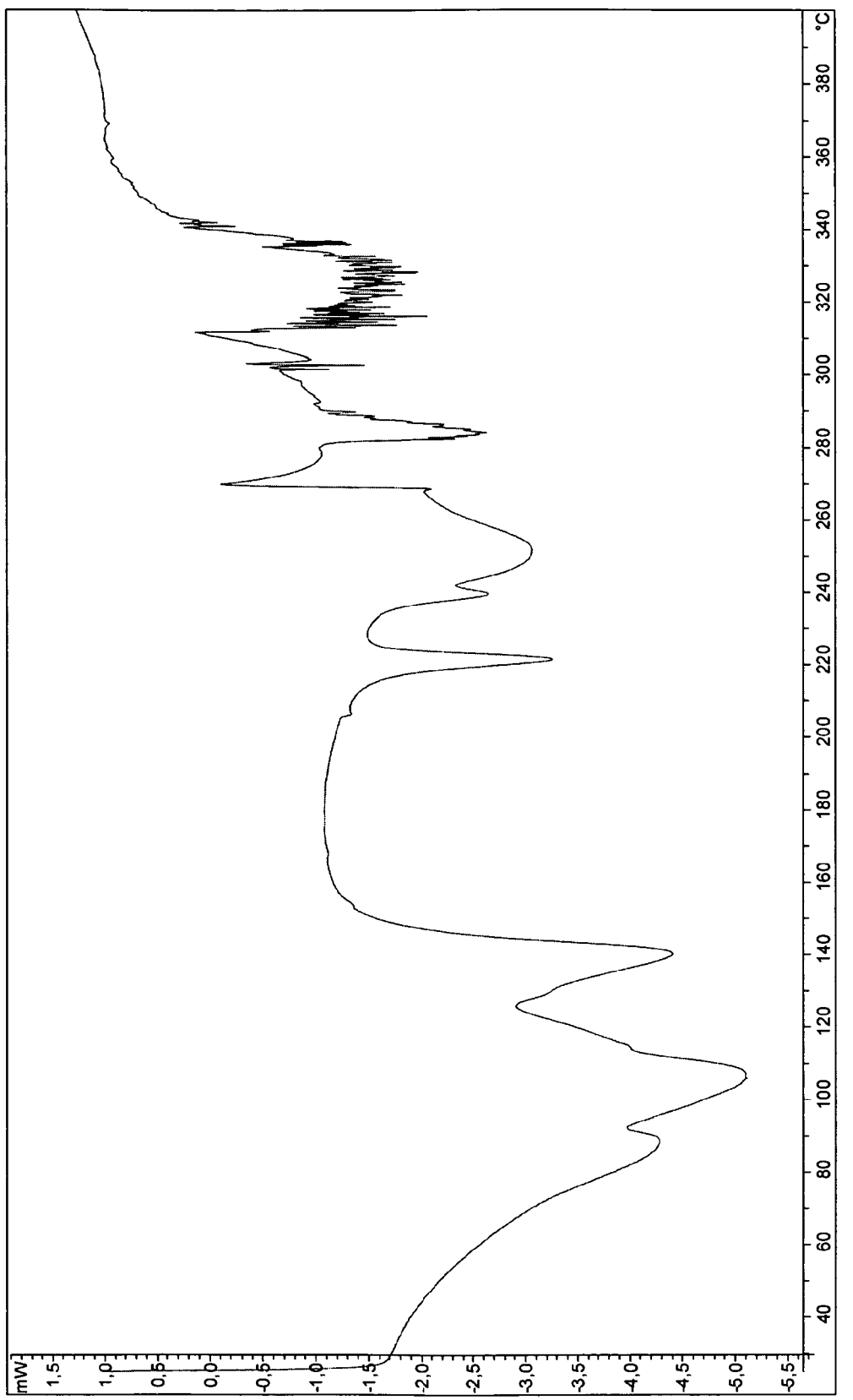
FIG. 23 depicts the DSC measurements of crystalline form S3.
Figure 24:
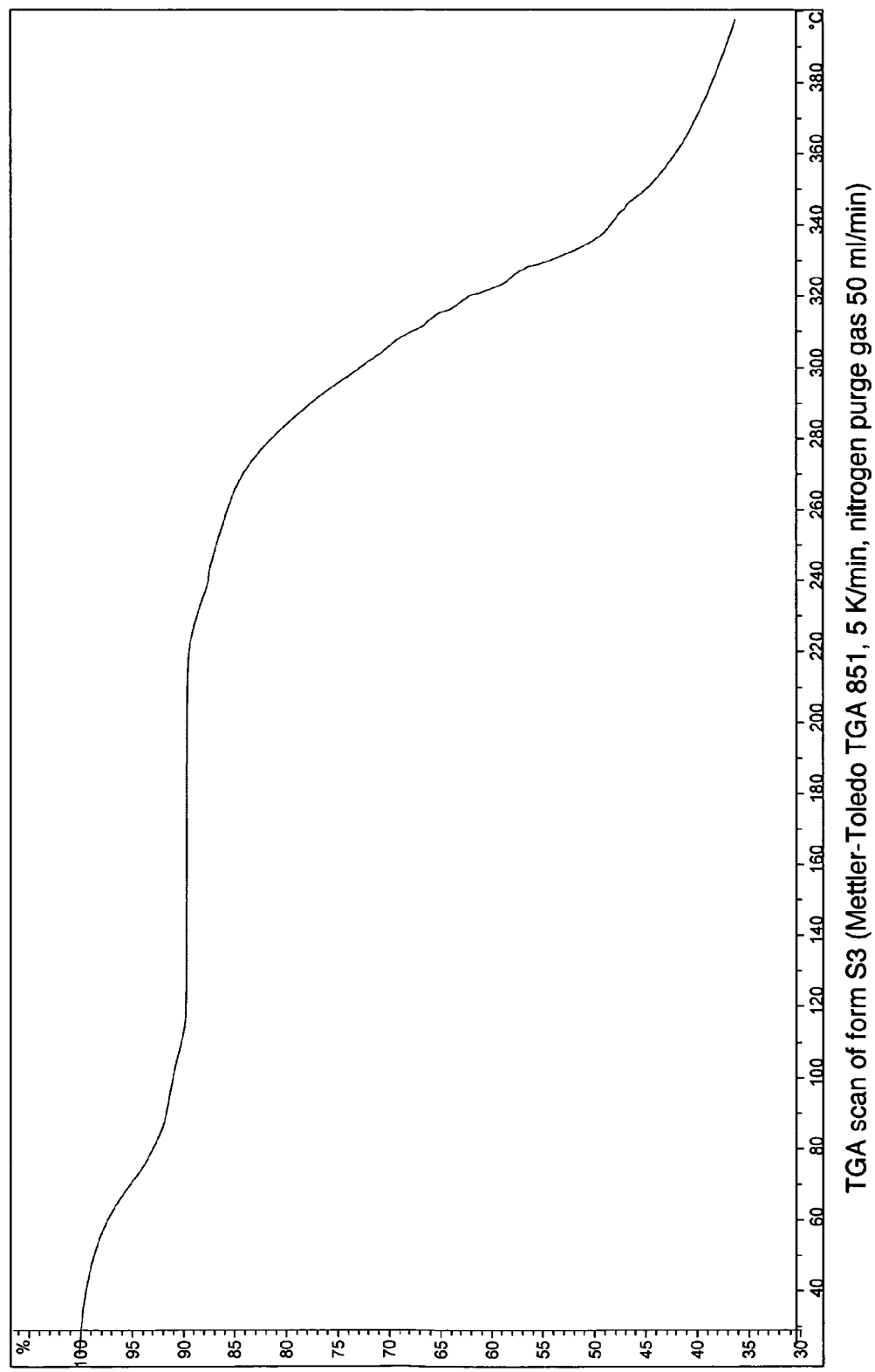
FIG. 24 depicts the TGA measurements of crystalline form S3.

The DSC and TGA measurements showing the thermal analysis (Mettler-Toledo DSC 821, 5 K/min, nitrogen purge gas 50 ml/min; Mettler-Toledo TGA 851, 5 K/min, nitrogen purge gas 50 ml/min) and the melting/decomposition temperature given above is shown in FIG. 23 and FIG. 24.

Preferably, the tetrasolvates according to the invention, more preferably the tetrahydrates according to the invention and especially the crystalline form S3 can be characterised, alternatively or additionally, by Powder X-Ray Diffraction and more preferably by the Powder X-Ray Diffraction pattern comprising one or more of the Powder X-ray peaks given below, more preferably comprising 3 or more of the Powder X-ray peaks given below, even more preferably 6 or more of the Powder X-ray peaks given below, and especially comprising all of the of the Powder X-ray peaks given below:

| a) | | | | | |
|---|---|---|---|---|---|
| | D ± 0.1 | °2θ (Cu—Kα$_1$ radiation) ± | Miller indices | | |
| No. | [Å] | 0.1° | h | k | l |
| 1 | 12.98 | 6.8 | 0 | 2 | 0 |
| 2 | 12.25 | 7.2 | 0 | 1 | 1 |
| 5 | 7.50 | 11.8 | 1 | 1 | 1 |
| 11 | 4.88 | 18.2 | 0 | 5 | 1 |
| 12 | 4.67 | 19.0 | 2 | 0 | 1 |
| 13 | 4.49 | 19.8 | 2 | 1 | 0 |
| 14 | 4.11 | 21.6 | 1 | 3 | 1 |
| 15 | 3.99 | 22.3 | 2 | 1 | 3 | or more preferably

| b) | | | | | |
|---|---|---|---|---|---|
| | D ± 0.1 | °2θ (Cu—Kα$_1$ radiation) ± | Miller indices | | |
| No. | [Å] | 0.1° | h | k | l |
| 1 | 12.98 | 6.8 | 0 | 2 | 0 |
| 2 | 12.25 | 7.2 | 0 | 1 | 1 |
| 5 | 7.50 | 11.8 | 1 | 1 | 1 |
| 11 | 4.88 | 18.3 | 0 | 5 | 1 |
| 12 | 4.67 | 19.1 | 2 | 1 | 0 |
| 13 | 4.49 | 19.8 | 2 | 0 | 1 |
| 14 | 4.11 | 21.7 | 1 | 1 | 3 |
| 15 | 3.99 | 22.4 | 2 | 3 | 1 |

Preferably, the tetrasolvates according to the invention, more preferably the tetrahydrates according to the invention and especially the crystalline form S3 can be characterised, alternatively or additionally, by Powder X-Ray Diffraction more preferably by the Powder X-Ray Diffraction pattern comprising one or more of the Powder X-ray peaks given below, more preferably comprising 9 or more of the Powder X-ray peaks given below, even more preferably 12 or more of the Powder X-ray peaks given below, and especially comprising all of the of the Powder X-ray peaks given below:

a)

| No. | D [Å] | °2θ (Cu—Kα₁ radiation) ± 0.1° | Miller indices h | k | l |
|---|---|---|---|---|---|
| 1 | 12.98 | 6.8 | 0 | 2 | 0 |
| 2 | 12.25 | 7.2 | 0 | 1 | 1 |
| 3 | 8.91 | 9.9 | 1 | 0 | 1 |
| 4 | 7.83 | 11.3 | 1 | 1 | 0 |
| 5 | 7.50 | 11.8 | 1 | 1 | 1 |
| 6 | 7.34 | 12.1 | 0 | 3 | 1 |
| 7 | 6.94 | 12.7 | 0 | 0 | 2 |
| 9 | 6.13 | 14.5 | 0 | 2 | 2 |
| 10 | 5.15 | 17.2 | 1 | 2 | 2 |
| 11 | 4.88 | 18.2 | 0 | 5 | 1 |
| 12 | 4.67 | 19.0 | 2 | 0 | 1 |
| 13 | 4.49 | 19.8 | 2 | 1 | 0 |
| 14 | 4.11 | 21.6 | 1 | 3 | 1 |
| 15 | 3.99 | 22.3 | 2 | 1 | 3 | or more preferably b)

| No. | D [Å] | °2θ (Cu—Kα₁ radiation) ± 0.1° | Miller indices h | k | l |
|---|---|---|---|---|---|
| 1 | 12.98 | 6.8 | 0 | 2 | 0 |
| 2 | 12.25 | 7.2 | 0 | 1 | 1 |
| 3 | 8.91 | 9.9 | 1 | 1 | 0 |
| 4 | 7.83 | 11.3 | 1 | 0 | 1 |
| 5 | 7.50 | 11.8 | 1 | 1 | 1 |
| 6 | 7.34 | 12.1 | 0 | 3 | 1 |
| 7 | 6.94 | 12.8 | 0 | 0 | 2 |
| 9 | 6.13 | 14.5 | 0 | 2 | 2 |
| 10 | 5.15 | 17.3 | 1 | 2 | 2 |
| 11 | 4.88 | 18.3 | 0 | 5 | 1 |
| 12 | 4.67 | 19.1 | 2 | 1 | 0 |
| 13 | 4.49 | 19.8 | 2 | 0 | 1 |
| 14 | 4.11 | 21.7 | 1 | 1 | 3 |
| 15 | 3.99 | 22.4 | 2 | 3 | 1 |

Preferably, the tetrasolvates according to the invention, more preferably the tetrahydrates according to the invention and especially the crystalline form S3 can be characterised, alternatively or additionally, by Powder X-Ray Diffraction and more preferably by the Powder X-Ray Diffraction pattern comprising one or more of the Powder X-ray peaks given below, more preferably comprising 10 or more of the Powder X-ray peaks given below, even more preferably 13 or more of the Powder X-ray peaks given below, and especially comprising all of the of the Powder X-ray peaks given below:

a)

| No. | D ± 0.1 [Å] | °2θ (Cu—Kα₁ radiation) ± 0.1° | Miller indices h | k | l |
|---|---|---|---|---|---|
| 1 | 12.98 | 6.8 | 0 | 2 | 0 |
| 2 | 12.25 | 7.2 | 0 | 1 | 1 |
| 3 | 8.91 | 9.9 | 1 | 0 | 1 |
| 4 | 7.83 | 11.3 | 1 | 1 | 0 |
| 5 | 7.50 | 11.8 | 1 | 1 | 1 |
| 6 | 7.34 | 12.1 | 0 | 3 | 1 |
| 7 | 6.94 | 12.7 | 0 | 0 | 2 |
| 8 | 6.50 | 13.6 | 0 | 4 | 0 |
| 9 | 6.13 | 14.5 | 0 | 2 | 2 |
| 10 | 5.15 | 17.2 | 1 | 2 | 2 |
| 11 | 4.88 | 18.2 | 0 | 5 | 1 |
| 12 | 4.67 | 19.0 | 2 | 0 | 1 |
| 13 | 4.49 | 19.8 | 2 | 1 | 0 |
| 14 | 4.11 | 21.6 | 1 | 3 | 1 |
| 15 | 3.99 | 22.3 | 2 | 1 | 3 | or more preferably b)

| No. | D ± 0.1 [Å] | °2θ (Cu—Kα₁ radiation) ± 0.1° | Miller indices h | k | l |
|---|---|---|---|---|---|
| 1 | 12.98 | 6.8 | 0 | 2 | 0 |
| 2 | 12.25 | 7.2 | 0 | 1 | 1 |
| 3 | 8.91 | 9.9 | 1 | 1 | 0 |
| 4 | 7.83 | 11.3 | 1 | 0 | 1 |
| 5 | 7.50 | 11.8 | 1 | 1 | 1 |
| 6 | 7.34 | 12.1 | 0 | 3 | 1 |
| 7 | 6.94 | 12.8 | 0 | 0 | 2 |
| 8 | 6.50 | 13.7 | 0 | 4 | 0 |
| 9 | 6.13 | 14.5 | 0 | 2 | 2 |
| 10 | 5.15 | 17.3 | 1 | 2 | 2 |
| 11 | 4.88 | 18.3 | 0 | 5 | 1 |
| 12 | 4.67 | 19.1 | 2 | 1 | 0 |
| 13 | 4.49 | 19.8 | 2 | 0 | 1 |
| 14 | 4.11 | 21.7 | 1 | 1 | 3 |
| 15 | 3.99 | 22.4 | 2 | 3 | 1 |

Figure 25:
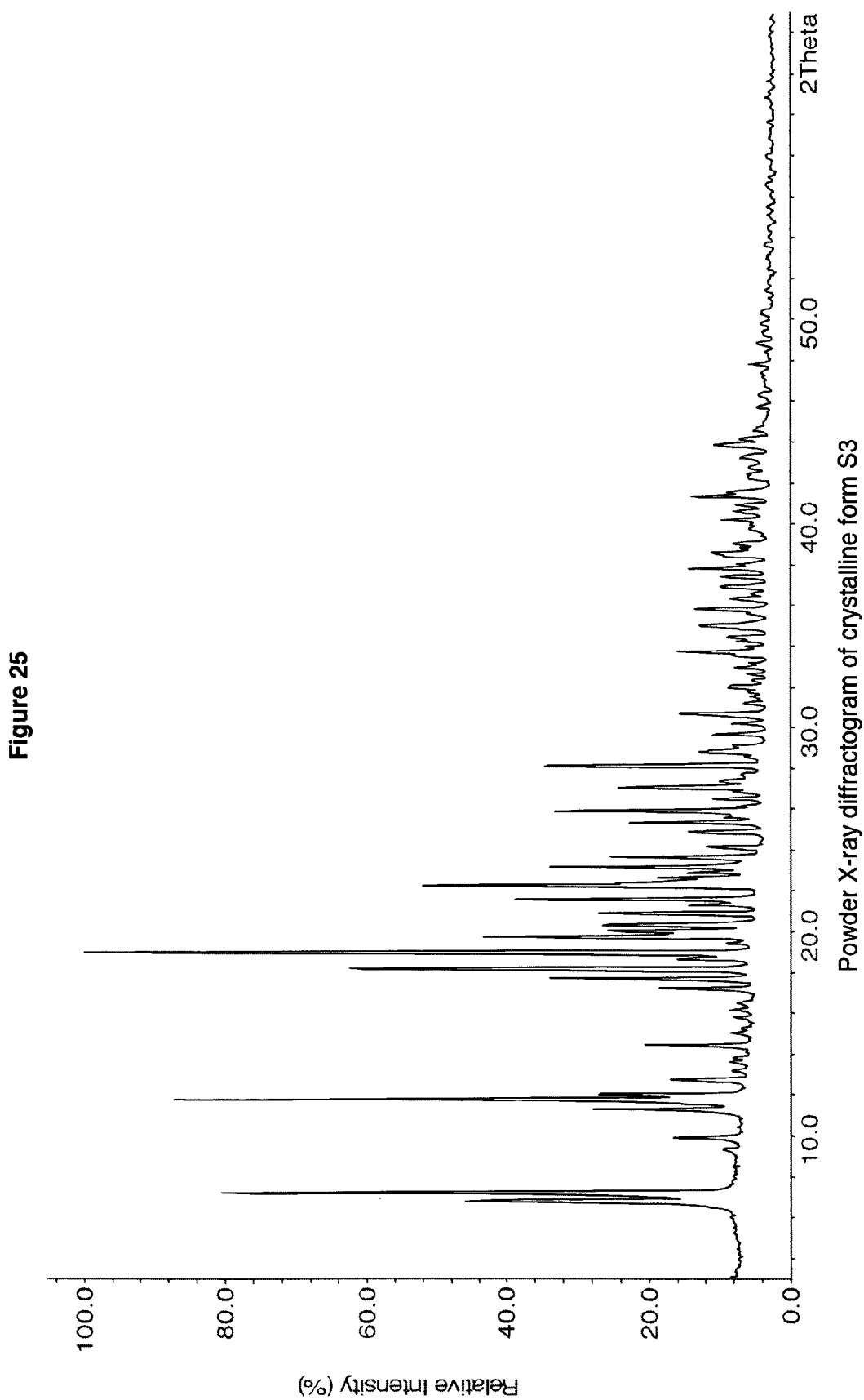
FIG. 25 depicts the powder x-ray diffractogram of crystalline form S3.

FIG. 25 shows the Powder X-ray diffractogram of crystalline form S3

The Powder X-Ray Diffraction and more preferably the Powder X-Ray Diffraction pattern is preferably performed or determined as described herein and especially performed or determined by standard techniques as described in the European Pharmacopeia 6$^{th}$ Edition chapter 2.9.33, and is even more preferably obtained with the parameters Cu—Kα$_1$ radiation and/or λ=1.5406 Å, preferably on a Stoe StadiP 611 KL diffractometer.

Preferably, the tetrasolvates according to the invention, more preferably the tetrahydrates according to the invention and especially the crystalline form S3 can be characterised, alternatively or additionally, by Single Crystal X-Ray Structure Data, for example Single Crystal X-Ray Structure Data obtained on a diffractometer preferably equipped with a graphite monochromator and CCD Detector, preferably using Mo K$_\alpha$ radiation, preferably at a temperature of 298 K±5 K, and even more preferably on a XCalibur diffractometer from Oxford Diffraction equipped with graphite monochromator and CCD Detector using Mo K$_\alpha$ radiation at about 298 K.

According to the Single Crystal X-Ray Structure Data obtained, the tetrahydrates of the compound of formula I according to the invention and especially the crystalline form S3 crystallises in the orthorhombic space group P 2$_1$ 2$_1$ 2$_1$ with the lattice parameters a=9.6 Å, b=25.9 Å, c=13.9 Å (±0.1 Å) and the unit cell volume is preferably is 3396 (±10) Å$^3$ From the single crystal structure it is obvious that form S3 represents a tetrasolvate and more specifically a tetrahydrate.

Figure 26:
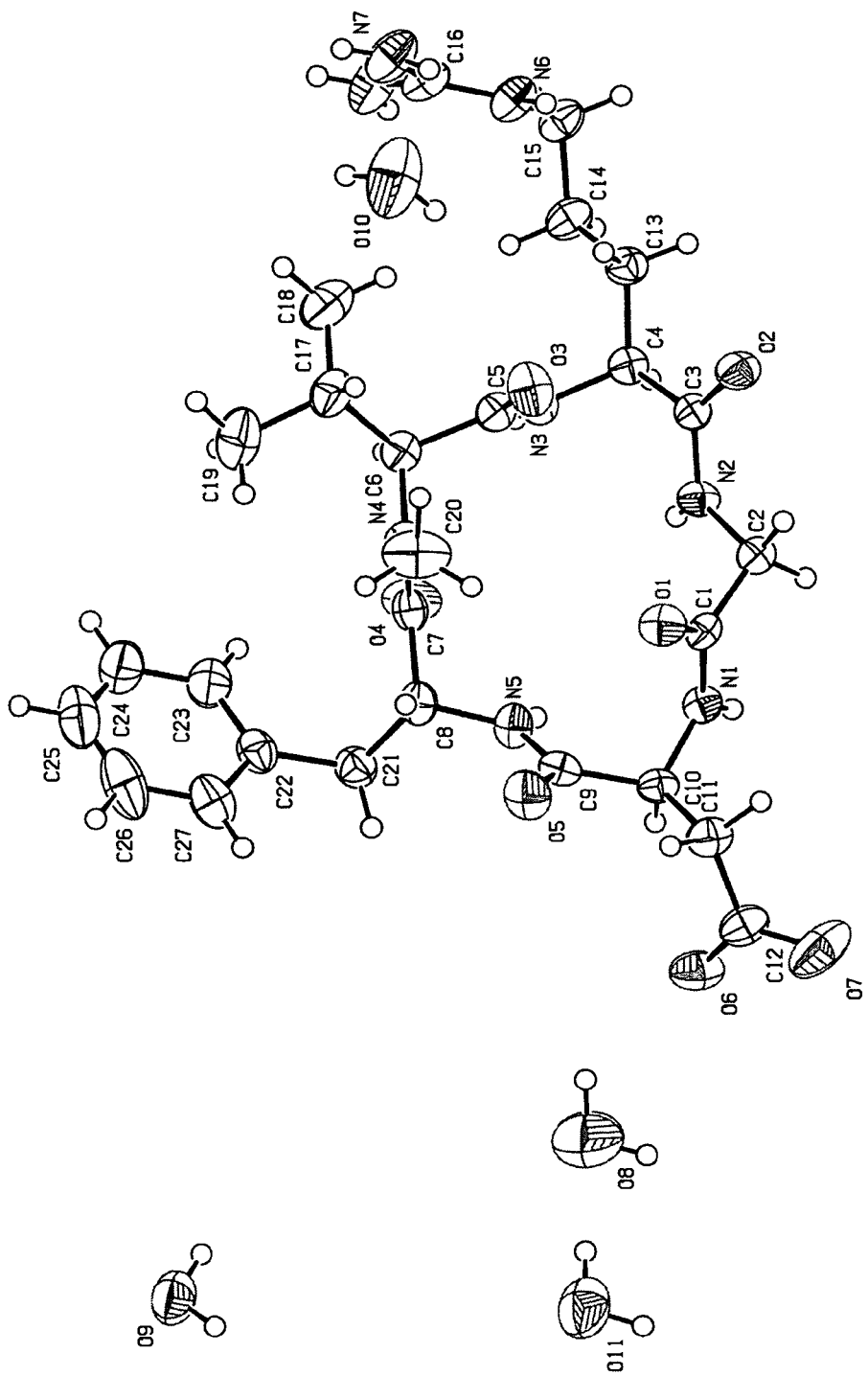
FIG. 26 depicts the single crystal structure of crystalline form S3.
Figure 26A:
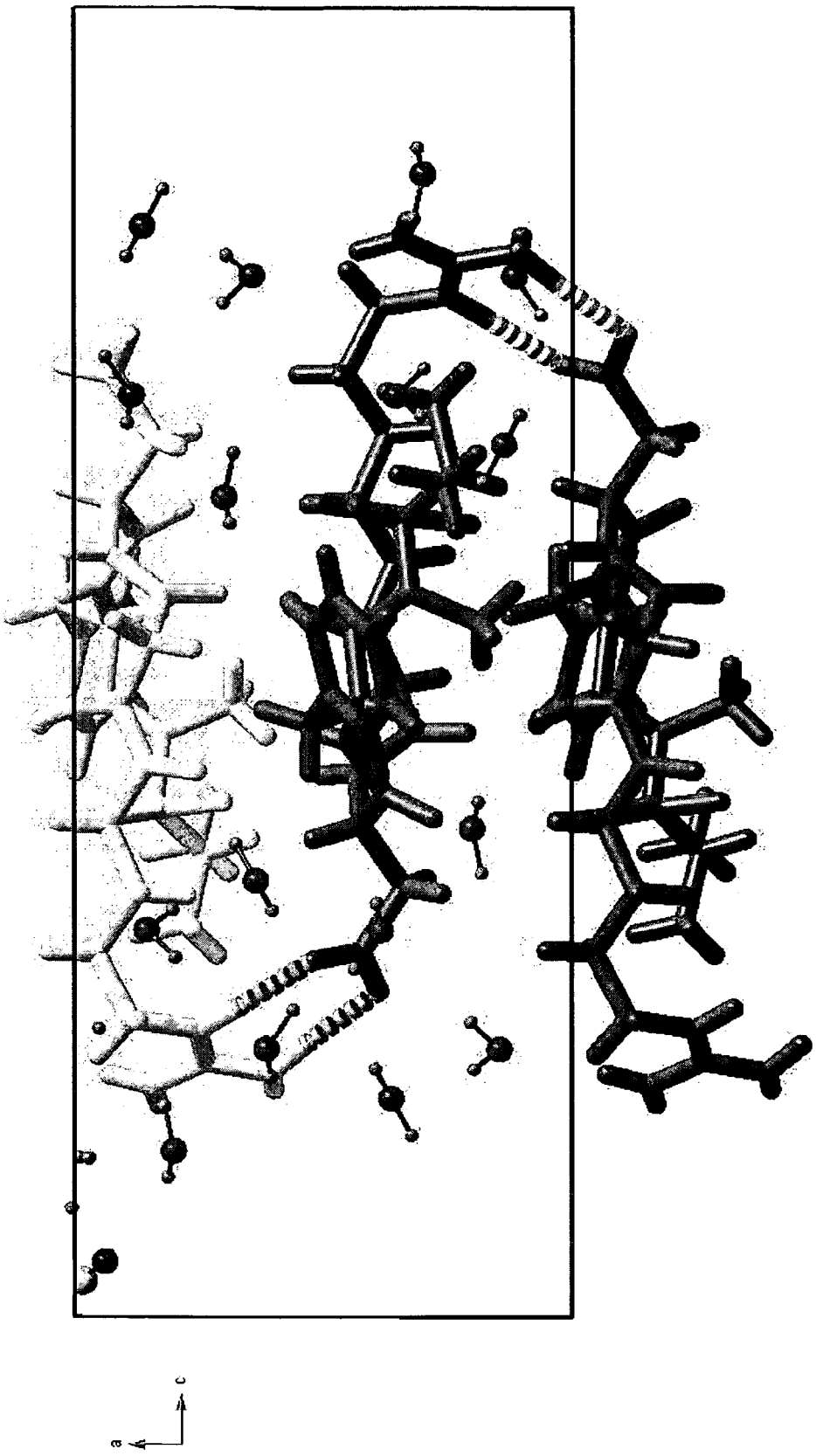
FIGS. 26a-26c depict additional structural information of the single crystal structure of crystalline form S3.
Figure 26B:
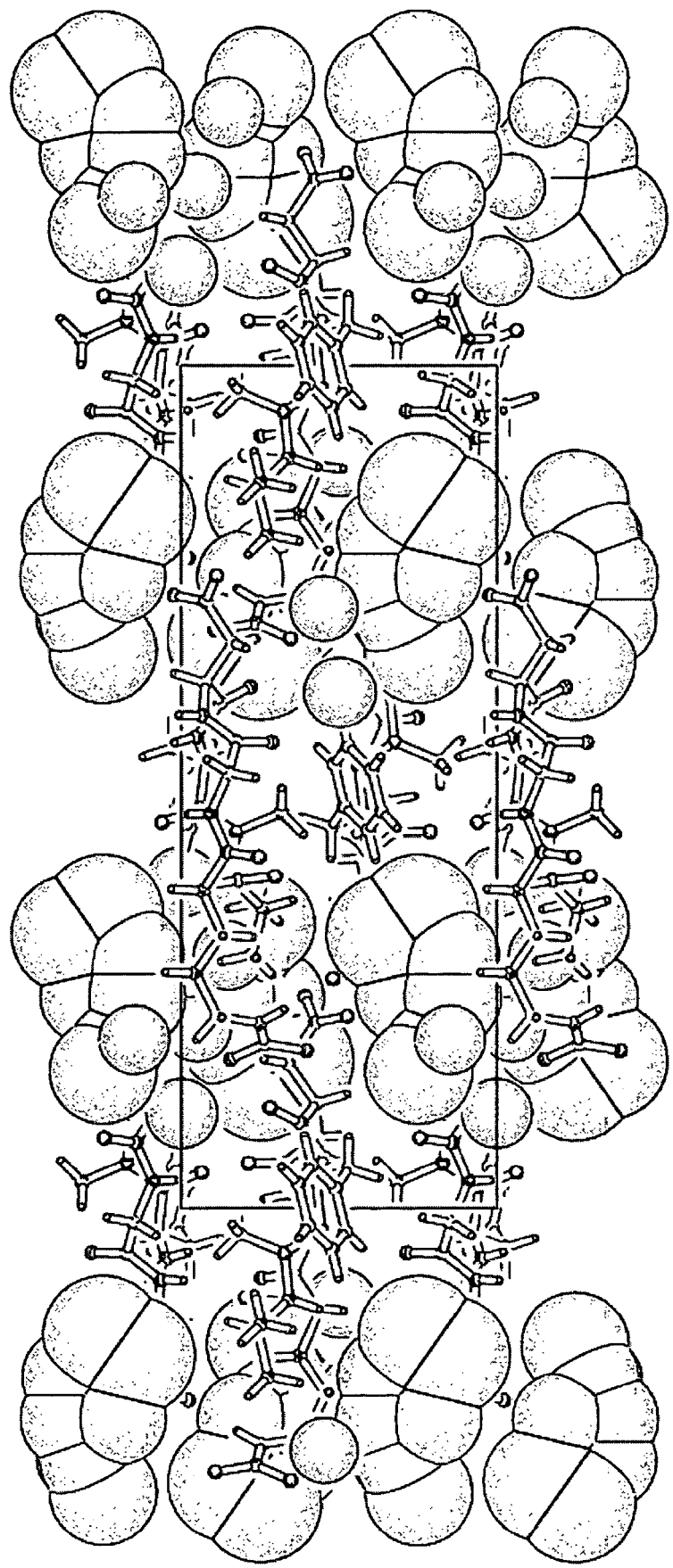
Figure 26C:
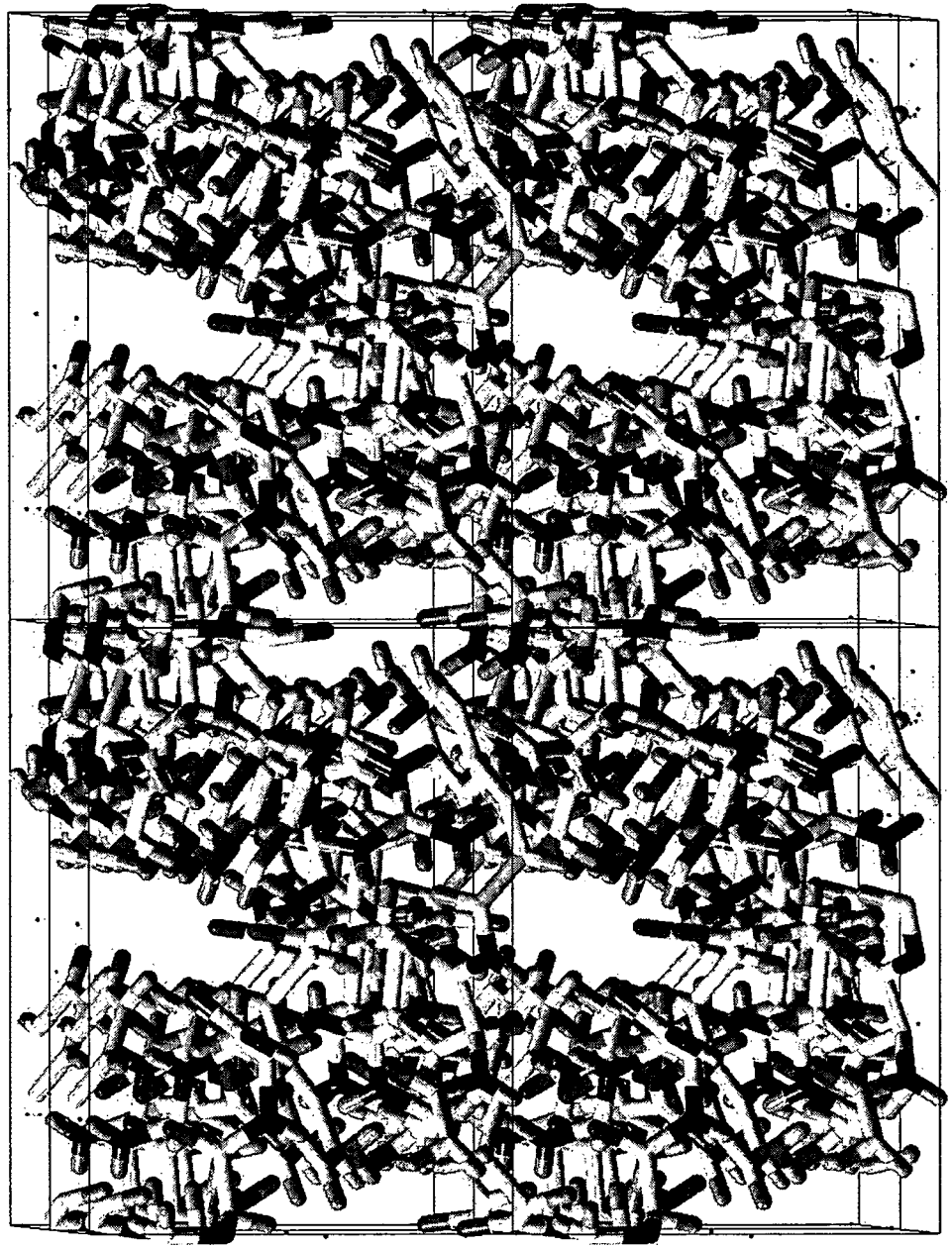

The Single Crystal X-Ray Structure is depicted in FIG. 26. Additional structural Information based on said Single Crystal X-Ray Structure data is given in FIGS. 26a, 26b and 26c.

Preferably, the tetrasolvates according to the invention, more preferably the tetrahydrates according to the invention and especially the crystalline form S3 can be characterised, alternatively or additionally, by the infrared-spectroscopy data comprising one or more of the band positions (±2 cm$^{-1}$) given below, more preferably comprising 3 or more of the band positions (±2 cm$^{-1}$) given below, even more preferably comprising 6 or more of the band positions (±2 cm$^{-1}$) given below, and especially comprising all the band positions (±2 cm$^{-1}$) given below, preferably together with the relative intensities given in brackets:
3319 cm$^{-1}$ (s), 3067 cm$^{-1}$ (s), 2966 cm$^{-1}$ (s), 1668 cm$^{-1}$ (s), 1541 cm$^{-1}$ (s), 1395 cm$^{-1}$ (s), 704 cm$^{-1}$ (m)

More preferably, the tetrasolvates according to the invention, more preferably the tetrahydrates according to the invention and especially the crystalline form S3 can be characterised, alternatively or additionally, by the infrared-spectroscopy data comprising one or more of the band positions (±2 cm$^{-1}$) given below, more preferably comprising 6 or more of the band positions (±2 cm$^{-1}$) given below, even more preferably comprising 9 or more of the band positions (±2 cm$^{-1}$) given below, and especially comprising all the band positions (±2 cm$^{-1}$) given below, preferably together with the relative intensities given in brackets:
3428 cm$^{-1}$ (s), 3319 cm$^{-1}$ (s), 3067 cm$^{-1}$ (s), 2966 cm$^{-1}$ (s), 2874 cm$^{-1}$ (m), 1668 cm$^{-1}$ (s), 1541 cm$^{-1}$ (s), 1455 cm$^{-1}$ (s), 1395 cm$^{-1}$ (s), 1232 cm$^{-1}$ (m), 704 cm$^{-1}$ (m)

The relative intensities given in brackets are preferably defined as follows: *"s"=strong (transmittance preferably ≤50%), "m"=medium (preferably 50%<transmittance≤70%), "w"=weak (transmittance preferably >70%)

The IR or FT-IR spectrum is preferably obtained using a KBr pellet as sample preparation technique.

The IR-spectroscopy data is preferably obtained by FT-IR-spectroscopy, The IR-spectroscopy data or FT-IR-spectroscopy data is preferably obtained by standard techniques as described in the European Pharmacopeia 6$^{th}$ Edition chapter 2.02.24. For the measurement of the FT-IR-spectra, preferably a Bruker Vector 22 spectrometer is used. FT-IR spectra are preferably base-line corrected, preferably using Bruker OPUS software.

Figure 27:
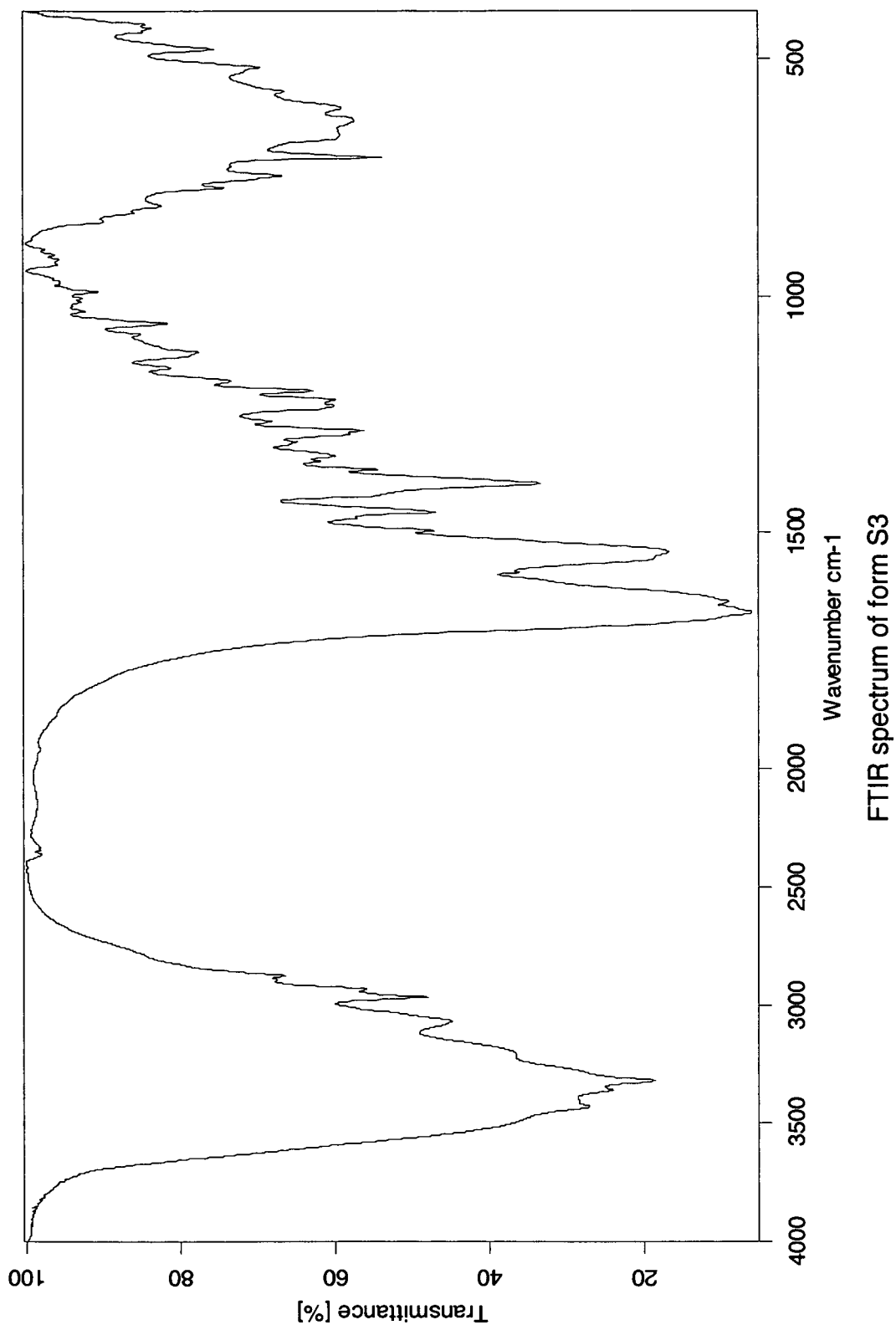
FIG. 27 depicts the FT-IR spectrum of crystalline form S3.

The FT-IR spectra of the tetrasolvates according to the invention, more preferably the tetrahydrates according to the invention and especially the crystalline form S3 is given in FIG. 27.

Preferably, the tetrasolvates according to the invention, more preferably the tetrahydrates according to the invention and especially the crystalline form S3 can be characterised, alternatively or additionally, by the Raman-spectroscopy data comprising one or more of the band positions (±2 cm$^{-1}$) given below, more preferably comprising 4 or more of the band positions (±2 cm$^{-1}$) given below, even more preferably comprising 7 or more of the band positions (±2 cm$^{-1}$) given below, and especially comprising all the band positions (±2 cm$^{-1}$) given below, preferably together with the relative intensities given in brackets:
3069 cm$^{-1}$ (m), 2931 cm$^{-1}$ (s), 1666 cm$^{-1}$ (m), 1607 cm$^{-1}$ (w), 1443 cm$^{-1}$ (w), 1339 cm$^{-1}$ (w), 1205 cm$^{-1}$ (w), 1004 cm$^{-1}$ (s), 911 cm$^{-1}$ (m).

More preferably, the tetrasolvates according to the invention, more preferably the tetrahydrates according to the invention and especially the crystalline form S3 can be characterised, alternatively or additionally, by the Raman-spectroscopy data comprising one or more of the and positions (±2 cm$^{-1}$) given below, more preferably comprising 9 or more of the band positions (±2 cm$^{-1}$) given below, even more preferably comprising 12 or more of the band positions (±2 cm$^{-1}$) given below, and especially comprising all the band positions (±2 cm$^{-1}$) given below, preferably together with the relative intensities given in brackets:
3069 cm$^{-1}$ (m), 2931 cm$^{-1}$ (s), 1666 cm$^{-1}$ (m), 1607 cm$^{-1}$ (w), 1585 cm$^{-1}$ (w), 1443 cm$^{-1}$ (w), 1339 cm$^{-1}$ (w), 1205 cm$^{-1}$ (w), 1122 cm$^{-1}$ (w), 1033 cm$^{-1}$ (w), 1004 cm$^{-1}$ (s), 936 cm$^{-1}$ (w), 911 cm$^{-1}$ (m), 825 cm$^{-1}$ (w), 624 cm$^{-1}$ (w), 519 cm$^{-1}$ (w), The relative intensities given in brackets are preferably defined as follows: "s"=strong (relative Raman intensity preferably ≥0.04), "m"=medium (preferably 0.04>relative Raman intensity≥0.02), "w"=weak (relative Raman intensity preferably <0.02)

The Raman or FT-Raman spectrum is preferably obtained using Aluminium-cups as sample holders for the respective solid material.

The Raman-spectroscopy data is preferably obtained by FT-Raman-spectroscopy, The Raman-spectroscopy data or FT-Raman-spectroscopy data is preferably obtained by standard techniques as described in the European Pharmacopeia 6$^{th}$ Edition chapter 2.02.24 and/or 2.02.48. For the measurement of the FT-Raman-spectra, preferably a Bruker RFS 100 spectrometer is used. FT-Raman spectra are preferably base-line corrected, preferably using Bruker OPUS software.

Figure 28:
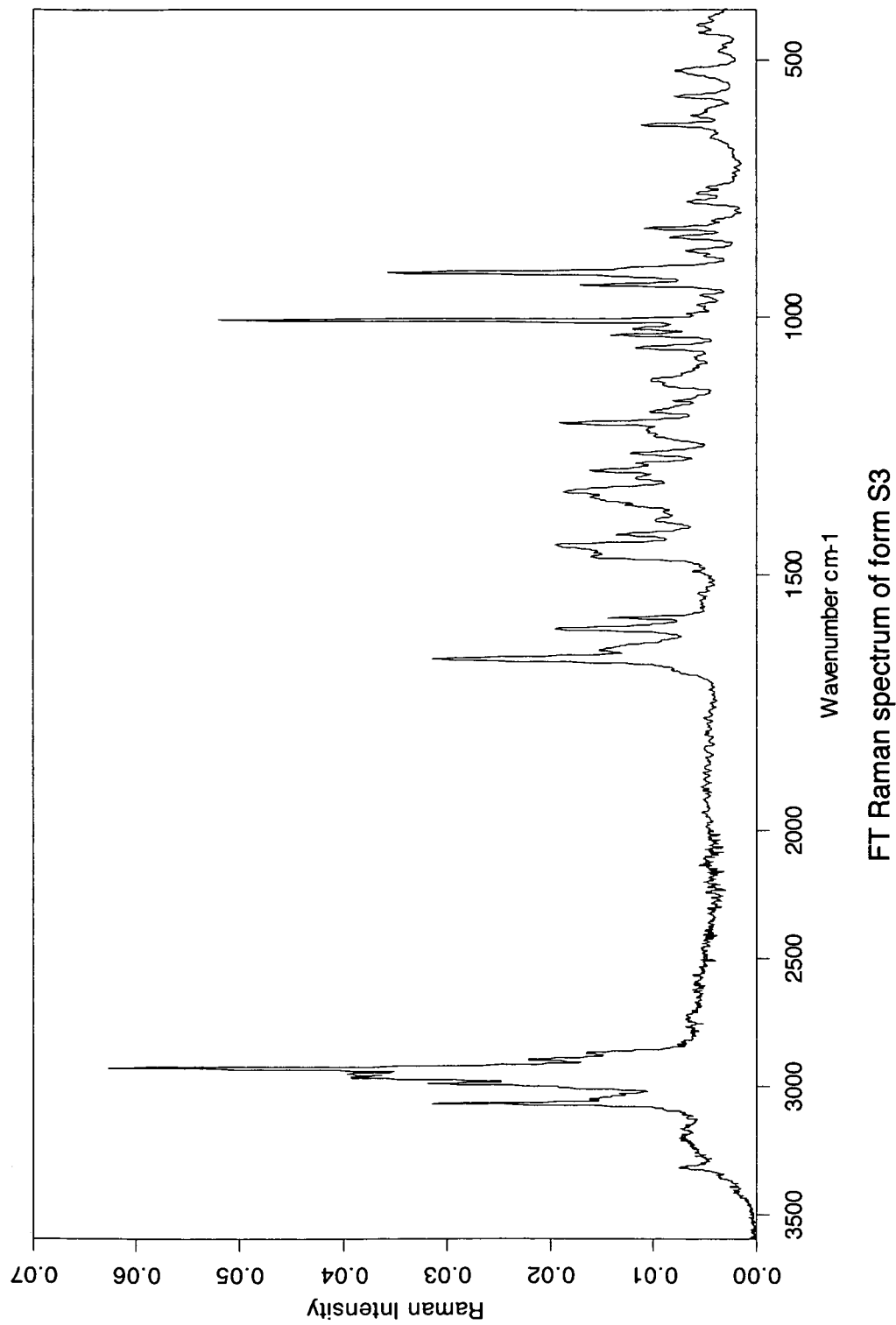
FIG. 28 depicts the FT-Raman spectrum of crystalline form S3.

The FT-Raman spectra of the tetrasolvates according to the invention and especially the crystalline form S3 is given in FIG. 28.

Preferably, the tetrasolvates according to the invention, more preferably the tetrahydrates according to the invention and especially the crystalline form S3 can be characterised, alternatively or additionally, by dynamic vapour sorption experiments. The results can be obtained by standard techniques as described in Rolf Hilfiker, 'Polymorphism in the Pharmaceutical Industry', Wiley-VCH. Weinheim 2006 (Chapter 9: Water Vapour Sorption, and references therein).

Figure 29:
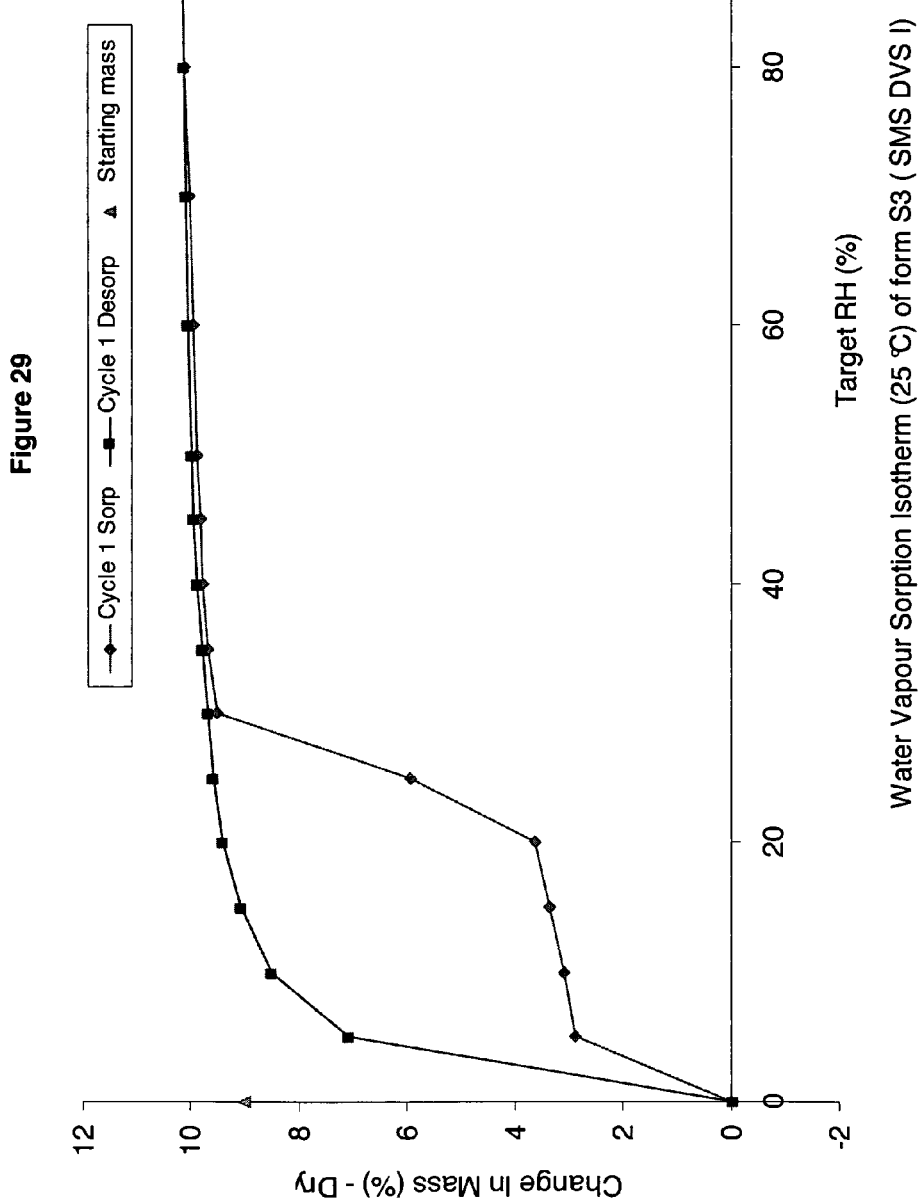
FIG. 29 depicts the water vapour sorption isotherm of crystalline form S3.

The Water Vapour Sorption behaviour shows a loss of water molecules (ca. 9% by weight) within the initial drying step (0% relative humidity (rh)). During the water adsorption cycle an assembly of water molecules in the lattice can be shown (ca. 10% by weight) at elevated rh. In the second desorption cycle, a loss of this amount of water can be shown. The Water Vapour Sorption isotherm (25° C.) of form S3 is shown in FIG. 29.

Overall, the thermal analysis data given herein confirms the tetrahydrate structure, with complete dehydration observed at elevated temperature (for the tetrahydrate the calculated water content is 10.9 wt %) in the TGA. Water vapour sorption data show that even under dry conditions (0% rh) at 25° C., only ~9 wt % water are split-off, showing that preferably no complete dehydration of the structure occurs. Water vapour sorption isotherm (25° C.) of crystalline form S3 (SMS DVS Intrinsic) is given in FIG. 29.

Surprisingly, it has been found that the water molecules within the hydrates according to the invention and especially the water molecules within the tetrahydrates according to the invention can be substituted, partially or totally, by alcohol molecules, preferably by alcohol molecules selected from the group consisting of monools, diols or triols having 1 to 6 carbon atoms, more preferably monools having 1 to 4 carbon atoms and especially monools selected from the group consisting of methanol and ethanol, and mixtures thereof.

Experimental methods, such as dynamic vapour sorption/desorption experiments, single crystal X-Ray experiments and/or powder x-ray experiments show that starting e.g. from the tetrahydrate characterized as crystalline form S3, the water molecules of said tetrahydrate can be partly and/or about totally removed from said tetrahydrate and/or be substituted by methanol and/or ethanol.

For example, dynamic vapour sorption/desorption experiments, preferably using vapours of organic solvents and/or water, preferably vapours of organic solvents selected from one or more alcohols preferably alcohols as defined herein, and/or water and especially vapours of methanol, ethanol and/water, show that the water molecules from said tetrahydrate can continuously be substituted by alcohol molecules and especially methanol and/or ethanol molecules, potentially until a tetra alcohol solvate or a mixed alcohol-water solvate or tetrasolvate is formed.

Figure 30:
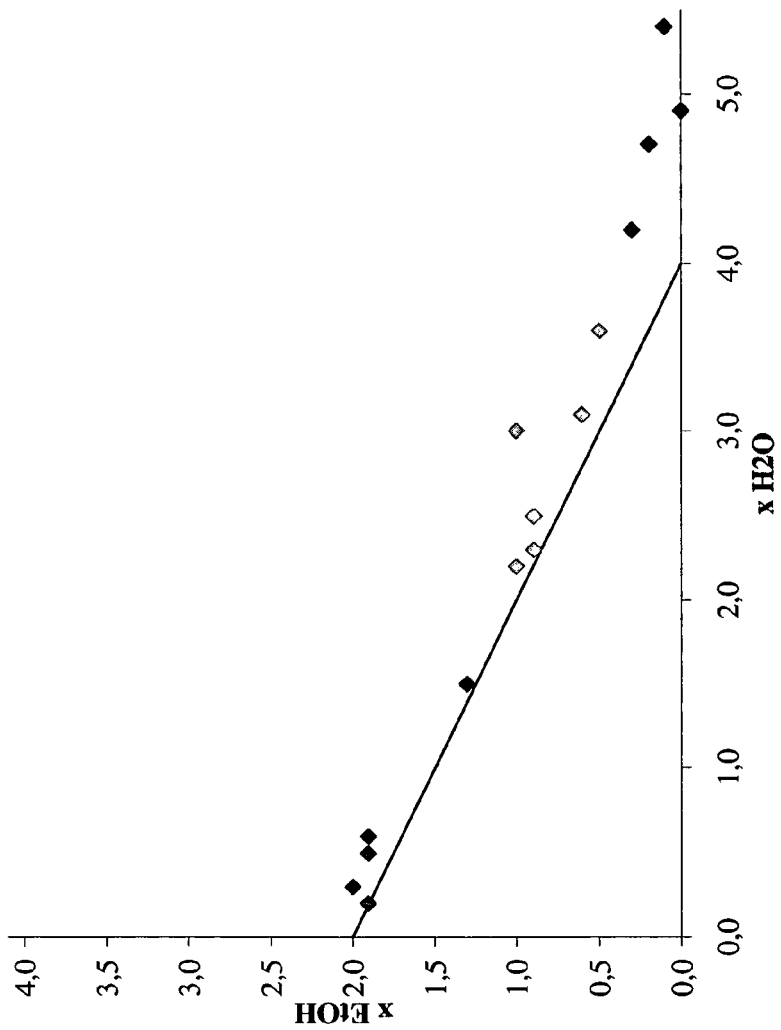
FIG. 30 depicts stoichiometries for quantification of ethanol.

As another example, conditioning of
a) amorphous material of the compound according to formula I or
b) hydrate forms
under mixed water-alcohol atmospheres—preferably water-ethanol atmospheres—representing different water and alcohol partial pressures yielded in both cases crystalline solvates exhibiting different stoichiometries with up to 4 molecules of water or up to 2 molecules of ethanol per molecule of the compound according to formula I, e.g. the tetrahydrate S3 (4 molecules of water) or the diethanolate S2 (2 Molecules of ethanol, see e.g. FIG. 31)), depending on the respective conditions used. Stoichiometries as determined by Karl-Fischer titration for quantification of water and HS-GC for quantification of ethanol are depicted in FIG. 30. In the diagram also points representing stochiometries with more than 4 molecules of water per molecule of the compound according to formula I are depicted. As there is no space for more than 4 molecules of water in the crystal lattice of the tetrahydrates, excess amounts of more than 4 molecules of water represent adsorbed moisture.

The results (see also Example 13) show that there is a floating transition from the hydrate form S3 into the mixed water-ethanol or waterless ethanol solvate form S2 with increasing ethanol vapour pressure. All solvates (including the hydrates) have similar lattice parameters, which only slightly increase with the assembly of ethanol molecules As still another example, conditioning of amorphous material of the compound according to formula I or hydrate forms under methanol atmosphere yielded crystalline solvates with 2 molecules methanol per molecule of the compound according to formula I.

Thus, crystalline forms that can be characterised as tetrasolvates are obtainable, which have a solvent content between up to approximately 100% of water (referring to 4 molecules of water per molecule of the compound according to formula I, i.e. referring a tetrahydrate) and a solvent content of up to approximately 100% of alcohol (referring to 4 molecules of alcohol per molecule of the compound according to formula I, i.e. referring a tetraalcoholate) and preferably the intermediates in between.

The results are further discussed above and/or below and especially discussed in the Tables 1 and 2 given below. For example, metastable crystalline solvates being mixed Dihydrate-dialcoholates (referring to 2 molecules of water and 2 molecules of alcohol per molecule of the compound according to formula I), later in detail characterized as Dihydrate-dimethanolate and crystalline form S1 and as Dihydrate-diethanolate and crystalline form S2, respectively, can be obtained and are discussed in detail above and/or below. These stoichiometries were derived and/or extrapolated from the herein described Dynamic Vapor Sorption experiments. New X-ray experiments prove that metastable crystalline solvates also can be present as mixed Dihydrate-alcoholates or more specifically Dihydrate-monoalcoholates (referring to 2 molecules of water and 1 molecule of alcohol per molecule of the compound according to formula I) as further manifestations of these non-stoichiometric class of pseudopolymorphs, later in detail characterized as Dihydrate-methanolate, Dihydrate-monomethanolate and/or another manifestation of crystalline form S1, and as Dihydrate-ethanolate, Dihydrate-monoethanolate and/or another manifestation of crystalline form S2, respectively, can be obtained and are discussed in detail above and/or below.

Special reference in this regard is given to the Tables 1 and 2 given below and the paragraphs relating thereto.

The following tables show the respective calculated gravimetric water and/or methanol contents for tetrasolvates ranging from tetrahydrate to tetraalcoholate; in this calculation, integer steps in the solvate stoichiometry have been used based on one molecule of the compound according to formula I, and in total four molecules of the respective solvent or solvent mixture in said tetrasolvates. This can preferably be expressed by the following formulae:

[cyclo-(Arg-Gly-Asp-DPhe-NMe-Val)].[Alcohol]$_x$.[H$_2$O]$_{(y)}$ (with $0 \le x \le 4$ and $0 \le y \le 4$), more specifically:
[cyclo-(Arg-Gly-Asp-DPhe-NMe-Val)].[Alcohol]$_x$.[H$_2$O]$_{(4-x)}$ with $0 \le x \le 4$) (for the interconversion between the tetrahydrates and the tetraalcoholates)
or
[cyclo-(Arg-Gly-Asp-DPhe-NMe-Val)].[Alcohol]$_x$.[H$_2$O]$_{(y)}$ with $0 \le y \le 4$ and $x \le 2-0.5*y$ and $x \le 1$) (for the interconversion between the tetrahydrates and the Dihydrate-alcoholates or more specifically Dihydrate-monoalcoholates). ("*"=multiplication sign)

TABLE 1

(water/methanol exchange)

| Methanol equivalents [x] | Water equivalents [y] | molar mass [g/mol] | gravimetric methanol content [%] | gravimetric water content [%] | molar mass of solvate relative to tetrahydrate [%] |
|---|---|---|---|---|---|
| 0 | 4 | 660.75 | 0.0 | 10.9 | 100.0% |
| 1 | 3 | 674.77 | 4.7 | 8.0 | 102.1% |
| 2 | 2 | 688.79 | 9.3 | 5.2 | 104.2% |
| 3 | 1 | 702.81 | 13.7 | 2.6 | 106.4% |
| 4 | 0 | 716.83 | 17.9 | 0.0 | 108.5% |
| 1 | 2 | 656.75 | 4.9 | 5.5 | 99.4 |
| 2 | 0 | 652.75 | 9.8 | 0.0 | 98.8 |

TABLE 2

(water/ethanol exchange)

| Ethanol equivalents [x] | Water equivalents [y] | molar mass [g/mol] | gravimetric ethanol content [%] | gravimetric water content [%] | molar mass of solvate relative to tetrahydrate [%] |
|---|---|---|---|---|---|
| 0 | 4 | 660.75 | 0.0 | 10.9 | 100.0 |
| 1 | 3 | 688.80 | 6.7 | 7.8 | 104.3 |
| 2 | 2 | 716.85 | 12.9 | 5.0 | 108.5 |
| 3 | 1 | 744.90 | 18.6 | 2.4 | 112.7 |

TABLE 2-continued (water/ethanol exchange)

| Ethanol equiva-lents [x] | Water equiva-lents [y] | molar mass [g/mol] | gravimetric ethanol content [%] | gravimetric water content [%] | molar mass of solvate relative to tetrahydrate [%] |
|---|---|---|---|---|---|
| 4 | 0 | 772.95 | 23.8 | 0.0 | 117.0 |
| 1 | 2 | 670.78 | 6.9 | 5.4 | 101.5 |
| 2 | 0 | 680.81 | 13.5 | 0.0 | 103.0 |

In the respective dynamic vapor sorption experiments discussed in more detail herein using methanol vapor at 98% relative saturation for the Dihydrate-dimethanolate/crystalline form S1 at 25° C. starting with the tetrahydrate a mass gain of 9% has been obtained. This is in good agreement with the above shown results for the tetramethanolate (calculated 108.5%, i.e. 8.5% of mass gain).

In the respective dynamic vapor sorption experiments discussed in more detail herein using ethanol vapor at 98% relative saturation for the Dihydrate-diethanolate/crystalline form S2 at 25° C. starting with the tetrahydrate a mass gain of 17% has been obtained. This is in good agreement with the above shown results for the tetraethanolate (calculated 117.0%, i.e. 17.0% of mass gain).

As is shown above and/or below, the tetrasolvates according to the invention are preferably convertible, more preferably convertible between essentially pure tetrahydrates and essentially pure tetraalcoholates, and potentially all intermediates in between, and preferably the desolvates thereof (exhibiting lower water and/or alcohol content), preferably exemplified by:

the mixed Dihydrate-dialcoholates which are discussed in detail above and/or below, and the Dihydrate-alcoholates or Dihydrate-monoalcoholates (as described by the formula [cyclo-(Arg-Gly-Asp-DPhe-NMe-Val)].[Alcohol]$_x$.[H$_2$O]$_{(y)}$ with 0≤y≤4 and x≤2−0.5·y and x≤1), and more specifically S1 and/or S2.

Since those tetrasolvates have very similar structural features, e.g. the crystallographic parameters, the analytical data and/or physical properties and additionally are convertible, it is clear that the tetrasolvates form a class or subclass of the crystalline forms according to the invention and/or of the solid materials according to the invention.

Accordingly, the tetrasolvates are a preferred subject of the instant invention are according to the invention, preferably the tetrasolvates as characterised herein.

For reasons of clarity, tetrasolvates that contain three or more equivalents of water (i.e. have a water content of >75 mole %, based on the total amount of solvent contained in the respective crystalline form) and contain less than one equivalent of one or more solvents other than water, preferably less than one equivalent of one or more alcohols, preferably selected from methanol and ethanol, are preferably referred to as hydrates, hydrates according to the invention or hydrate-tetrasolvates.

For reasons of clarity, tetrasolvates that contain close to four equivalents of water (i.e. have a water content of >90 mole % and preferably of >95 mole %, based on the total amount of solvent contained in the respective crystalline form) are preferably referred to as tetrahydrates or tetrahydrates according to the invention.

For reasons of clarity, tetrasolvates that contain one or more equivalents of alcohol (i.e. have an alcohol content of 25 mole % or higher, based on the total amount of solvent contained in the respective crystalline form) are preferably referred to as alcoholates, alcoholates according to the invention or alcoholate-tetrasolvates. Examples of such alcoholates or alcoholate-tetrasolvates are the methanolate and/or ethanolate (or methanolate-tetrasolvate and/or ethanolate-tetrasolvate) according to the invention.

For reasons of clarity, tetrasolvates that contain close to four equivalents of one or more alcohols (i.e. have an total alcohol content of >90 mole % and preferably of >95 mole %, based on the total amount of solvent contained in the respective crystalline form) are preferably referred to as tetraalcoholates or tetraalcoholates according to the invention. Examples of such tetraalcoholates are the tetramethanolate and/or tetraethanolate or the tetramethanolate and/or tetraethanolate according to the invention.

Two more tetrasolvates that can be described as alcohol solvates, alcoholate-tetrasolvates or desolvates thereof or more preferably described as Dihydrate-dialcoholates, Dihydrate-alcoholates or Dihydrate-monoalcoholates are described below:

Preferably, the tetrasolvates according to the invention, more preferably the Dihydrate-dimethanolate, the Dihydrate-methanolate, the Dihydrate-monoethanolate, the Dimethanolate and/or the desolvates thereof and especially the crystalline form S1 can be characterised, alternatively or additionally, by a melting/decomposition temperature of >205° C., more preferably 210±5° C. melting/decomposition ° C. or higher, and especially 210±5° C. melting/decomposition. Preferably, said melting/decomposition temperature obtained for the tetrasolvates according to the invention, more preferably obtained for the Dihydrate-dimethanolate, the Dihydrate-methanolate, the Dihydrate-monoethanolate, the Dimethanolate and/or the desolvates thereof and especially obtained for the crystalline form S1 is <250° C.

The melting/decomposition temperatures and/or thermal behaviors described herein are preferably determined by DSC (Differential Scanning Calorimetry) and TGA (ThermoGravimetric Analysis). DSC and/or TGA methods or generally thermoanalytic methods and suitable devices for determining them are known in the art, for examples from European Pharmacopeia 6$^{th}$ Edition chapter 2.02.34, wherein suitable standard techniques are described. More preferably, for the melting/decomposition temperatures or behaviors and/or the thermoanalysis in general, a Mettler Toledo DSC 821 and/or Mettler Toledo TGA 851 are used, preferably as described in the European Pharmacopeia 6$^{th}$ Edition chapter 2.02.34.

Figure 8:
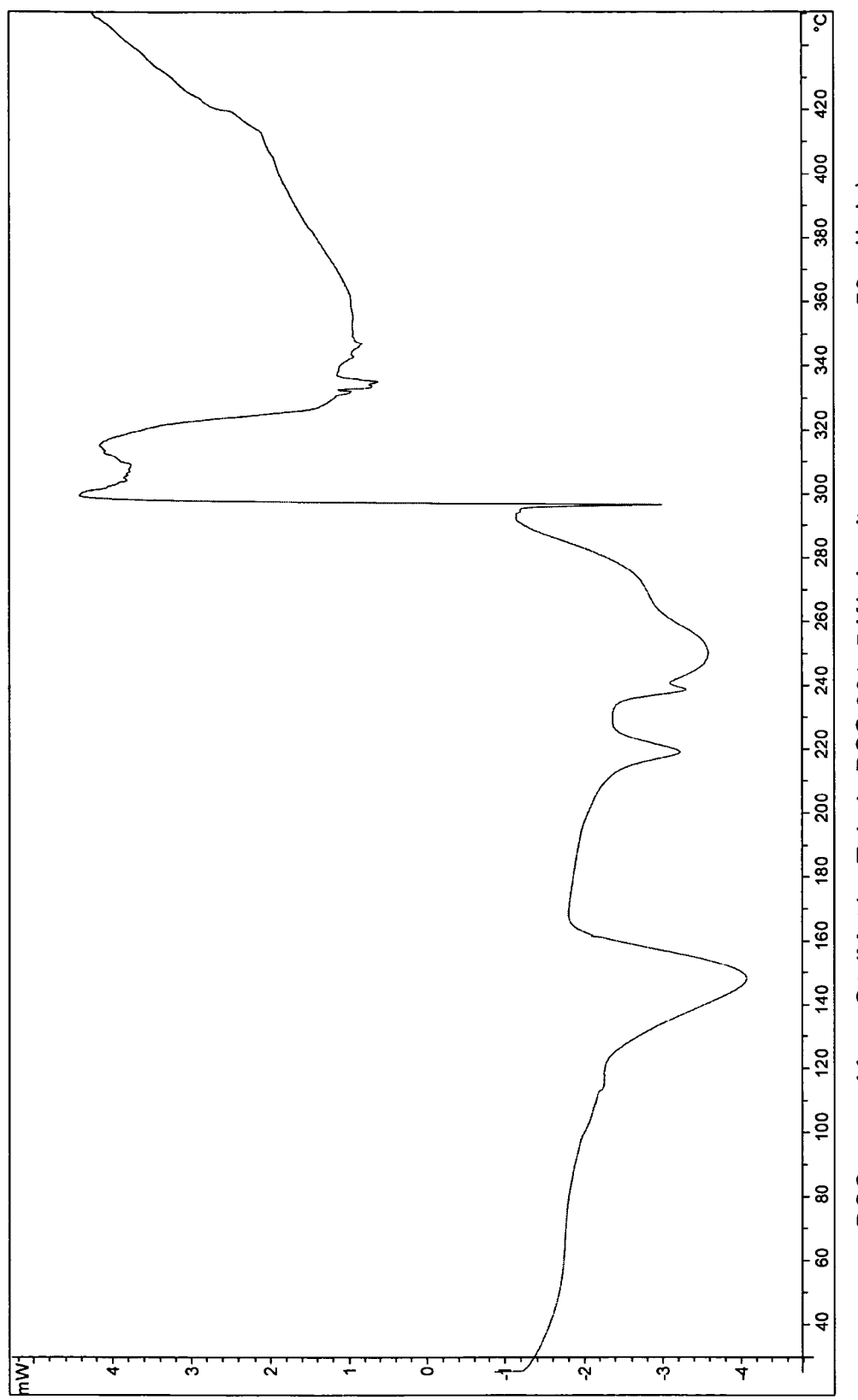
FIG. 8 depicts the DSC measurements of crystalline form S1.
Figure 9:
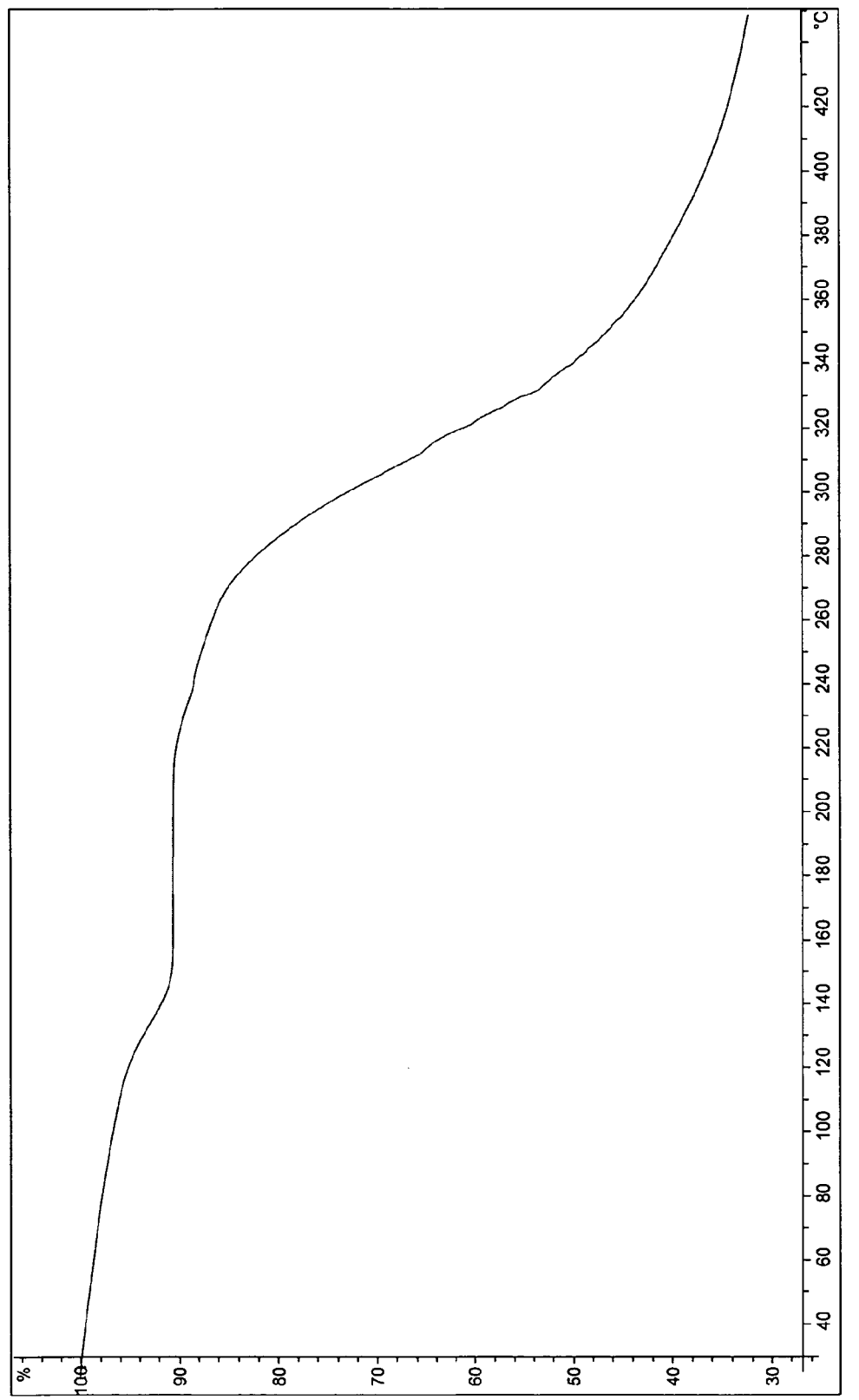
FIG. 9 depicts the TGA measurements of crystalline form S1.

The DSC and TGA measurements showing the thermal analysis (Mettler-Toledo DSC 821, 5 K/min, nitrogen purge gas 50 ml/min; Mettler-Toledo TGA 851, 5 K/min, nitrogen purge gas 50 ml/min) and the melting/decomposition temperature given above is shown in FIG. 8 and FIG. 9.

Preferably, the tetrasolvates according to the invention, more preferably the Dihydrate-dimethanolate, the Dihydrate-methanolate, the Dihydrate-monoethanolate, the Dimethanolate and/or the desolvates thereof, and especially the crystalline form S1 can be characterised, alternatively or additionally, by Powder X-Ray Diffraction and more preferably by the Powder X-Ray Diffraction pattern comprising one or more of the Powder X-ray peaks given below, more preferably comprising 6 or more of the Powder X-ray peaks given below, even more preferably 9 or more of the Powder X-ray peaks given below, and especially comprising all of the of the Powder X-ray peaks given below:

| No. | D ± 0.1 [Å] | °2θ (Co—Kα₁ radiation) ± 0.1° | Miller indices h | k | l |
|---|---|---|---|---|---|
| 1 | 13.05 | 7.9 | 0 | 2 | 0 |
| 2 | 12.47 | 8.3 | 0 | 1 | 1 |
| 5 | 7.88 | 13.1 | 1 | 0 | −1 |
| 7 | 7.60 | 13.6 | 1 | 1 | −1 |
| 8 | 7.41 | 13.9 | 0 | 3 | 1 |
| 9 | 7.09 | 14.5 | 0 | 0 | 2 |
| 10 | 6.51 | 15.8 | 0 | 4 | 0 |
| 11 | 6.23 | 16.5 | 0 | 2 | 2 |
| 12 | 5.92 | 17.4 | 0 | 4 | 1 |
| 13 | 4.89 | 21.1 | 0 | 5 | 1 |
| 14 | 4.80 | 21.5 | 0 | 4 | 2 |

Preferably, the tetrasolvates according to the invention, more preferably the Dihydrate-dimethanolate, the Dihydrate-methanolate, the Dihydrate-monoethanolate, the Dimethanolate and/or the desolvates thereof, and especially the crystalline form S1 can be characterised, alternatively or additionally, by Powder X-Ray Diffraction more preferably by the Powder X-Ray Diffraction pattern comprising one or more of the Powder X-ray peaks given below, more preferably comprising 8 or more of the Powder X-ray peaks given below, even more preferably 12 or more of the Powder X-ray peaks given below, and especially comprising all of the of the Powder X-ray peaks given below:

| No. | D [Å] | °2θ (Co—Kα₁ radiation) ± 0.1° | Miller indices h | k | l |
|---|---|---|---|---|---|
| 0 | 14.20 | 7.3 | 0 | 0 | 1 |
| 1 | 13.05 | 7.9 | 0 | 2 | 0 |
| 2 | 12.47 | 8.3 | 0 | 1 | 1 |
| 3 | 9.62 | 10.7 | 0 | 2 | 1 |
| 4 | 8.81 | 11.7 | 1 | 1 | 0 |
| 5 | 7.88 | 13.1 | 1 | 0 | −1 |
| 6 | 7.74 | 13.3 | 1 | 0 | 1 |
| 7 | 7.60 | 13.6 | 1 | 1 | −1 |
| 8 | 7.41 | 13.9 | 0 | 3 | 1 |
| 9 | 7.09 | 14.5 | 0 | 0 | 2 |
| 10 | 6.51 | 15.8 | 0 | 4 | 0 |
| 11 | 6.23 | 16.5 | 0 | 2 | 2 |
| 12 | 5.92 | 17.4 | 0 | 4 | 1 |
| 13 | 4.89 | 21.1 | 0 | 5 | 1 |
| 14 | 4.80 | 21.5 | 0 | 4 | 2 |

Preferably, the up tp tetrasolvates according to the invention, more preferably the Dihydrate-dimethanolate, the Dihydrate-methanolate, the Dihydrate-monoethanolate, the Dimethanolate and/or the desolvates thereof, and especially the crystalline form S1 can be characterised, alternatively or additionally, by Powder X-Ray Diffraction and more preferably by the Powder X-Ray Diffraction pattern comprising one or more of the Powder X-ray peaks given below, more preferably comprising 10 or more of the Powder X-ray peaks given below, even more preferably 12 or more of the Powder X-ray peaks given below, and especially comprising all of the of the Powder X-ray peaks given below:

| No. | D ± 0.1 [Å] | °2θ (Co—Kα₁ radiation) ± 0.1° | Miller indices h | k | l |
|---|---|---|---|---|---|
| 0 | 14.20 | 7.3 | 0 | 0 | 1 |
| 1 | 13.05 | 7.9 | 0 | 2 | 0 |
| 2 | 12.47 | 8.3 | 0 | 1 | 1 |
| 3 | 9.62 | 10.7 | 0 | 2 | 1 |
| 4 | 8.81 | 11.7 | 1 | 1 | 0 |
| 5 | 7.88 | 13.1 | 1 | 0 | −1 |
| 6 | 7.74 | 13.3 | 1 | 0 | 1 |
| 7 | 7.60 | 13.6 | 1 | 1 | −1 |
| 8 | 7.41 | 13.9 | 0 | 3 | 1 |
| 9 | 7.09 | 14.5 | 0 | 0 | 2 |
| 10 | 6.51 | 15.8 | 0 | 4 | 0 |
| 11 | 6.23 | 16.5 | 0 | 2 | 2 |
| 12 | 5.92 | 17.4 | 0 | 4 | 1 |
| 13 | 4.89 | 21.1 | 0 | 5 | 1 |
| 14 | 4.80 | 21.5 | 0 | 4 | 2 |

Figure 10:
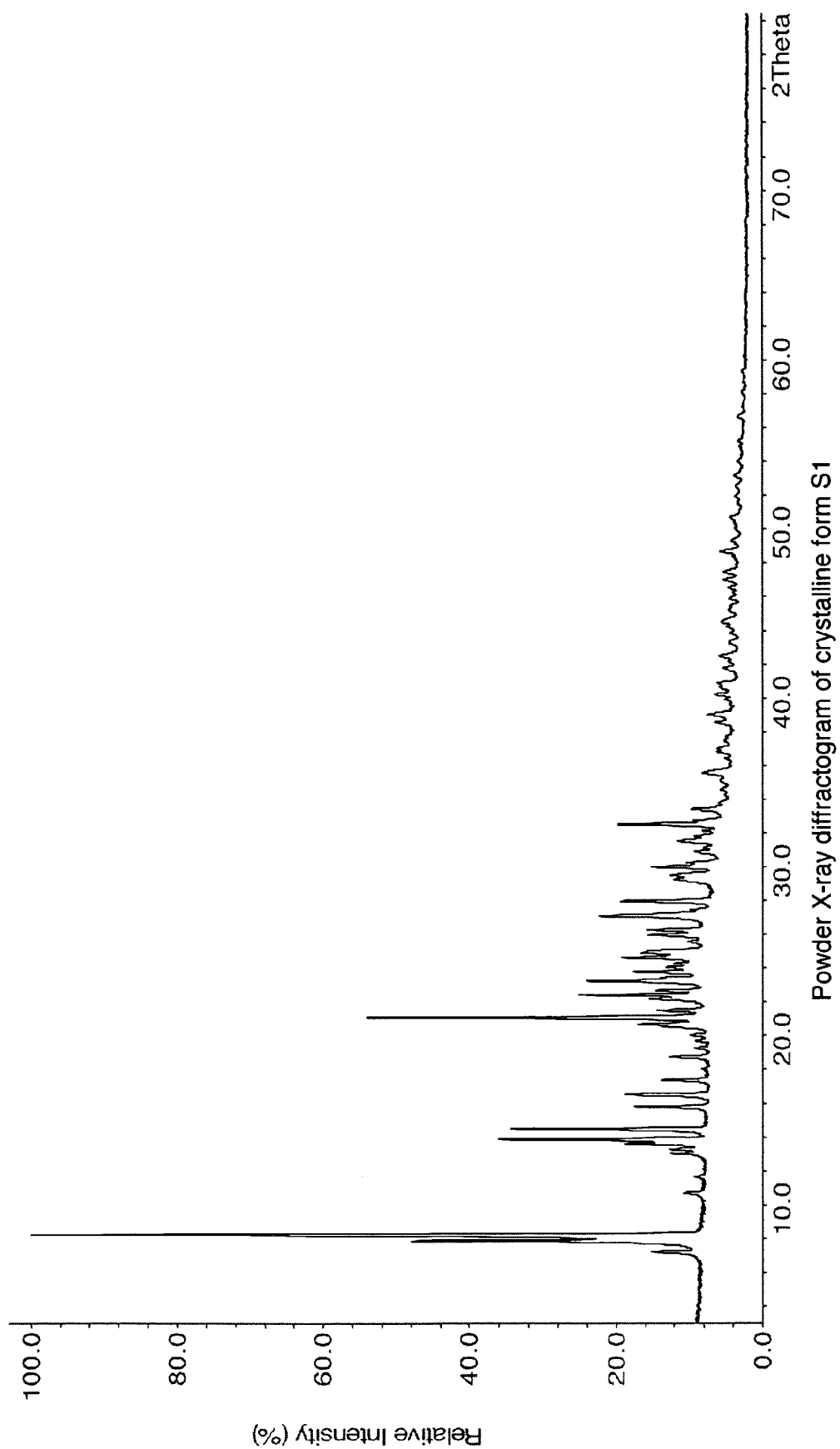
FIG. 10 depicts the powder x-ray diffractogram of crystalline form S1.

The Powder X-ray diffractogram of crystalline form S1 is shown in FIG. 10

The PXRD pattern can be successfully indexed with the following monoclinic unit cell (space group P2₁):
a=9.4 Å, b=25.9 Å, c=14.1 Å (±0.1 Å), β=91.2° (±0.1), V~3430 (±10) Å³

The Powder X-Ray Diffraction and more preferably the Powder X-Ray Diffraction pattern is preferably performed or determined as described herein and especially performed or determined by standard techniques as described in the European Pharmacopeia 6$^{th}$ Edition chapter 2.9.33, and is even more preferably obtained with the parameters Cu—Kα₁ radiation and/or λ=1.5406 Å, preferably on a Stoe StadiP 611 KL diffractometer.

Preferably, the tetrasolvates according to the invention, more preferably the Dihydrate-dimethanolate, the Dihydrate-methanolate, the Dihydrate-monoethanolate, the Dimethanolate and/or the desolvates thereof, and especially the crystalline form S1 can be characterised, alternatively or additionally, by Single Crystal X-Ray Structure Data, for example Single Crystal X-Ray Structure Data obtained on a diffractometer preferably equipped with a graphite monochromator and CCD Detector, preferably using Mo K$_α$ radiation, preferably at a temperature of 298 K±5 K, and even more preferably on a XCalibur diffractometer from Oxford Diffraction equipped with graphite monochromator and CCD Detector using Mo K$_α$ radiation at about 298 K.

Preferably, the tetrasolvates according to the invention, more preferably the Dihydrate-dimethanolate, the Dihydrate-methanolate, the Dihydrate-monoethanolate, the Dimethanolate and/or the desolvates thereof, and especially the crystalline form S1 can be characterised, alternatively or additionally, by the infrared-spectroscopy data comprising one or more of the band positions (±2 cm⁻¹) given below, more preferably comprising 3 or more of the band positions (±2 cm⁻¹) given below, even more preferably comprising 6 or more of the band positions (±2 cm⁻¹) given below, and especially comprising all the band positions (±2 cm⁻¹) given below, preferably together with the relative intensities given in brackets:

3311 cm⁻¹ (s), 2965 cm⁻¹ (m), 2875 cm⁻¹ (w), 1668 cm⁻¹ (s), 1542 cm⁻¹ (s), 1396 cm⁻¹ (m), 1028 cm⁻¹ (w), 707 cm⁻¹ (m)

More preferably, the tetrasolvates according to the invention, more preferably the Dihydrate-dimethanolate, the Dihydrate-methanolate, the Dihydrate-monoethanolate, the Dimethanolate and/or the desolvates thereof, and especially the crystalline form S1 can be characterised, alternatively or additionally, by the infrared-spectroscopy data comprising one or more of the band positions (±2 cm$^{-1}$) given below, more preferably comprising 6 or more of the band positions (±2 cm$^{-1}$) given below, even more preferably comprising 9 or more of the band positions (±2 cm$^{-1}$) given below, and especially comprising all the band positions (±2 cm$^{-1}$) given below, preferably together with the relative intensities given in brackets:

3311 cm$^{-1}$ (s), 3067 cm$^{-1}$ (m), 2965 cm$^{-1}$ (m), 2937 cm$^{-1}$ (m), 2875 cm$^{-1}$ (w), 1668 cm$^{-1}$ (s), 1542 cm$^{-1}$ (s), 1456 cm$^{-1}$ (m), 1396 cm$^{-1}$ (m), 1028 cm$^{-1}$ (w), 707 cm$^{-1}$ (m)

The relative intensities given in brackets are preferably defined as follows: *"s"=strong (transmittance preferably ≤50%), "m"=medium (preferably 50%<transmittance≤70%), "w"=weak (transmittance preferably >70%)

The IR or FT-IR spectrum is preferably obtained using a KBr pellet as sample preparation technique.

The IR-spectroscopy data is preferably obtained by FT-IR-spectroscopy, The IR-spectroscopy data or FT-IR-spectroscopy data is preferably obtained by standard techniques as described in the European Pharmacopeia 6$^{th}$ Edition chapter 2.02.24. For the measurement of the FT-IR-spectra, preferably a Bruker Vector 22 spectrometer is used. FT-IR spectra are preferably base-line corrected, preferably using Bruker OPUS software.

Figure 11:
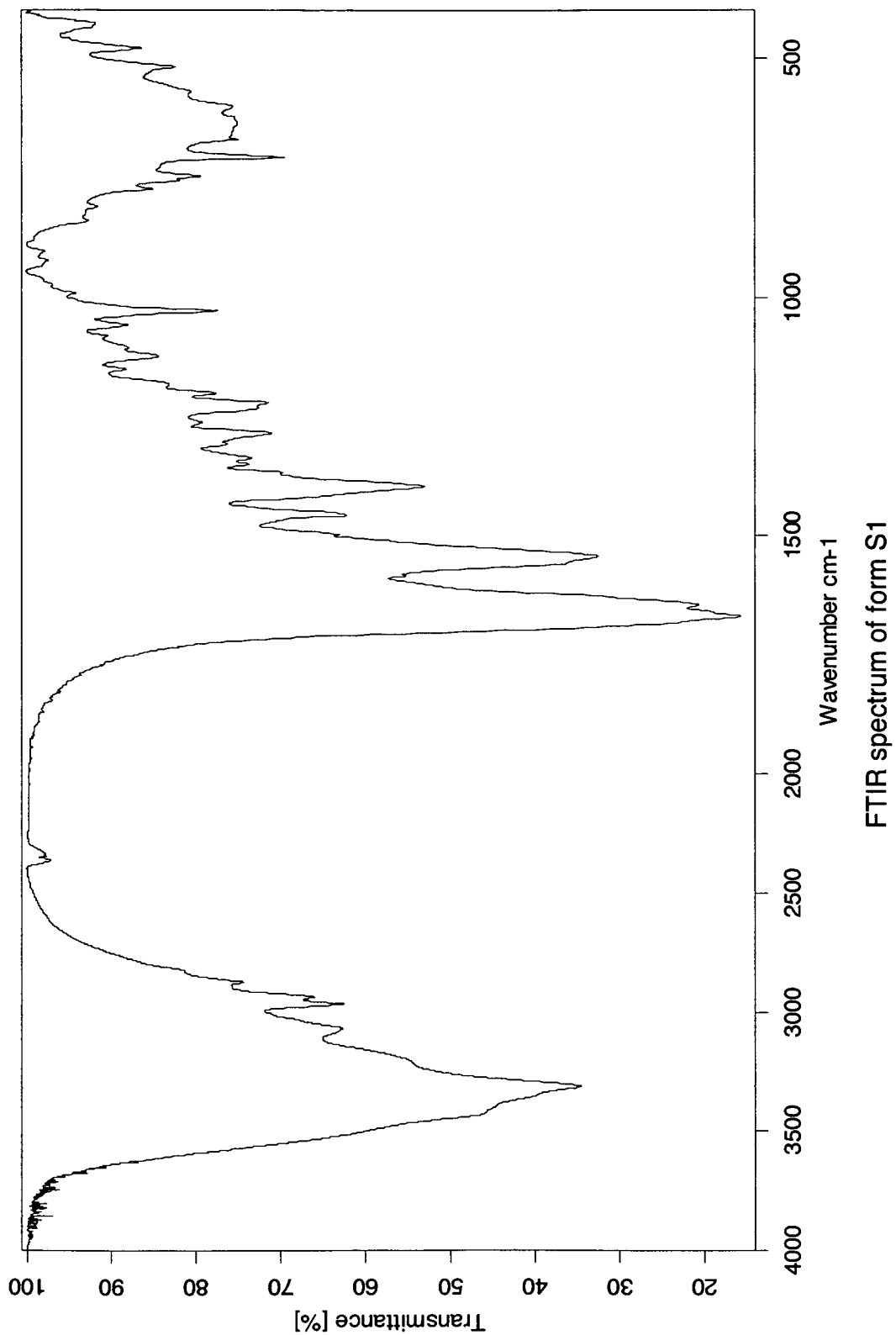
FIG. 11 depicts the FT-IR spectrum of crystalline form S1.

The FT-IR spectra of the tetrasolvates according to the invention, more preferably the Dihydrate-dimethanolate, the Dihydrate-methanolate, the Dihydrate-monoethanolate, the Dimethanolate and/or the desolvates thereof, and especially the crystalline form S1 is given in FIG. 11.

Preferably, the tetrasolvates according to the invention, more preferably the Dihydrate-dimethanolate, the Dihydrate-methanolate, the Dihydrate-monoethanolate, the Dimethanolate and/or the desolvates thereof, and especially the crystalline form S1 can be characterised, alternatively or additionally, by the Raman-spectroscopy data comprising one or more of the band positions (±2 cm$^{-1}$) given below, more preferably comprising 5 or more of the band positions (±2 cm$^{-1}$) given below, even more preferably comprising 8 or more of the band positions (±2 cm$^{-1}$) given below, and especially comprising all the band positions (±2 cm$^{-1}$) given below, preferably together with the relative intensities given in brackets:

3067 cm$^{-1}$ (w), 2936 cm$^{-1}$ (s), 1668 cm$^{-1}$ (m), 1606 cm$^{-1}$ (w), 1446 cm$^{-1}$ (w), 1338 cm$^{-1}$ (w), 1203 cm$^{-1}$ (w), 1033 cm$^{-1}$ (w), 1004 cm$^{-1}$ (s), 904 cm$^{-1}$ (m), 624 cm$^{-1}$ (w).

More preferably, the tetrasolvates according to the invention, more preferably the Dihydrate-dimethanolate, the Dihydrate-methanolate, the Dihydrate-monoethanolate, the Dimethanolate and/or the desolvates thereof, and especially the crystalline form S1 can be characterised, alternatively or additionally, by the Raman-spectroscopy data comprising one or more of the and positions (±2 cm$^{-1}$) given below, more preferably comprising 9 or more of the band positions (±2 cm$^{-1}$) given below, even more preferably comprising 12 or more of the band positions (±2 cm$^{-1}$) given below, and especially comprising all the band positions (±2 cm$^{-1}$) given below, preferably together with the relative intensities given in brackets:

3067 cm$^{-1}$ (w), 2936 cm$^{-1}$ (s), 1668 cm$^{-1}$ (m), 1606 cm$^{-1}$ (w), 1585 cm$^{-1}$ (w), 1446 cm$^{-1}$ (w), 1338 cm$^{-1}$ (w), 1203 cm$^{-1}$ (w), 1123 cm$^{-1}$ (w), 1033 cm$^{-1}$ (w), 1004 cm$^{-1}$ (s), 904 cm$^{-1}$ (m), 824 cm$^{-1}$ (w), 624 cm$^{-1}$ (w), 523 cm$^{-1}$ (w).

The relative intensities given in brackets are preferably defined as follows: "s"=strong (relative Raman intensity preferably ≥0.04), "m"=medium (preferably 0.04>relative Raman intensity≥0.02), "w"=weak (relative Raman intensity preferably <0.02)

The Raman or FT-Raman spectrum is preferably obtained using Aluminium-cups as sample holders for the respective solid material.

The Raman-spectroscopy data is preferably obtained by FT-Raman-spectroscopy, The Raman-spectroscopy data or FT-Raman-spectroscopy data is preferably obtained by standard techniques as described in the European Pharmacopeia 6$^{th}$ Edition chapter 2.02.48. For the measurement of the FT-Raman-spectra, preferably a Bruker RFS 100 spectrometer is used. FT-Raman spectra are preferably base-line corrected, preferably using Bruker OPUS software.

Figure 12:
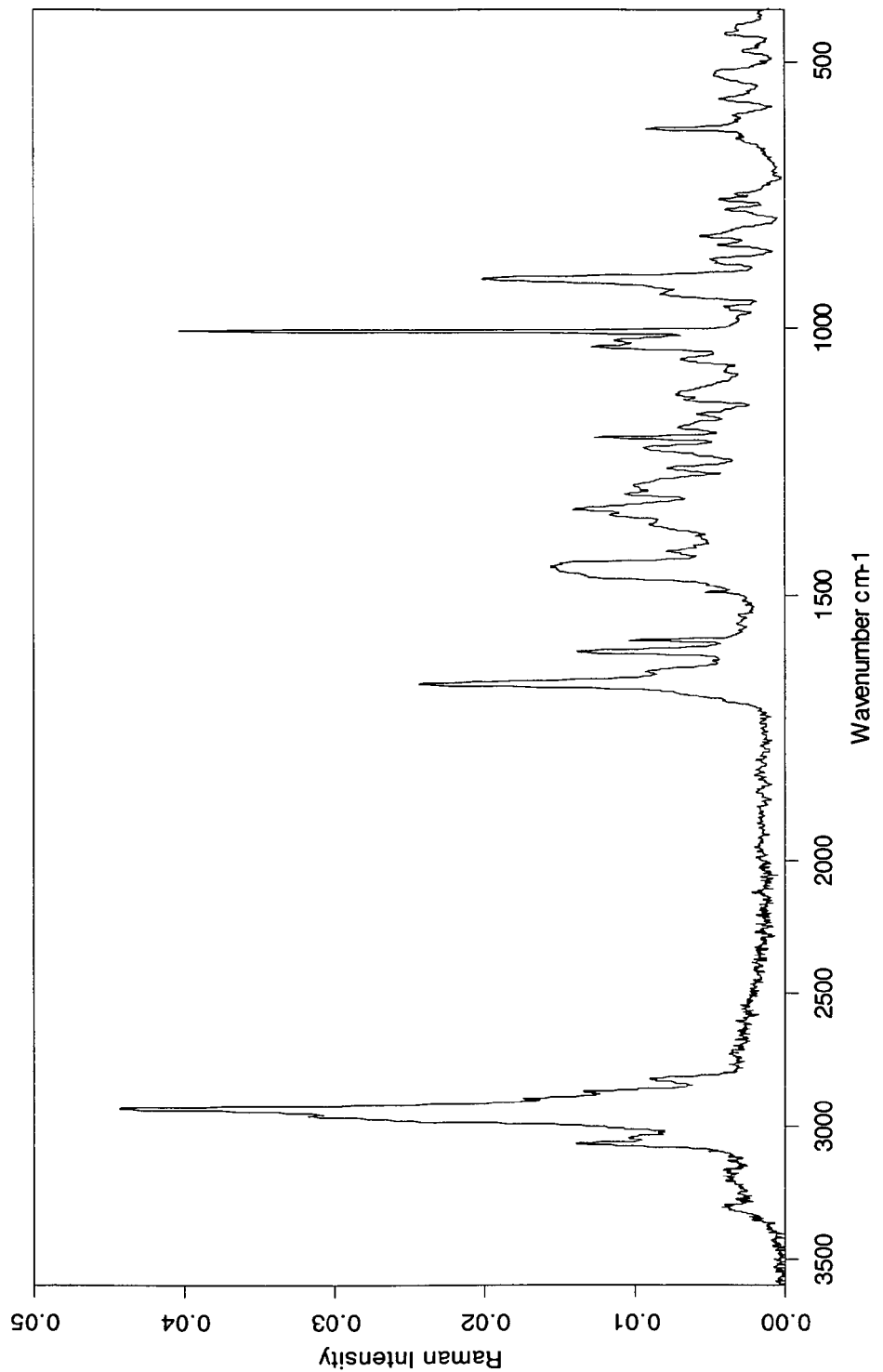
FIG. 12 depicts the FT-Raman spectrum of crystalline form S1.

The FT-Raman spectra of the tetrasolvates according to the invention and especially the crystalline form S1 is given in FIG. 12.

Preferably, the tetrasolvates according to the invention, more preferably the Dihydrate-dimethanolate, the Dihydrate-methanolate, the Dihydrate-monoethanolate, the Dimethanolate and/or the desolvates thereof, and especially the crystalline form S1 can be characterised, alternatively or additionally, by dynamic vapour experiments using water vapour and/or methanol vapour. The results can be obtained by standard techniques as described in Rolf Hilfiker, 'Polymorphism in the Pharmaceutical Industry', Wiley-VCH. Weinheim 2006 (Chapter 9: Water Vapour Sorption, and references therein).

The Water Vapour Sorption behaviour of the tetrasolvates according to the invention, more preferably the Dihydrate-dimethanolate, the Dihydrate-methanolate, the Dihydrate-monoethanolate, the Dimethanolate and/or the desolvates thereof, and especially the crystalline form S1 shows a mass loss of approx. 8 wt % in the first desorption cycle (which is slightly lower than the observed Methanol mass gain in the Methanol Vapour Sorption experiment). Upon water vapour adsorption, an assembly of water molecules in the lattice is observed, with a maximum weight gain of approx. 8 wt % at elevated rh. In the second desorption cycle a total mass loss of approx. 9.9 wt % is observed. For a Dihydrate Di-Methanolate of the compound of formula I, the calculated Methanol content equals 9.3 wt %. Form S1 can be shown to be the thermodynamically stable form in an atmosphere of 100% Methanol vapour. Water Vapor Sorption isotherm (25° C.) of crystalline form S1 (SMS DVS Intrinsic) is given in FIG. 13. Methanol Vapour Sorption Isotherm (25° C.) of a hydrate form to form S1 (SMS DVS Advantage) FIG. 14.

Figure 13:
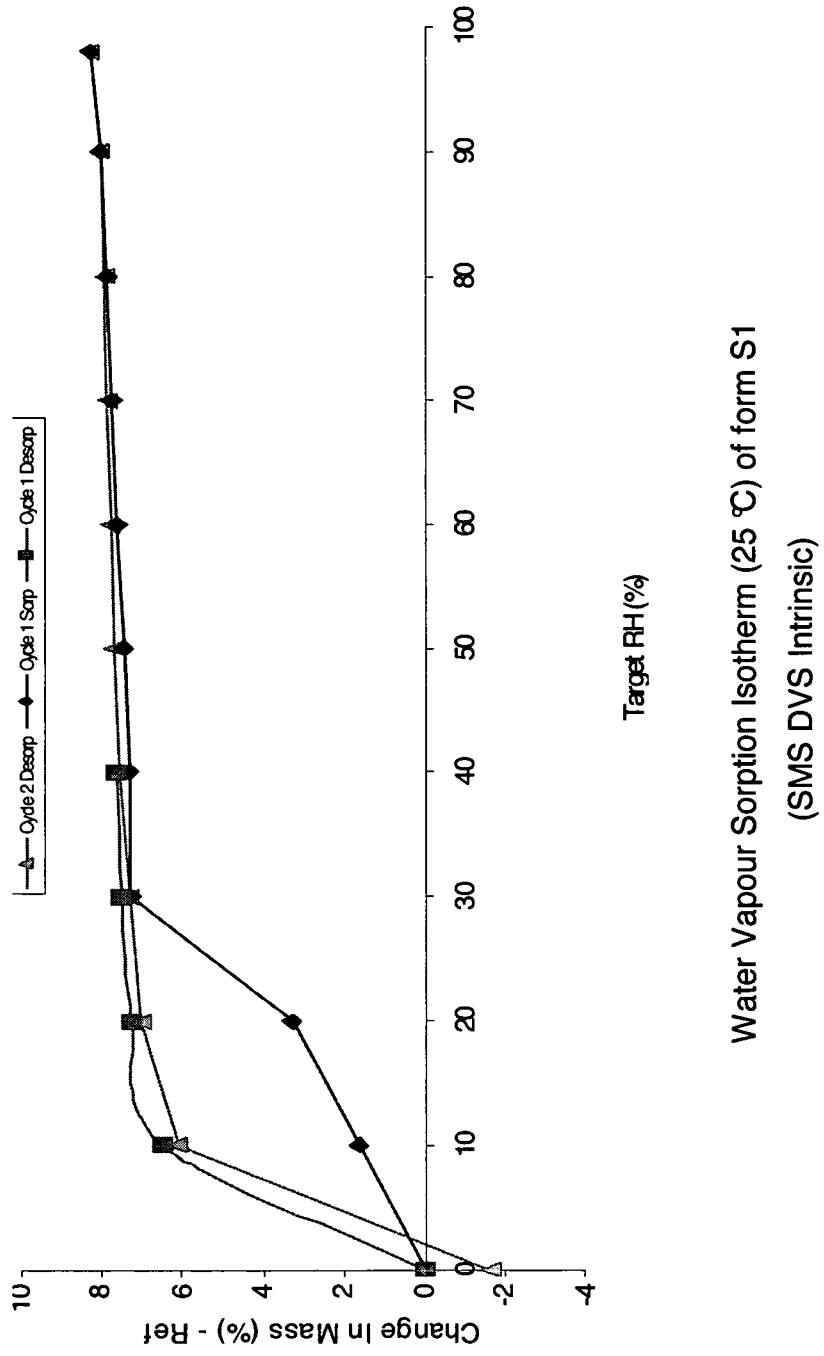
FIG. 13 depicts the water vapour sorption isotherm of crystalline form S1.
Figure 14:
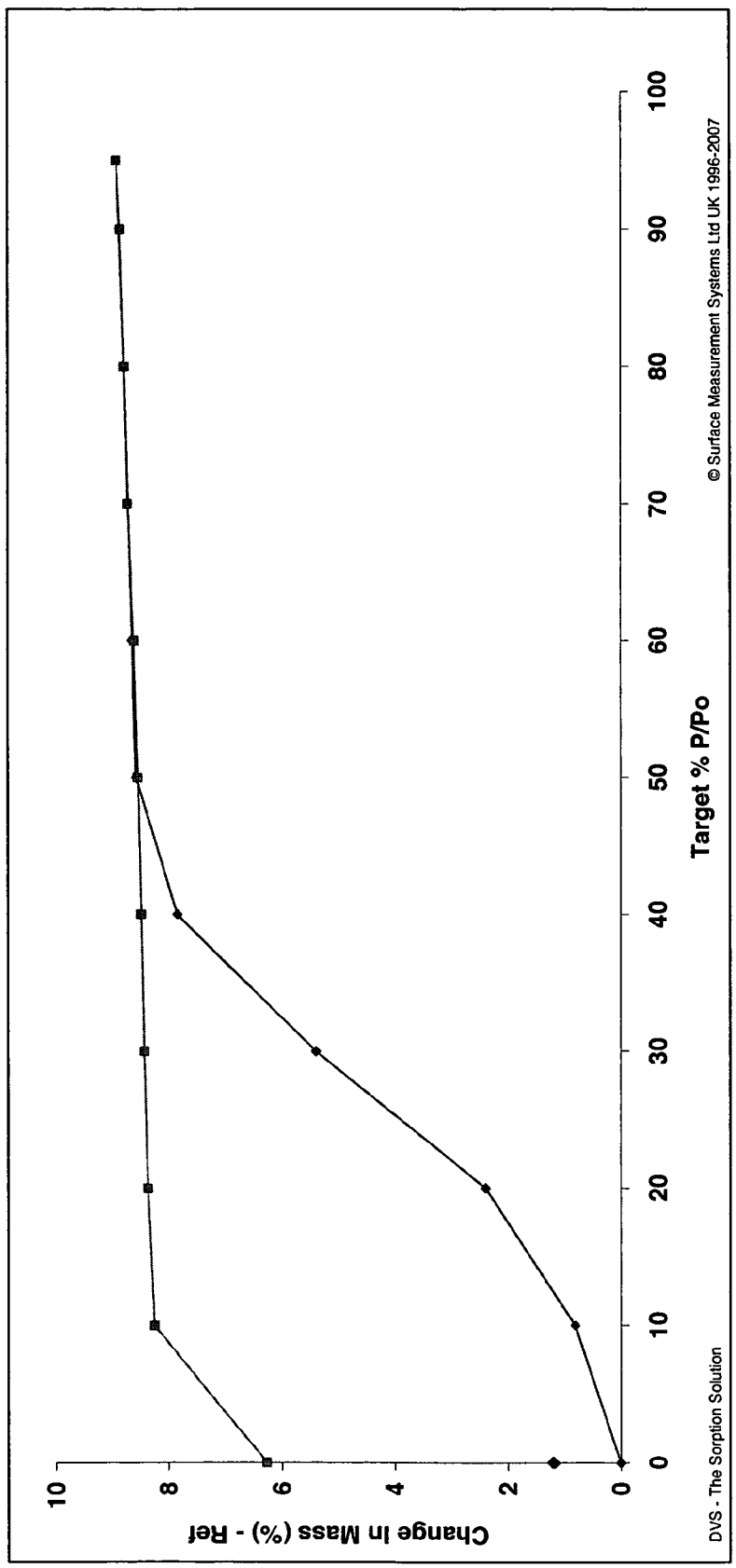
FIG. 14 depicts the methanol vapour sorption isotherm of a hydrate form to form S1.

Thus, crystalline form S1 is a crystalline Methanol solvate form or a mixed water/methanol solvate form, preferably selected from the Dihydrate-methanolate, the Dihydrate-monoethanolate, the Dimethanolate and/or the desolvates thereof, which can be obtained e.g. via Methanol Vapour Sorption, preferably via Methanol Vapour Sorption starting with a hydrate structure, such as the hydrates according to the invention and especially the tetrahydrate according to the invention, i.e crystalline form S3. From the Methanol Vapour Sorption curve as shown in FIG. 13 and as discussed above, it can be seen that at elevated Methanol partial pressure, approx. 9 wt % Methanol are taken up by the sample.

Preferably, the tetrasolvates according to the invention, more preferably the Dihydrate-diethanolate, the Dihydrate-ethanolate, the Dihydrate-monoethanolate, the Diethanolate and/or the desolvates thereof, and especially the crystalline form S2 can be characterised, alternatively or additionally, by a melting/decomposition temperature of >205° C., more preferably 210±5° C. melting/decomposition ° C. or higher, and especially 210±5° C. melting/decomposition. Preferably, said melting/decomposition temperature obtained for the tetrasolvates according to the invention, more preferably the Dihydrate-diethanolate, the Dihydrate-ethanolate, the Dihydrate-monoethanolate, the Diethanolate and/or the desolvates thereof, and especially obtained for the crystalline form S2 is <250° C.

The melting/decomposition temperatures and/or thermal behaviors described herein are preferably determined by DSC (Differential Scanning Calorimetry) and TGA (ThermoGravimetric Analysis). DSC and/or TGA methods or generally thermoanalysis methods and suitable devices for determining them are known in the art, for examples from European Pharmacopeia 6$^{th}$ Edition chapter 2.02.34, wherein suitable standard techniques are described. More preferably, for the melting/decomposition temperatures or behaviors and/or the thermoanalysis in general, a Mettler Toledo DSC 821 and/or Mettler Toledo TGA 851 are used, preferably as described in the European Pharmacopeia 6$^{th}$ Edition chapter 2.02.34.

Figure 15:
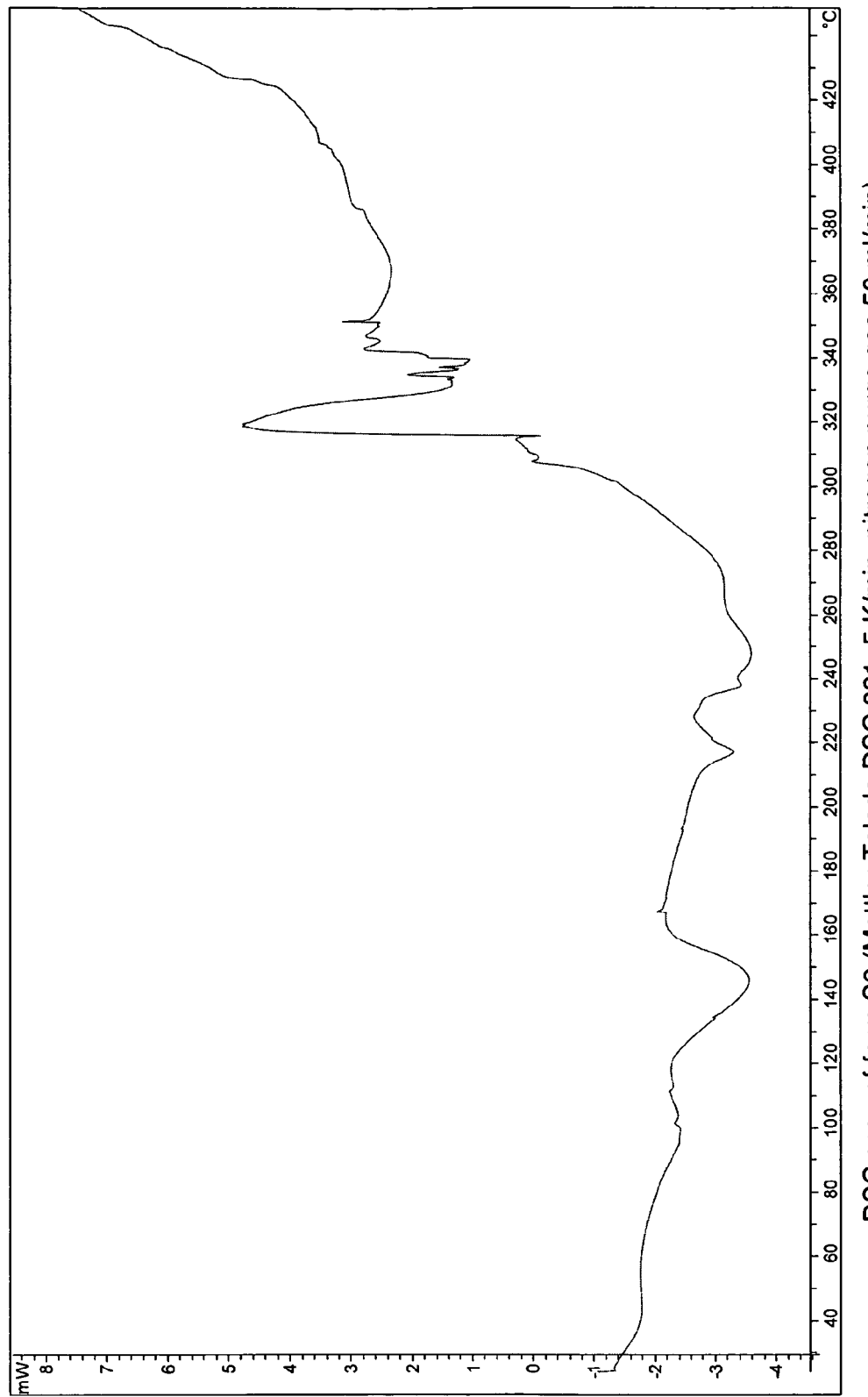
FIG. 15 depicts the DSC measurements of crystalline form S2.
Figure 16:
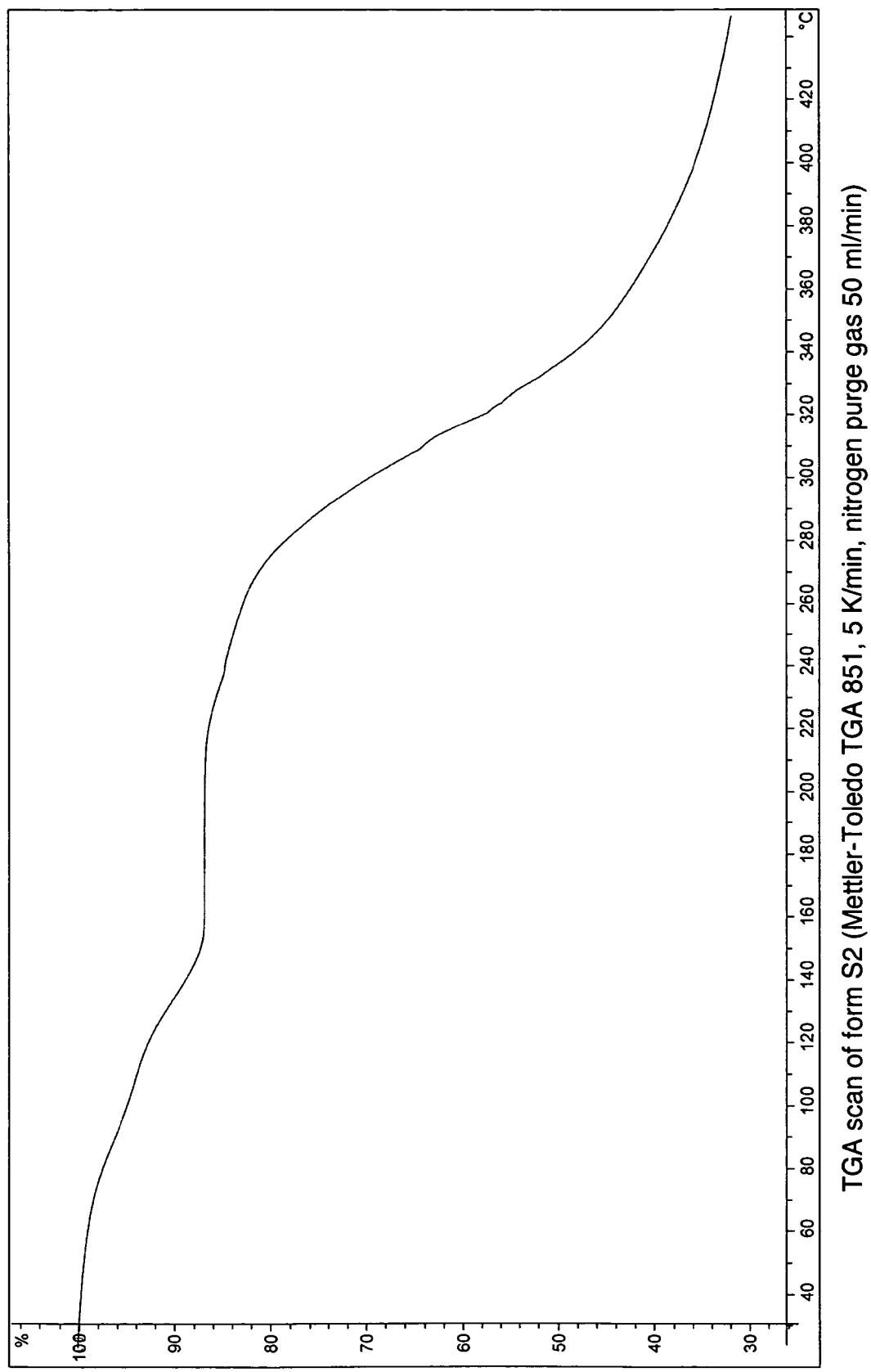
FIG. 16 depicts the TGA measurements of crystalline form S2.

The DSC and TGA measurements showing the thermal analysis (Mettler-Toledo DSC 821, 5 K/min, nitrogen purge gas 50 ml/min; Mettler-Toledo TGA 851, 5 K/min, nitrogen purge gas 50 ml/min) and the melting/decomposition temperature given above is shown in FIG. 15 and FIG. 16.

Preferably, the tetrasolvates according to the invention, more preferably the Dihydrate-diethanolate, the Dihydrate-ethanolate, the Dihydrate-monoethanolate, the Diethanolate and/or the desolvates thereof, and especially the crystalline form S2 can be characterised, alternatively or additionally, by Powder X-Ray Diffraction and more preferably by the Powder X-Ray Diffraction pattern comprising one or more of the Powder X-ray peaks given below, more preferably comprising 3 or more of the Powder X-ray peaks given below, even more preferably 5 or more of the Powder X-ray peaks given below, and especially comprising all of the of the Powder X-ray peaks given below:

a)

| No. | D ± 0.1 [Å] | °2θ (Co—Kα$_1$ radiation) ± 0.1° | Miller indices h | k | l |
|---|---|---|---|---|---|
| 1 | 13.32 | 7.7 | 2 | 0 | 0 |
| 2 | 12.89 | 8.0 | 1 | 1 | 0 |
| 4 | 7.87 | 13.1 | 0 | 1 | 1 |
| 5 | 7.54 | 13.6 | 1 | 1 | 1 |
| 6 | 7.36 | 14.0 | 0 | 2 | 0 |
| 9 | 4.82 | 21.3 | 1 | 3 | 0 |
| 10 | 4.58 | 22.5 | 1 | 0 | 2 | or more preferably b)

| No. | D ± 0.1 [Å] | °2θ (Cu—Kα$_1$ radiation) ± 0.1° | Miller indices k | l | hl |
|---|---|---|---|---|---|
| 1 | 13.32 | 7.7 | 2 | 0 | 0 |
| 2 | 12.89 | 8.0 | 1 | 1 | 0 |
| 4 | 7.87 | 13.1 | 0 | 1 | 1 |
| 5 | 7.54 | 13.6 | 1 | 1 | 1 |
| 6 | 7.36 | 14.0 | 0 | 2 | 0 |
| 9 | 4.82 | 21.3 | 3 | 2 | 1 |
| 10 | 4.58 | 22.5 | 1 | 0 | 2 |

Preferably, the tetrasolvates according to the invention, more preferably the Dihydrate-diethanolate, the Dihydrate-ethanolate, the Dihydrate-monoethanolate, the Diethanolate and/or the desolvates thereof, and especially the crystalline form S2 can be characterised, alternatively or additionally, by Powder X-Ray Diffraction, more preferably by the Powder X-Ray Diffraction pattern comprising one or more of the Powder X-ray peaks given below, more preferably comprising 4 or more of the Powder X-ray peaks given below, even more preferably 6 or more of the Powder X-ray peaks given below, and especially comprising all of the of the Powder X-ray peaks given below:

a)

| No. | D [Å] | °2θ (Co—Kα$_1$ radiation) ± 0.1° | Miller indices h | k | l |
|---|---|---|---|---|---|
| 1 | 13.32 | 7.7 | 2 | 0 | 0 |
| 2 | 12.89 | 8.0 | 1 | 1 | 0 |
| 4 | 7.87 | 13.1 | 0 | 1 | 1 |
| 5 | 7.54 | 13.6 | 1 | 1 | 1 |
| 6 | 7.36 | 14.0 | 0 | 2 | 0 |
| 7 | 5.01 | 20.6 | 5 | 1 | 0 |
| 9 | 4.82 | 21.3 | 1 | 3 | 0 |
| 10 | 4.58 | 22.5 | 1 | 0 | 2 | or more preferably b)

| No. | D [Å] | °2θ (Cu—Kα$_1$ radiation) ± 0.1° | Miller indices k | l | hl |
|---|---|---|---|---|---|
| 1 | 13.32 | 7.7 | 2 | 0 | 0 |
| 2 | 12.89 | 8.0 | 1 | 1 | 0 |
| 4 | 7.87 | 13.1 | 0 | 1 | 1 |
| 5 | 7.54 | 13.6 | 1 | 1 | 1 |
| 6 | 7.36 | 14.0 | 0 | 2 | 0 |
| 7 | 5.01 | 20.6 | 5 | 1 | 0 |
| 9 | 4.82 | 21.3 | 3 | 2 | 1 |
| 10 | 4.58 | 22.5 | 1 | 0 | 2 |

Preferably, the tetrasolvates according to the invention, more preferably the Dihydrate-diethanolate, the Dihydrate-ethanolate, the Dihydrate-monoethanolate, the Diethanolate and/or the desolvates thereof, and especially the crystalline form S2 can be characterised, alternatively or additionally, by Powder X-Ray Diffraction and more preferably by the Powder X-Ray Diffraction pattern comprising one or more of the Powder X-ray peaks given below, more preferably comprising 10 or more of the Powder X-ray peaks given below, even more preferably 12 or more of the Powder X-ray peaks given below, and especially comprising all of the of the Powder X-ray peaks given below:

a)

| No. | D ± 0.1 [Å] | °2θ (Co—Kα₁ radiation) ± 0.1° | Miller indices h | k | l |
|---|---|---|---|---|---|
| 0 | 14.73 | 6.9 | 0 | 1 | 0 |
| 1 | 13.32 | 7.7 | 2 | 0 | 0 |
| 2 | 12.89 | 8.0 | 1 | 1 | 0 |
| 3 | 8.78 | 11.7 | 1 | 0 | 1 |
| 4 | 7.87 | 13.1 | 0 | 1 | 1 |
| 5 | 7.54 | 13.6 | 1 | 1 | 1 |
| 6 | 7.36 | 14.0 | 0 | 2 | 0 |
| 7 | 7.10 | 14.5 | 1 | 2 | 0 |
| 8 | 5.01 | 20.6 | 5 | 1 | 0 |
| 9 | 4.82 | 21.3 | 1 | 3 | 0 |
| 10 | 4.58 | 22.5 | 1 | 0 | 2 |
| 11 | 4.38 | 23.6 | 1 | 1 | 2 |
| 12 | 4.28 | 24.1 | 1 | 3 | 1 |
| 13 | 3.81 | 27.1 | 4 | 0 | 2 |
| 14 | 3.69 | 28.0 | 4 | 1 | 2 | or more preferably b)

| No. | D ± 0.1 [Å] | °2θ (Co—Kα₁ radiation) ± 0.1° | Miller indices k | l | h |
|---|---|---|---|---|---|
| 0 | 14.73 | 6.9 | 0 | 1 | 0 |
| 1 | 13.32 | 7.7 | 2 | 0 | 0 |
| 2 | 12.89 | 8.0 | 1 | 1 | 0 |
| 3 | 8.78 | 11.7 | 1 | 0 | 1 |
| 4 | 7.87 | 13.1 | 0 | 1 | 1 |
| 5 | 7.54 | 13.6 | 1 | 1 | 1 |
| 6 | 7.36 | 14.0 | 0 | 2 | 0 |
| 7 | 7.10 | 14.5 | 1 | 2 | 0 |
| 8 | 5.01 | 20.6 | 5 | 1 | 0 |
| 9 | 4.82 | 21.3 | 3 | 2 | 1 |
| 10 | 4.58 | 22.5 | 1 | 0 | 2 |
| 11 | 4.38 | 23.6 | 1 | 1 | 2 |
| 12 | 4.28 | 24.1 | 1 | 3 | 1 |
| 13 | 3.81 | 27.1 | 6 | 2 | 0 |
| 14 | 3.69 | 28.0 | 0 | 4 | 0 |

Figure 17:
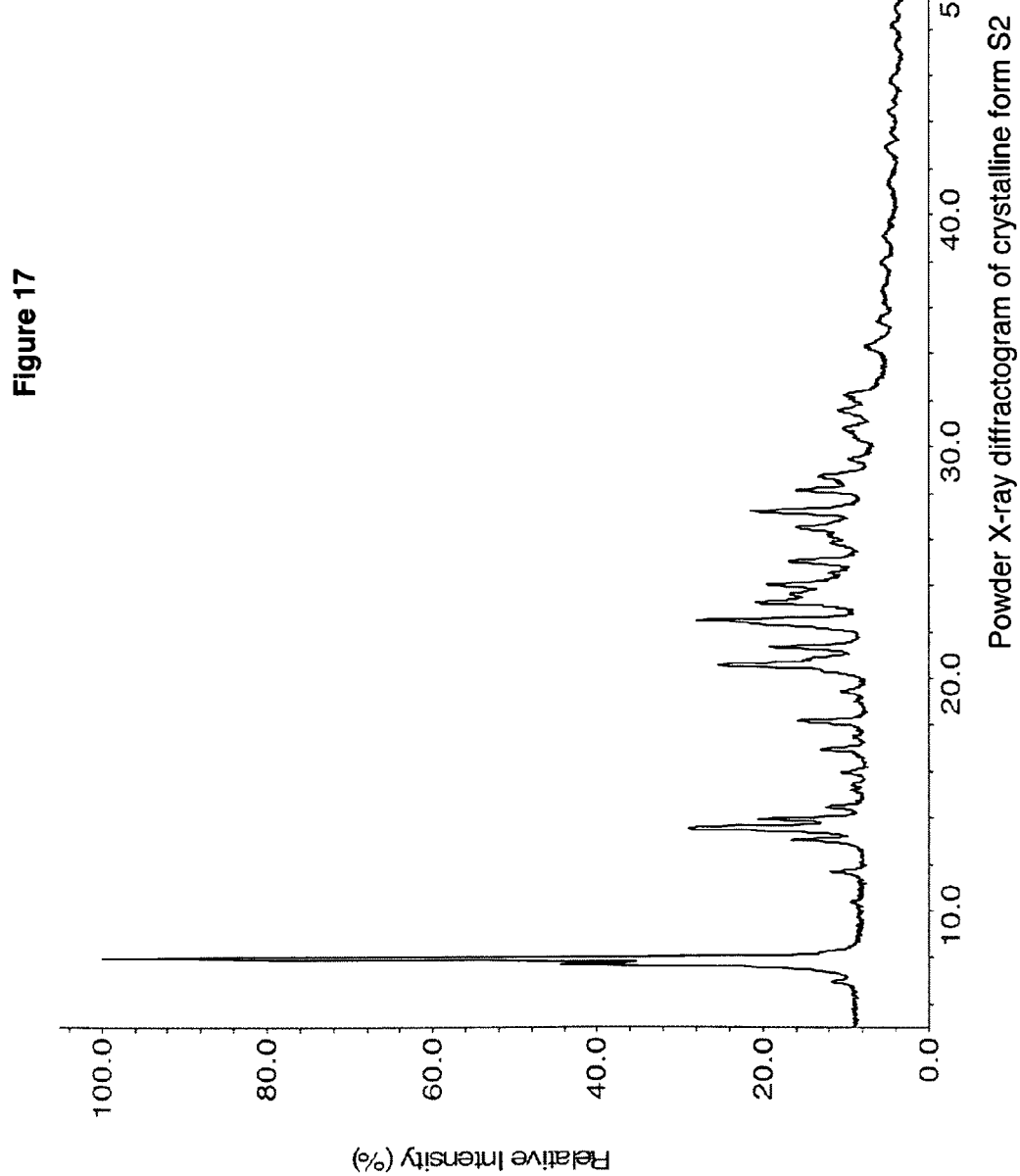
FIG. 17 depicts the powder x-ray diffractogram of crystalline form S2.

The Powder X-ray diffractogram of crystalline form S2 is shown in FIG. 17

The PXRD pattern can be successfully indexed with the following orthorhombic unit cell (space group P2₁2₁2₁):
a=9.3 Å, b=26.6 Å, c=14.7 Å (±0.1 Å), V~3600 (±10) Å³

The Powder X-Ray Diffraction and more preferably the Powder X-Ray Diffraction pattern is preferably performed or determined as described herein and especially performed or determined by standard techniques as described in the European Pharmacopeia 6$^{th}$ Edition chapter 2.9.33, and is even more preferably obtained with the parameters Cu—Kα₁ radiation and/or λ=1.5406 Å, preferably on a Stoe StadiP 611 KL diffractometer.

Preferably, the tetrasolvates according to the invention, more preferably the Dihydrate-diethanolate, the Dihydrate-ethanolate, the Dihydrate-monoethanolate, the Diethanolate and/or the desolvates thereof, and especially the crystalline form S2 can be characterised, alternatively or additionally, by Single Crystal X-Ray Structure Data, for example Single Crystal X-Ray Structure Data obtained on a diffractometer preferably equipped with a graphite monochromator and CCD Detector, preferably using Mo Kα radiation, preferably at a temperature of 298 K±5 K, and even more preferably on a XCalibur diffractometer from Oxford Diffraction equipped with graphite monochromator and CCD Detector using Mo Kα radiation at about 298 K.

According to the Single Crystal X-Ray Structure Data obtained, the tetrasolvates according to the invention, more preferably the Dihydrate-diethanolate, the Dihydrate-ethanolate, the Diethanolate and/or the desolvates thereof, and especially the crystalline form S2, crystallise in the orthorhombic space group P 2₁2₁ 2₁ with the lattice parameters a=9.3 Å, b=26.3 Å, c=13.7 Å (±0.1 Å) and the unit cell volume is preferably is 3351 (±10) Å³

From the single crystal structure it is obvious that form S2 represents a tetrasolvate according to the invention and more specifically a mixed ethanol-water solvate and even more specifically a Dihydrate-monoethanolate.

Figure 32:
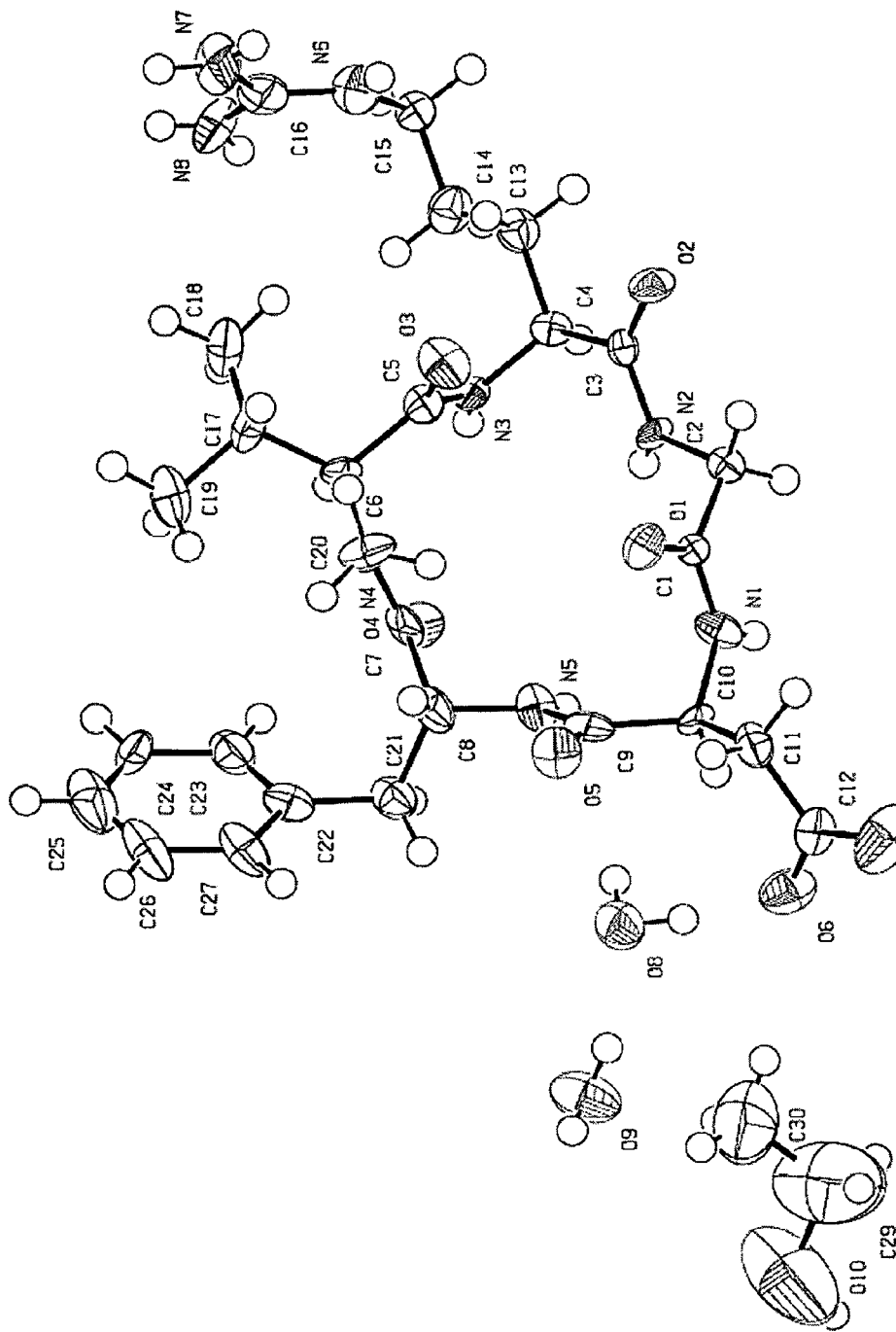
FIG. 32 depicts the single crystal structure solution of crystalline form S2.

The Single Crystal X-Ray Structure is depicted in FIG. 32.

Preferably, the tetrasolvates according to the invention, more preferably the Dihydrate-diethanolate, the Dihydrate-ethanolate, the Dihydrate-monoethanolate, the Diethanolate and/or the desolvates thereof, and especially the crystalline form S2 can be characterised, alternatively or additionally, by the infrared-spectroscopy data comprising one or more of the band positions (±2 cm⁻¹) given below, more preferably comprising 3 or more of the band positions (±2 cm⁻¹) given below, even more preferably comprising 6 or more of the band positions (±2 cm⁻¹) given below, and especially comprising all the band positions (±2 cm⁻¹) given below, preferably together with the relative intensities given in brackets:
3306 cm⁻¹ (s), 2968 cm⁻¹ (m), 1668 cm⁻¹ (s), 1546 cm⁻¹ (s), 1395 cm⁻¹ (m), 1223 cm⁻¹ (w), 1049 cm⁻¹ (w), 705 cm⁻¹ (w).

More preferably, the tetrasolvates according to the invention, more preferably the Dihydrate-diethanolate, the Dihydrate-ethanolate, the Dihydrate-monoethanolate, the Diethanolate and/or the desolvates thereof, and especially the crystalline form S2 can be characterised, alternatively or additionally, by the infrared-spectroscopy data comprising one or more of the band positions (±2 cm⁻¹) given below, more preferably comprising 6 or more of the band positions (±2 cm⁻¹) given below, even more preferably comprising 9 or more of the band positions (±2 cm⁻¹) given below, and especially comprising all the band positions (±2 cm⁻¹) given below, preferably together with the relative intensities given in brackets:
3306 cm⁻¹ (s), 2968 cm⁻¹ (m), 2872 cm⁻¹ (m), 1668 cm⁻¹ (s), 1546 cm⁻¹ (s), 1452 cm⁻¹ (w), 1395 cm⁻¹ (m), 1223 cm⁻¹ (w), 1086 cm⁻¹ (w), 1049 cm⁻¹ (w), 746 cm⁻¹ (w), 705 cm⁻¹ (w).

The relative intensities given in brackets are preferably defined as follows: *"s"=strong (transmittance preferably ≤50%), "m"=medium (preferably 50%<transmittance≤70%), "w"=weak (transmittance preferably >70%)

The IR or FT-IR spectrum is preferably obtained using a KBr pellet as sample preparation technique.

The IR-spectroscopy data is preferably obtained by FT-IR-spectroscopy, The IR-spectroscopy data or FT-IR-spectroscopy data is preferably obtained by standard techniques as described in the European Pharmacopeia 6$^{th}$ Edition chapter 2.02.24. For the measurement of the FT-IR-spectra, preferably a Bruker Vector 22 spectrometer is used. FT-IR spectra are preferably base-line corrected, preferably using Bruker OPUS software.

Figure 18:
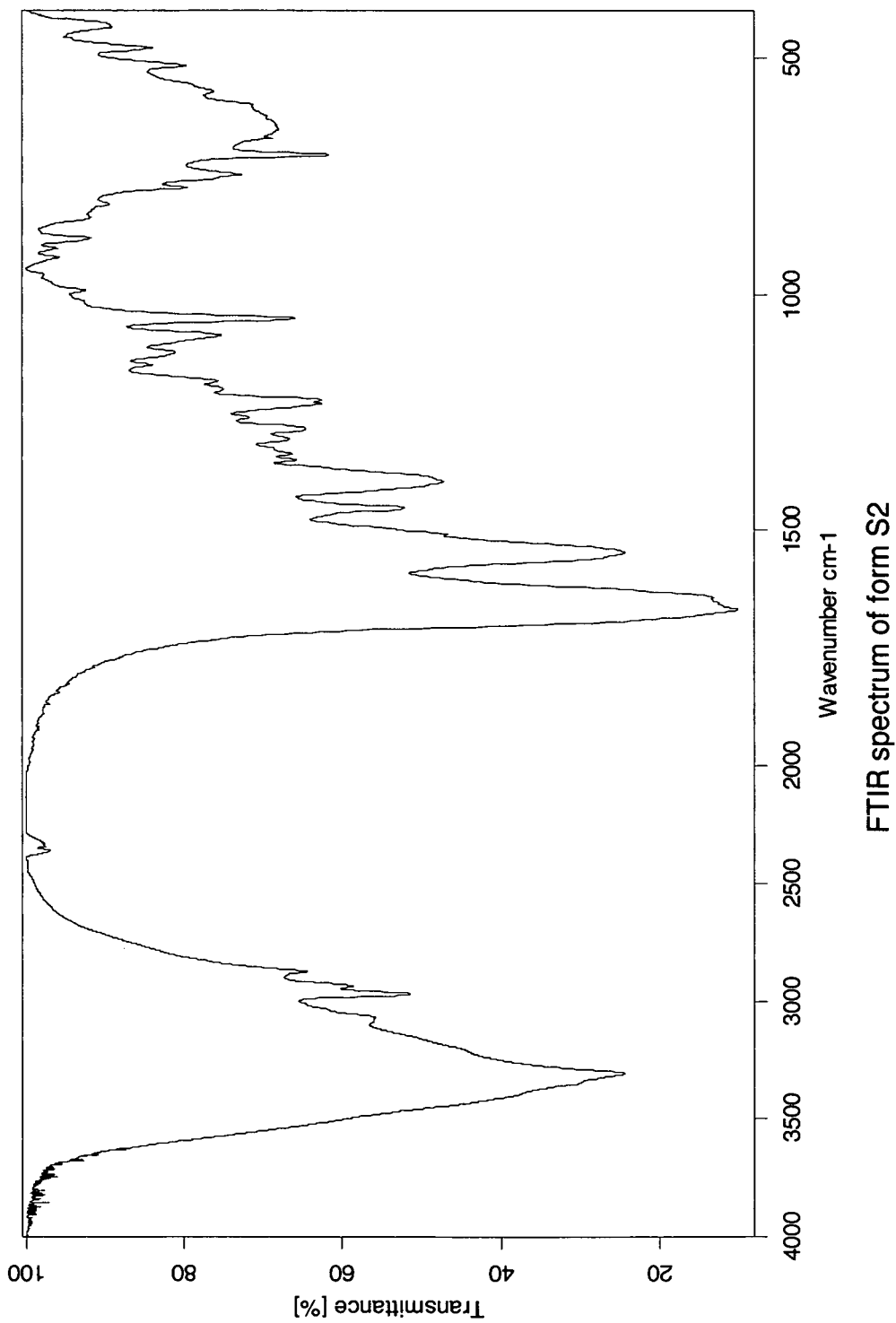
FIG. 18 depicts the FT-IR spectrum of crystalline form S2.

The FT-IR spectra of the tetrasolvates according to the invention and especially the crystalline form S2 is given in FIG. 18.

Preferably, the tetrasolvates according to the invention and, more preferably the Dihydrate-diethanolate, the Dihydrate-ethanolate, the Dihydrate-monoethanolate, the Diethanolate and/or the desolvates thereof, especially the crystalline form S2 can be characterised, alternatively or additionally, by the Raman-spectroscopy data comprising one or more of the band positions (±2 cm$^{-1}$) given below, more preferably comprising 5 or more of the band positions (±2 cm$^{-1}$) given below, even more preferably comprising 8 or more of the band positions (±2 cm$^{-1}$) given below, and especially comprising all the band positions (±2 cm$^{-1}$) given below, preferably together with the relative intensities given in brackets:
3068 cm$^{-1}$ (w), 2934 cm$^{-1}$ (s), 1668 cm$^{-1}$ (w), 1606 cm$^{-1}$ (w), 1449 cm$^{-1}$ (w), 1337 cm$^{-1}$ (w), 1204 cm$^{-1}$ (w), 1120 cm$^{-1}$ (w), 1004 cm$^{-1}$ (m), 904 cm$^{-1}$ (w), 825 cm$^{-1}$ (w), 624 cm$^{-1}$ (w), 521 cm$^{-1}$ (w).

More preferably, the tetrasolvates according to the invention, more preferably the Dihydrate-diethanolate, the Dihydrate-ethanolate, the Dihydrate-monoethanolate, the Diethanolate and/or the desolvates thereof, and especially the crystalline form S2 can be characterised, alternatively or additionally, by the Raman-spectroscopy data comprising one or more of the and positions (±2 cm$^{-1}$) given below, more preferably comprising 9 or more of the band positions (±2 cm$^{-1}$) given below, even more preferably comprising 12 or more of the band positions (±2 cm$^{-1}$) given below, and especially comprising all the band positions (±2 cm$^{-1}$) given below, preferably together with the relative intensities given in brackets:
3068 cm$^{-1}$ (w), 2934 cm$^{-1}$ (s), 1668 cm$^{-1}$ (w), 1606 cm$^{-1}$ (w), 1586 cm$^{-1}$ (w), 1449 cm$^{-1}$ (w), 1337 cm$^{-1}$ (w), 1204 cm$^{-1}$ (w), 1120 cm$^{-1}$ (w), 1033 cm$^{-1}$ (w), 1004 cm$^{-1}$ (m), 904 cm$^{-1}$ (w), 825 cm$^{-1}$ (w), 624 cm$^{-1}$ (w), 521 cm$^{-1}$ (w).

The relative intensities given in brackets are preferably defined as follows: "s"=strong (relative Raman intensity preferably ≥0.04), "m"=medium (preferably 0.04>relative Raman intensity≥0.02), "w"=weak (relative Raman intensity preferably <0.02)

The Raman or FT-Raman spectrum is preferably obtained using Aluminium-cups as sample holders for the respective solid material.

The Raman-spectroscopy data is preferably obtained by FT-Raman-spectroscopy, The Raman-spectroscopy data or FT-Raman-spectroscopy data is preferably obtained by standard techniques as described in the European Pharmacopeia 6$^{th}$ Edition chapter 2.02.48. For the measurement of the FT-Raman-spectra, preferably a Bruker RFS 100 spectrometer is used. FT-Raman spectra are preferably base-line corrected, preferably using Bruker OPUS software.

Figure 19:
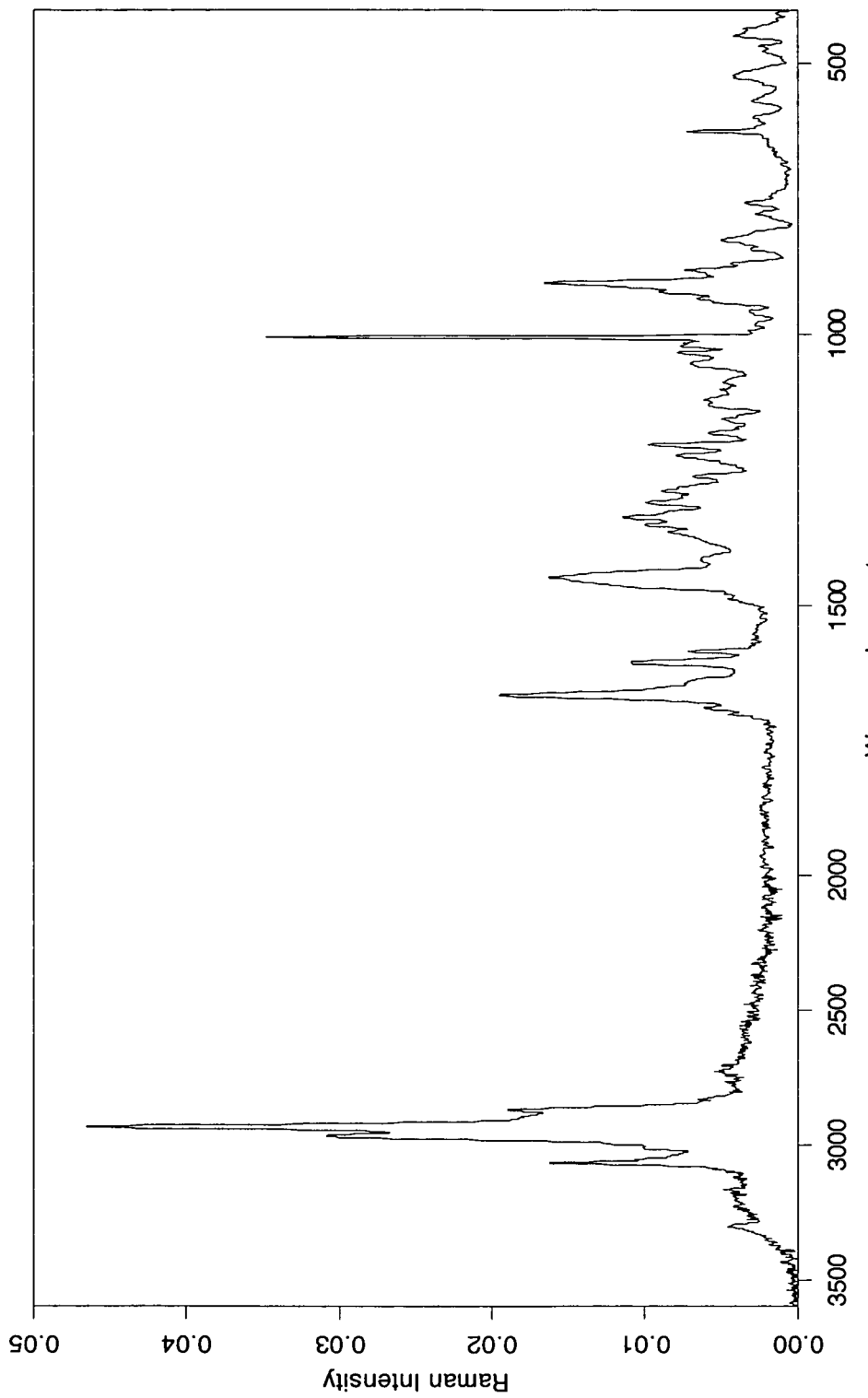
FIG. 19 depicts the FT-Raman spectrum of crystalline form S2.

The FT-Raman spectra of the tetrahydrates according to the invention, more preferably the Dihydrate-diethanolate, the Dihydrate-ethanolate, the Dihydrate-monoethanolate, the Diethanolate and/or the desolvates thereof, and especially the crystalline form S2 is given in FIG. 19.

Preferably, the tetrasolvates according to the invention, more preferably the Dihydrate-diethanolate, the Dihydrate-ethanolate, the Dihydrate-monoethanolate, the Diethanolate and/or the desolvates thereof, and especially the crystalline form S2 can be characterised, alternatively or additionally, by dynamic vapour experiments using water vapour and/or methanol vapour. The results can be obtained by standard techniques as described in Rolf Hilfiker, 'Polymorphism in the Pharmaceutical Industry', Wiley-VCH. Weinheim 2006 (Chapter 9: Water Vapour Sorption, and references therein).

Figure 20:
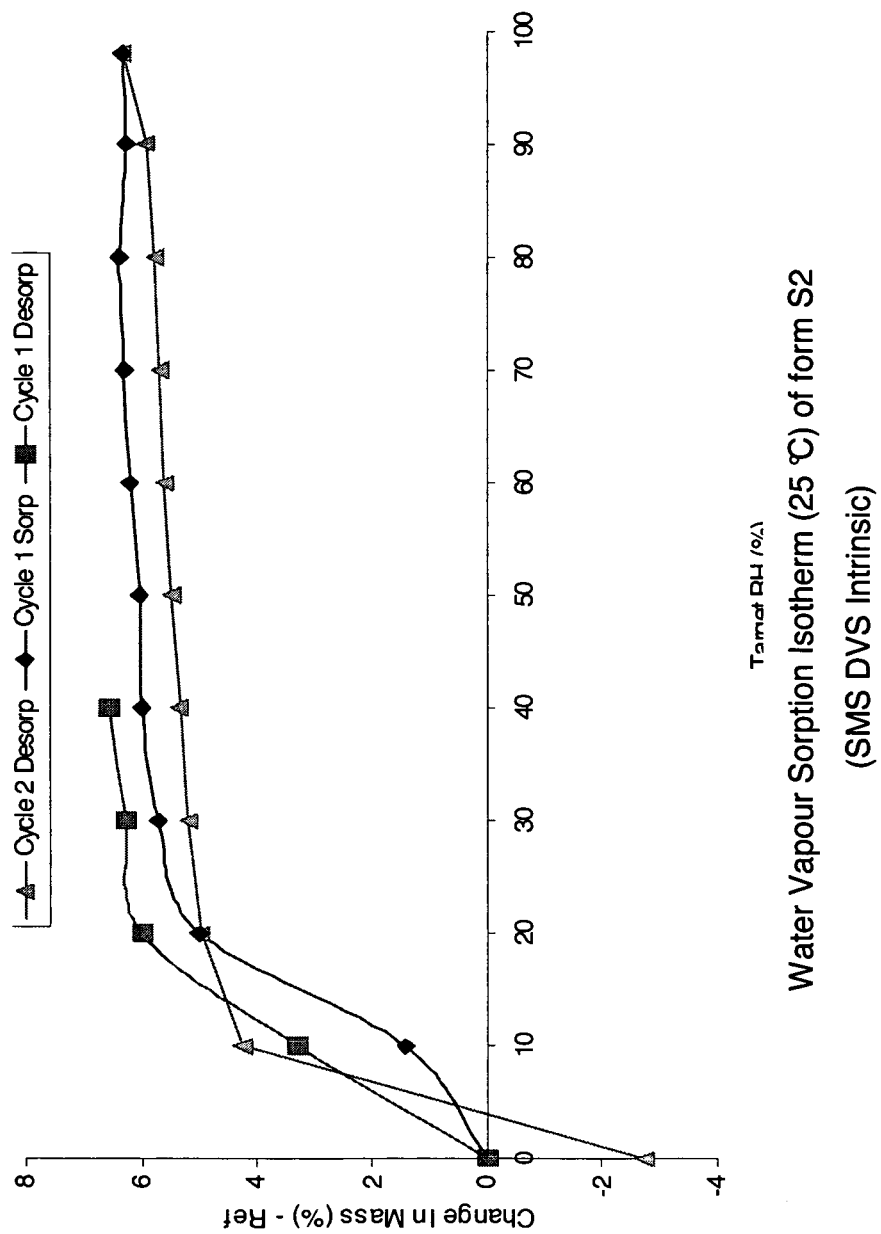
FIG. 20 depicts the water vapour sorption isotherm of crystalline form S2.

The Water Vapour Sorption behaviour of the tetrasolvates according to the invention, more preferably the Dihydrate-diethanolate, the Dihydrate-ethanolate, the Dihydrate-monoethanolate, the Diethanolate and/or the desolvates thereof, and especially the crystalline form S2 shows a mass loss of approx. 6.5 wt % in the first desorption cycle (which is lower than the observed Ethanol mass gain in the Ethanol Vapour Sorption experiment). Upon water vapour adsorption, an assembly of water molecules in the lattice is observed, with a maximum weight gain of approx. 6.4 wt % at elevated rh. In the second desorption cycle a total mass loss of approx. 9.2 wt % is observed. For a Dihydrate Di-Ethanolate of the compound of formula I, the calculated Ethanol content equals 12.5 wt %. Form S2 can be shown to be the thermodynamically stable form in an atmosphere of 100% Ethanol vapour. The Water Vapor Sorption isotherm (25° C.) of crystalline form S2 (SMS DVS Intrinsic) is given in FIG. 20. The Ethanol Vapour Sorption Isotherm (25° C.) of a hydrate form to form S2 (SMS DVS Advantage) is given in FIG. 21.

Figure 21:
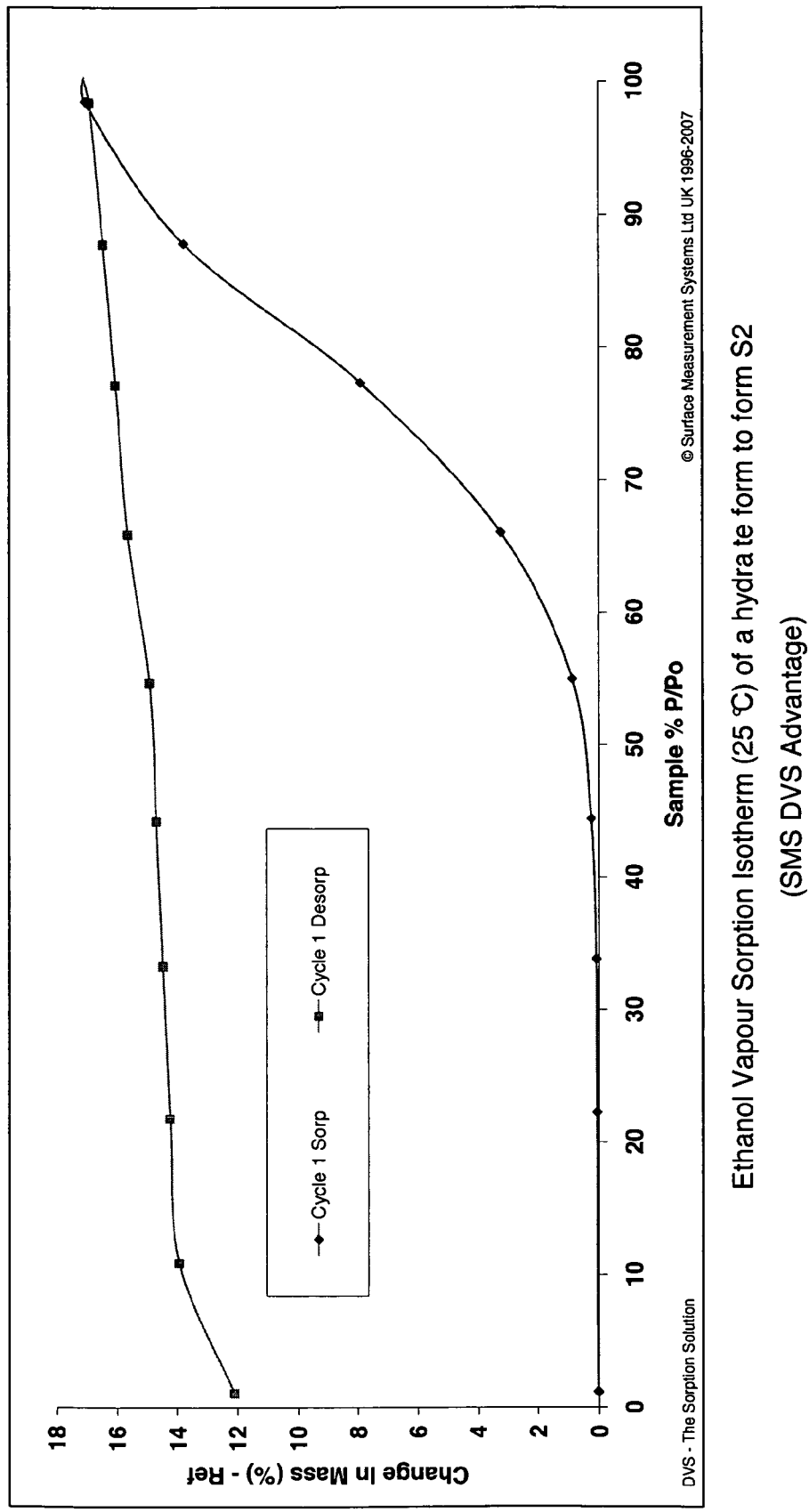
FIG. 21 depicts the ethanol vapour sorption isotherm of a hydrate form to form S2.

Thus, crystalline form S2 is a crystalline Ethanol solvate form or a mixed water/ethanol solvate form, preferably selected from the Dihydrate-ethanolate, the Dihydrate-monoethanolate, the Diethanolate and/or the desolvates thereof, which can be obtained e.g. via Ethanol Vapour Sorption, preferably via Ethanol Vapour Sorption starting with a hydrate structure, such as the hydrates according to the invention and especially the tetrahydrate according to the invention, i.e. crystalline form S3. From the Ethanol Vapour Sorption curve as shown in FIG. 21 and as discussed above, it can be seen that at elevated Ethanol partial pressure, approx. 17 wt % Ethanol are taken up by the sample.

As can be seen from the data given and discussed herein, the solvates and especially the tetrasolvates of the compound of formula I form a class of novel crystalline forms (further also to be named pseudopolymorphic forms or abbreviated PP) based on the same structural type, having highly similar physical properties and being easily convertible, preferably with potentially all transition forms being derivable and especially all transition forms between the pseudopolymorphic forms described herein being potentially derivable.

Figure 22:
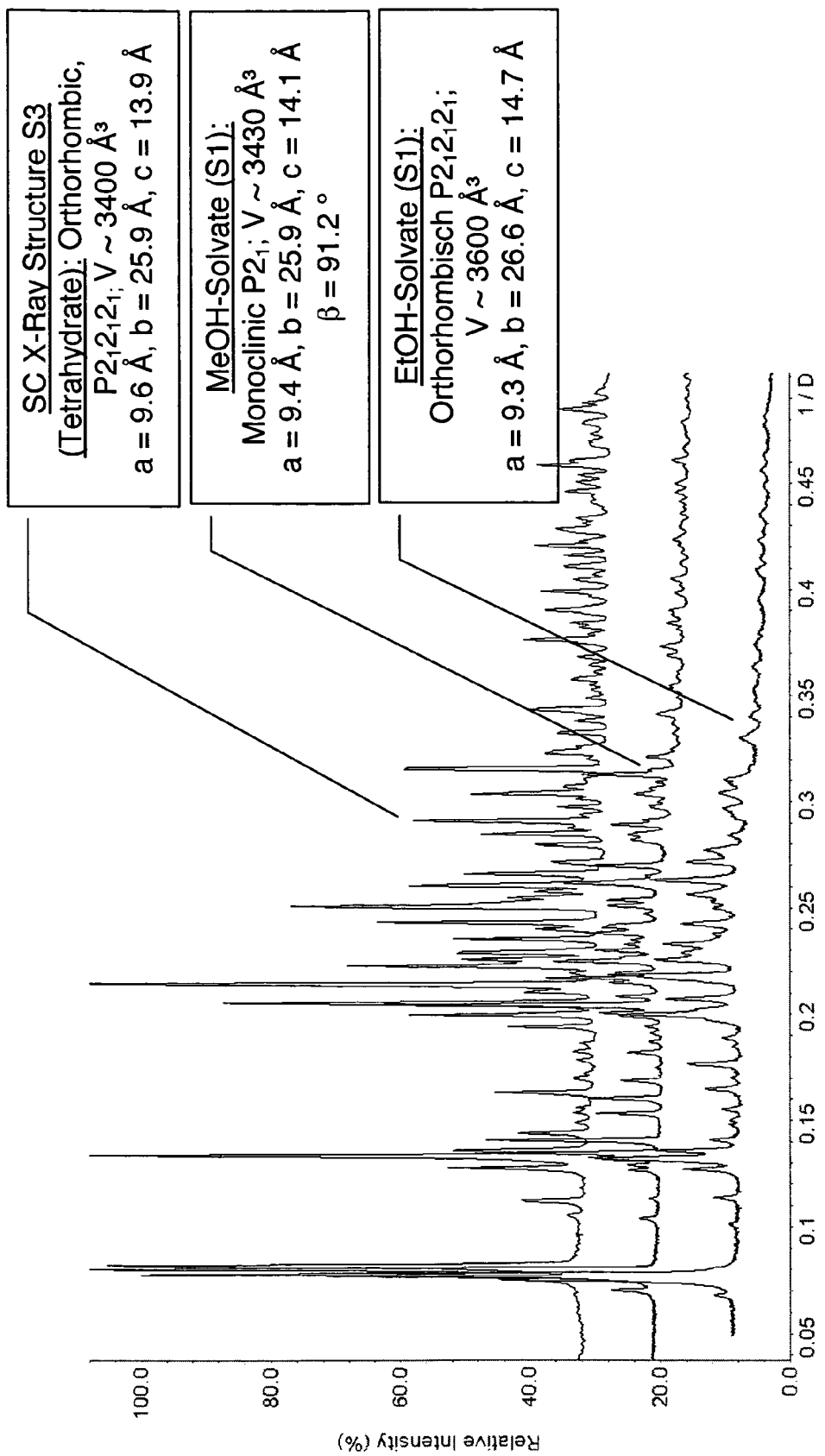
FIG. 22 depicts the PXRD comparision of crystalline forms S1, S2 and S3.

The similarity of the structural type is additionally shown by a superimposed plot of PXRD patterns of the three selected pseudopolymophs S1, S2 and S3 given in FIG. 22. It can be seen that all three selected pseudopolymorphs exhibit very similar PXRD patterns, and, moreover, lead to basically same unit cells, as a replacement of water by Methanol or Ethanol only leads to a slight expansion of the unit cells and thus to a slight increase in unit cell volume. As expected from the molar volumes of the solvents, this is more pronounced for the Ethanol solvate than for the Methanol solvate.

In the presence of alcohols, preferably Methanol and/or Ethanol, and/or water being present in different concentrations or partial pressures interconversion within the pseudopolymorphic class, comprising the solvates and especially the tetrasolvates according the invention, occurs easily. As alcohols, preferably Methanol and/or Ethanol, are useful solvents in the manufacturing process, usage of the pseudopolymorphs is preferably beneficial to obtain the compound of formula I in a crystalline solid-state modification exhibiting an advantageously high solubility combined with good crystallinity.

The solvates and especially the tetrasolvates within the pseudopolymorphic class or system are crystalline and preferably exhibit advantageous solid-state stability without loss of the Cilengitide host structure, in comparison to the previously described amorphous solid material. Said class of pseudopolymorphic forms described herein exhibit a surprisingly high solubility, especially in aqueous media, which makes them especially useful for preparation of liquid formulations. Additionally, said class of polymorphic forms show a advantageously reduced hygroscopicity in comparison to the previously known amorphous material.

Solubility of tetrahydrate Form S3 in different solvents:

| Solvent | Solubility |
|---|---|
| $H_2O$ | 21.6 mg/ml |
| physiological NaCl solution | 21.1 mg/ml |
| buffer pH 7.4 | 24.4 mg/ml |
| $H_2O$/MeOH (1:1) | 12.8 mg/ml |
| $H_2O$/EtOH (1:1) | 13.0 mg/ml |
| $H_2O$/iPrOH (1:1) | 22.9 mg/ml |
| $H_2O$/Acetone (1:1) | 22.7 mg/ml |
| $H_2O$/Acetonitrile (1:1) | 24.3 mg/ml |

The combination of reduced hygroscopicity, good solubility and good crystallinity leads to superior properties compared to the amorphous phase. In comparison, the purification, the handling and the processing of the amorphous material is very difficult, due to, e.g. the very high hygroscopicity and the low stability of the amorphous solid material.

Further, the pseudopolymorphic forms and/or the anhydrates or ansolvates according the invention show improved physical and/or chemical stability compared to the amorphous phase, preferably leading to a reduced formation of degradation products during storage, for example by hydrolysis. This improved hydrolytic stability of the solid material according to the invention and especially of the crystalline forms according to the invention is believed to be caused by the reduction of trace amounts of ionic impurities that are normally present in the amorphous material of prior art.

As a result, all those factors discussed herein are believed to account for the advantageously improved solid state stability of the solid material according to the invention, the crystalline forms according to the invention and especially of the solvates and/or anhydrates or ansolvates according to the invention.

Additionally, all those factors discussed herein are believed to account for the advantageously improved stability of the medicaments according to the invention that contain the solid material according to the invention, preferably the crystalline forms according to the invention and especially the solvates and/or anhydrates or ansolvates according to the invention, leading e.g. to a longer shelf life due to higher thermal and/or storage stability.

A preferred subject of the invention is a solid material as described above and/or below for the treatment of disorders.

Disorders in this regard are preferably selected from group consisting of cancerous disorders, angiogenesis or angiogenic disorders, autoimmune disorders, inflammatory disorders and ocular disorders, and more preferably from the group consisting of brain cancer, lung cancer, head and neck cancer, breast cancer and prostate cancer, and metastases thereof, arthritis, rheumatoid arthritis, psoriasis, retinopathy, diabetic retinopathy, atherosclerosis, macular degeneration and age related macular degeneration.

Especially preferred is a solid material as described above and/or below for the treatment of disorders, selected from cancerous disorders.

Especially preferred is a solid material as described above and/or below for the treatment of cancerous disorders, wherein the cancerous disorders are selected from the group consisting of brain cancer, lung cancer, head and neck cancer, breast cancer and prostate cancer, and metastases thereof.

A preferred subject of the instant invention is a method of treating cancerous disorders in a patient, comprising administering to said patient a solid material as described above and/or below.

Especially preferred is a method as described above, wherein the cancerous disorders are selected from one or more of the groups of disorders described above.

A preferred subject of the instant invention is the use of a solid material according to the invention for the manufacture of a medicament for the treatment of disorders. Preferably, the disorders are selected from one or more of the groups of disorders described above.

Thus, a preferred subject of the instant invention is the use of a solid material essentially consisting of or consisting of one or more crystalline forms according to the invention, for the manufacture of a medicament for the treatment of disorders, preferably disorders as described herein.

An even more preferred subject of the instant invention is the use of a solid material essentially consisting or consisting of one or more crystalline forms, selected from the group consisting of crystalline form A1, crystalline form S1, crystalline form S2 and crystalline form S3, and mixtures thereof, for the manufacture of a medicament for the treatment of disorders, preferably disorders as described herein.

Especially preferred subject of the instant invention is the use of a solid material especially consisting or consisting of crystalline form A1 or crystalline form S3, or mixtures thereof, for the manufacture of a medicament for the treatment of disorders, preferably disorders as described herein.

Surprisingly, the solid material according to the invention and especially the one or more crystalline forms according to the invention can be prepared by contacting the compound according to formula I with a solvent or solvent mixture, preferably a polar and/or protic solvent or solvent mixture.

Thus, a preferred subject of the instant invention is a process for the preparation or manufacture of the solid material according to the invention and especially for the preparation or manufacture of one or more of the crystalline forms according to the invention, comprising contacting a compound according to formula I with a solvent or solvent mixture, preferably a polar and/or protic solvent or solvent mixture, and isolating the solid material according to the invention obtained by said contacting from said solvent or solvent mixture.

Said isolation from said solvent or solvent is preferably achieved by i) crystallisation and/or precipitation of the solid material according to the invention from said solvent or solvent mixture, and/or ii) separating the solid material according to the invention from said solvent, preferably by physical means, such as filtration or centrifugation, or alternatively by sedimentation and/or decanting.

However, a plurality of separation techniques for achieving a solid/fluid separation are known in the art. Preferably, either one of them can be successfully applied for said separation.

Preferably, the solid material according to the invention and especially the one or more crystalline forms according to the invention can be prepared starting with a solid material of the compound according to formula I that is essentially free or preferably free of one or more of the crystalline forms according to the invention, and then by contacting it with a solvent or solvent mixture, preferably a polar and/or protic solvent or solvent mixture.

Alternatively preferably, the solid material according to the invention and especially the one or more crystalline forms according to the invention can be prepared starting with a solution of the compound according to formula I that is essentially free or preferably free of one or more of the crystalline forms according to the invention, and then by contacting it with a solvent or solvent mixture, preferably a polar and/or protic solvent or solvent mixture, or transferring said solution of the compound according to formula I that is essentially free or preferably free of one or more of the crystalline forms according to the invention into said solvent or solvent mixture, preferably said polar and/or protic solvent or solvent mixture.

Generally, to obtain the solid form according to the invention and/or one or more of the crystalline forms according to the invention, the contacting with said solvent or solvent mixture, preferably said polar and/or protic solvent or solvent mixture or the contact with said solvent or solvent mixture, preferably said polar and/or protic solvent or solvent mixture is followed by an isolating step, wherein the solid material according to the invention and/or one or more of the crystalline forms according to the invention can be obtained in a solid state.

Contacting or contact in this regard preferably means contacting in the broadest sense, such as "being in the presence of". Accordingly, examples of contacting or contact with said solvent or solvent mixture include, but are not limited to, dissolving or partly dissolving in said solvent or solvent mixture, suspending in said solvent or solvent mixture, stirring in the presence of said solvent or solvent mixture, triturating with or in the presence of said solvent or solvent mixture, allowing to stand in the presence of said solvent or solvent mixture, heating in the presence of said solvent or solvent mixture, cooling in the presence of said solvent or solvent mixture, crystallising or re-crystallising from said solvent or solvent mixture and/or precipitating from said solvent or solvent mixture.

Preferred ways of contacting or contact in this regard are preferably selected from a group consisting of: dissolving or partly dissolving in said solvent or solvent mixture, stirring in the presence of said solvent or solvent mixture, triturating with or in the presence of said solvent or solvent mixture, heating or cooling, preferably heating in the presence of said solvent or solvent mixture, crystallising or re-crystallising from said solvent or solvent mixture and/or precipitating from said solvent or solvent mixture.

An especially preferred way of contacting in this regard comprises dissolving, essentially dissolving or suspending the starting material of the compound of formula I and/or salts thereof in a (first) polar and/or protic solvent or solvent mixture, preferably followed by re-crystallising, crystallising and/or precipitating of the product formed from said solventor solvent mixture, which is preferably a solid material according to the invention. Preferably, re-crystallisation, crystallisation and/or precipitation of the product formed is induced or facilitated by cooling and/or the addition of further (or second) solvent or solvent mixture, preferably a further solvent or solvent mixture having a different polarity and more preferably having a lower polarity than the (first) solvent or solvent mixture in which the contacting was started.

Another especially preferred way of contacting in this regard comprises the formation of a slurry of the starting material of the compound of formula I as described above and/or below and a polar and/or protic solvent or solvent mixture, and stirring and/or agitating said slurry, preferably for a reaction time as described herein and a reaction temperature or processed temperature as described herein. This is preferably also referred to as "slurry conversion"

Suitable solvents and solvent mixtures for use in the methods and/or processes according to the invention are known in the art. Preferred solvents and solvent mixtures are preferably selected from the group consisting of organic solvents, water, saline, buffer solutions, and mixtures thereof. The terms "polar and/or protic solvent or solvent mixture" are known and clear to the ones skilled in the art.

Examples polar and/or protic solvents include, but are not limited to, water, saline or physiological NaCl solution, phosphate buffer solution, lower alcohols, such as monools, diols or triols having 1 to 6 carbon atoms, lower ketones, such as acetone or methyl ethly ketone, acetonitrile, propionitrile, DMF, DMSO, and the like. Preferred polar and/or protic solvents are selected from the group consisting of water, saline, methanol, ethanol, propanol, isopropanol, acetone, acetonitrile, propionitrile, DMF and DMSO.

Examples of polar and/or protic solvent mixtures include, but are not limited to, mixtures of the above given polar and/or protic solvents, more preferably mixtures of water with one or more of the above given polar and/or protic solvents other than water, mixtures of saline or physiological NaCl solution or phosphate buffer solution with one or more of the above given polar and/or protic solvents.

Preferred polar and/or protic solvent mixtures are selected from the group consisting of mixtures of water with methanol, ethanol and/or isopropanol, mixtures of methanol, ethanol and/or isopropanol, mixtures of acetone with water and/or acetonitrile, mixtures of methanol with acetone, acetonitrile and/or water, and mixtures of ethanol with acetone, acetonitrile, and preferably also selected from the above given mixtures, wherein the water is substituted for saline, physiological NaCl solution, or phosphate buffer solution. Preferred within said mixtures are mixtures comprising all preferably essentially consisting of 2, 3 or 4 of the given solvents. Especially preferred within said mixtures are mixtures that comprise at least 5% and especially at least 10% of each of the solvents contained in the mixture.

Examples of preferred solvents and/or solvent mixture in this regard are selected from the group consisting of water, methanol, ethanol, isopropanol, and mixtures thereof, more preferably selected from the group consisting of water, methanol, ethanol, and mixtures thereof.

In said method of manufacture of a solid material according to the invention, the starting material of compound of formula I is preferably selected from the group consisting of
a) amorphous or essentially amorphous material of the compound of formula I,
b) an acid-addition or a base-addition salt of the compound of formula I,
c) an amorphous or essentially amorphous solid material of an acid-addition or a base-addition salt of the compound of formula I, and
b) a solution of crude compound of formula I and/or an acid-addition or a base-addition salt thereof, preferably as obtained from the synthesis of said compound and/or salt thereof,
and mixtures thereof.

Additionally, it was surprisingly found that one first crystalline form according to the invention can be transformed into one or more other crystalline forms according to the invention, preferably reversibly. Furthermore, it was found that one first mixture of one or more crystalline forms according to the invention can be either transformed into a second mixture of crystalline forms according to the invention being different from said first mixture, or into a pure or essentially pure singer crystalline form according to the invention.

Accordingly, the invention also provides a process for transforming one first solid material according to the invention, comprising one or more first crystalline forms, into a second solid material according to the invention, comprising one or more second crystalline forms. This method can be preferably done in the same way and preferably using the same solvent and/or solvent mixtures as the method of manufacture described above and/or below, but is using a (first) solid material according to the invention as the starting material of the method.

Thus, a preferred subject of the instant invention is a process for the manufacture or the transformation, preferably manufacture, of a solid material according to the invention, comprising a) contacting cyclo-(Arg-Gly-Asp-DPhe-NMeVal) and/or an acid-addition or a base-addition salt thereof with a solvent or solvent mixture, preferably a polar and/or protic solvent or solvent mixture, b) precipitating and/or crystallising the internal salt of cyclo-(Arg-Gly-Asp-DPhe-NMe-Val) from a polar and/or protic solvent or solvent mixture, and c) optionally isolating a solid material according the invention.

In said process for the transformation, the starting material employed in step a) is preferably a (first) solid form according to the invention, containing cyclo-(Arg-Gly-Asp-DPhe-NMeVal) as the inner salt, and the solid material according to the invention obtained under step b) and optionally isolated according to step c) is a (second) different solid material according to the invention. Preferably, the difference between the first solid material according to the invention and the second different solid material according to the invention is the amount of crystalline forms contained in said second solid form, the selection of the crystalline forms contained in said solid form or the ratio of the crystalline forms contained in said solid form.

In said process for the manufacture, the starting material employed in step a) is preferably selected from i) a solid form of the compound of formula I different from the solid form according to the invention, ii) a solution of cyclo-(Arg-Gly-Asp-DPhe-NMeVal) and/or an acid-addition or a base-addition salt thereof, wherein the solution is preferably either a crude solution or obtained, more preferably directly obtained, from the synthesis of the cyclo-(Arg-Gly-Asp-DPhe-NMeVal), and/or iii) obtained from dissolving a solid form of the compound of formula I different from the solid form according to the invention.

Thus, a preferred subject of the instant invention is a process for the manufacture of a solid material according to the invention, comprising a) contacting an acid-addition or a base-addition salt of cyclo-(Arg-Gly-Asp-DPhe-NMeVal) with a polar and/or protic solvent or solvent mixture, b) precipitating and/or crystallising the internal salt of cyclo-(Arg-Gly-Asp-DPhe-NMeVal) from a polar and/or protic solvent or solvent mixture, and c) optionally isolating a solid material according the invention.

In said process for the manufacture and/or the transformation, step a), b) and/or c) is preferably performed at a pH value in the range of 5.5 to 8, more preferably at a pH value in the range of 6 to 7.5, more preferably at a pH value in the range of 6.5 to 7.2 and especially at a pH value in the range of 6.7 to 6.9, for example at a pH value of about 6.8. More preferably, two or more of the steps selected from a), b) and c) are performed at the pH values given above, and especially all the steps a), b) and c) are performed at the pH values given above. Performing one or more of the steps selected from a), b) and c) at the pH values given above is advantageous to convert an acid-addition or a base-addition salt of cyclo-(Arg-Gly-Asp-DPhe-NMeVal) into the inner salt of cyclo-(Arg-Gly-Asp-DPhe-NMeVal), or to maintain or stabilize the inner salt of cyclo-(Arg-Gly-Asp-DPhe-NMeVal) within said process.

In said process for the manufacture and/or the transformation, step a), b) and/or c) is preferably performed under about isoelectric conditions. More preferably, two or more of the steps selected from a), b) and c) are performed under about isoelectric conditions, and especially all the steps a), b) and c) are performed under about isoelectric conditions. Performing one or more of the steps selected from a), b) and c) under about isoelectric conditions is also advantageous to convert an acid-addition or a base-addition salt of cyclo-(Arg-Gly-Asp-DPhe-NMeVal) into the inner salt of cyclo-(Arg-Gly-Asp-DPhe-NMeVal), or to maintain or stabilize the inner salt of cyclo-(Arg-Gly-Asp-DPhe-NMeVal) within said process.

In said process for the manufacture and/or the transformation, step a), b) and/or c) is preferably performed at a temperature in the range between −20° C. and +200° C., more preferably in the range between −5° C. and +150° C., even more preferably in the range between +5° C. and +110° C. and especially in the range between +10° C. and +100° C., for example at about room temperature (about 25° C.), at about 50° C. or at about 75° C. or at about 100° C.

Generally, higher temperatures tend to accelerate the processes for the manufacture and/or the processes for the transformation as described herein.

Generally, temperatures at the higher end of the given temperature ranges tend to promote the formation the anhydrates or ansolvates according to the invention.

Generally, temperatures at the lower end of the given temperature ranges tend to promote the formation of the solvates according to the invention.

In the processes for the manufacture of the solid materials according to the invention and/or in the processes for the conversion or transformation of the solid materials according to the invention and/or to crystallise form according to the invention, the processing time or "reaction time", i.e. the time during which the contacting, the precipitation, the crystallization and/or the isolation preferably takes place is generally between five minutes to four weeks. Said processing time is preferably not a very crucial factor for the processes according to the invention since during the above given times, very little or no decomposition of the compound according to formula I takes place, especially within the preferred process parameters or process conditions described herein. Additionally, the product of the process, i.e. the solid material according to the invention, is generally stable under the conditions it is formed.

Accordingly, processing times preferably are the range of 10 minutes to three weeks, more preferably 15 minutes to one week, more preferably 30 minutes to 72 hours and especially one hour to 48 hours.

Processing times for the formation or conversion, preferably formation, of the anhydrates or ansolvates according to the invention, and especially for the formation of the crystalline form A1 are preferably in the range of one hour to three weeks, more preferably in the range of one hour to two weeks and especially in the range of one hour to 72 hours.

Processing times for the formation or conversion, preferably formation, of the solvates according to the invention, more preferably the tetrasolvates according to the invention, even more preferably the one or more crystalline forms S1, S2 and/or S3 and especially for the formation of the crystalline form S1 are preferably in the range of five minutes to three weeks, more preferably in the range of five minutes to one week, even more preferably in the range of five minutes to 48 hours and especially in the range of 10 minutes to 24 hours.

Generally, lower temperatures during said processes lead to longer processing times, as it is known in the art.

Generally, water, methanol and/or ethanol, and mixtures thereof are preferred polar and/or protic solvents or solvent mixtures for use in step a), b) and/or c) and especially for use in step a), b) and c).

In said process for the manufacture and/or the transformation, the solvent of step a), b) and/or c), preferably a), b) and c), essentially consists of water, methanol or ethanol.

Preferably, the same or essentially the same solvent or solvent mixture, preferably a polar and/or protic solvent or solvent mixture is used in process steps a), b) and c).

Generally, the use of solvent or solvent mixtures in step a), b) and/or c) that contain at least 5% by weight, more preferably at least 10% by weight and especially at least 20% by weight of one or more alcohols, preferably selected from methanol, ethanol and isopropanol, more preferably selected from methanol and ethanol, promote the formation of the solvates according to the invention.

More specifically, the use of solvent mixtures in step a), b) and/or c) that comprise
i) 5 to 90% by weight of at least one alcohol, selected from the group consisting of methanol and ethanol, and
ii) 10 to 95% by weight of water,
preferably promote the formation of the solvates according to the invention.

Even more specifically, the use of solvent mixtures in step a), b) and/or c) that comprise
i) 5 to 50% by weight and especially 10 to 60% by weight of at least one alcohol, preferably selected from the group consisting of methanol and ethanol, and
ii) 50 to 95% by weight and especially 40 to 90% by weight of water, preferably promote the formation of the solvates according to the invention.

Thus, preferred is a process as described above and/or below for the manufacture of a solid material according to the invention, preferably solvates according to the invention, and especially of one or more tetrasovates according to the invention, wherein the solvent or solvent mixture of step a), b) and/or c) comprises
i) 5 to 90% by weight, preferably 5 to 50% by weight, of at least one alcohol, selected from the group consisting of methanol and ethanol, and
ii) 10 to 95% by, weight preferably 50 to 95% by weight, of water.

Thus, preferred is a process as described above and/or below for the manufacture of a solid material according to the invention, preferably anhydrates or ansolvates according to the invention, and especially of crystalline form A1, wherein solvent of step a), b) and/or c) essentially consists of water, methanol and ethanol and more preferably essentially consists of water.

Thus, preferred is a process as described above and/or below for the manufacture of a solid material according to the invention, preferably anhydrates or ansolvates according to the invention, and especially of crystalline form A1, wherein steps a), b) and/or c) are performed at a temperature above +40° C., more preferably at a temperature of +50° or higher and especially at a temperature of +60° or higher.

Within the process parameters that are preferred for the formation of solvates and especially tetrasolvates according to the invention, an alcohol content at the lower end of the given ranges and/or a water content at the higher end of the given ranges promote the formation of the hydrates according to the invention. Alternatively, an alcohol content at the higher end of the given ranges and/or a water content at the lower end of the given ranges promote the formation of alcohol solvates.

Especially preferred solvates in this regard are the tetrasolvates, preferably selected from the tetrahydrate, the methanol solvates and the ethanol solvates, and mixed forms thereof, even more preferably selected from the tetrahydrate, the methanol solvate S1 and the ethanol solvate S2, and especially the tetrahydrate S3.

Thus, one preferred process for the manufacture of a solid material according to the invention comprises or preferably essentially consists of
i) crystallising or re-crystallising an amorphous material or an essentially amorphous material of the compound of formula I from a solvent or solvent mixture, preferably a polar and/or protic solvent or solvent mixture, preferably a solvent or solvent mixture, preferably a polar and/or protic solvent or solvent mixture as described herein, and optionally
ii) isolating the thus obtained solid material according to the invention from said solvent or solvent mixture by a solid/fluid separation technique, preferably a solid/fluid separation technique as described herein and especially by filtration.

Thus, one preferred process for the transformation of a first solid material according to the invention into a second solid material according to the invention comprises or preferably essentially consists of
a) precipitating, crystallising or re-crystallising a first solid material according to the invention from a solvent or solvent mixture, preferably a polar and/or protic solvent or solvent mixture, preferably a solvent or solvent mixture, preferably a polar and/or protic solvent or solvent mixture as described herein, and optionally
b) isolating the thus obtained second solid material according to the invention from said solvent or solvent mixture by a solid/fluid separation technique, preferably a solid/fluid separation technique as described herein and especially by filtration.

In the synthesis of the compound cyclo-(Arg-Gly-Asp-DPhe-NMe-Val), the final product or crude product of said synthesis is in many cases an acid-addition or a base-addition salt of the compound cyclo-(Arg-Gly-Asp-DPhe-NMe-Val), preferably an acid-addition salt of the compound cyclo-(Arg-Gly-Asp-DPhe-NMe-Val), e.g. the hydrochloride salt of cyclo-(Arg-Gly-Asp-DPhe-NMe-Val) (=cyclo-(Arg-Gly-Asp-DPhe-NMe-Val)×HCl), the trifluoroacetic acid salt of cyclo-(Arg-Gly-Asp-DPhe-NMe-Val) (=cyclo-(Arg-Gly-Asp-DPhe-NMe-Val)×TFA), the sulphate salt of cyclo-(Arg-Gly-Asp-DPhe-NMe-Val) (=cyclo-(Arg-Gly-Asp-DPhe-NMe-Val)×$SO_4$ or, more specifically cyclo-(Arg-Gly-Asp-DPhe-NMe-Val)×0.5 $SO_4$), or mixtures thereof.

Thus, preferred examples of processes for the manufacture of the solid material according to the invention start from said crude product in the form of acid-addition or a base-addition salts, preferably acid-addition salts.

Thus, a preferred subject of the instant invention is a process for the manufacture of a solid material according to the invention, comprising:
a) contacting an acid-addition or a base-addition salt, preferably an acid-addition salt, of the compound cyclo-(Arg-Gly-Asp-DPhe-NMe-Val) with a polar and/or protic solvent or solid mixture, preferably as defined herein, preferably by dissolving and/or suspending said salt in said solvent, b) converting said salt into the free base or preferably the internal salt of the compound cyclo-(Arg-Gly-Asp-DPhe-NMe-Val), preferably by adjusting the pH value, and c) crystallising and/or precipitating, and optionally isolating, the thus obtained solid material according to the invention from said solvent or solvent mixture.

Thus, a more preferred subject of the instant invention is a process for the manufacture of a solid material according to the invention, comprising:

a) contacting an acid-addition or a base-addition salt, preferably an acid-addition salt, of the compound cyclo-(Arg-Gly-Asp-DPhe-NMe-Val) with a solvent or solvent mixture, preferably a polar and/or protic solvent or solvent mixture, essentially consisting of or consisting of water, preferably by dissolving and/or suspending said salt in said solvent, b) converting said salt into the free base or preferably the internal salt of the compound cyclo-(Arg-Gly-Asp-DPhe-NMe-Val), preferably by adjusting the pH value, and c) preferably crystallising and/or precipitating, and optionally isolating, the thus obtained solid material according to the invention from said solvent or solvent mixture.

This process is advantageous for the manufacture of solid materials according to the invention that essentially consist of or preferably consist of the anhydrates or ansolvates according to the invention and especially essentially consist of or preferably consist of the crystalline form A1.

Thus, another more preferred subject of the instant invention is a process for the manufacture of a solid material according to the invention, comprising:

a) contacting an acid-addition or a base-addition salt, preferably an acid-addition salt, of the compound cyclo-(Arg-Gly-Asp-DPhe-NMe-Val) with a polar and/or protic solvent or solvent mixture, wherein said solvent or solvent mixture is selected from water and mixtures of 60 to 99.9% per weight water and 0.1 to 40% per weight of at least one alcohol, preferably selected from methanol and ethanol, and more preferably wherein said solvent or solvent mixture is water, preferably by dissolving and/or suspending said salt in said solvent or solvent mixture, b) converting said salt into the free base or preferably the internal salt of the compound cyclo-(Arg-Gly-Asp-DPhe-NMe-Val), preferably by adjusting the pH value, and c) crystallising and/or precipitating the thus obtained solid material according to the invention, preferably by adding alcohol, preferably methanol and/or ethanol, to said solvent or solvent mixture until the weight ratio between water and alcohol in the resulting solvent mixture is between about 1:1 and about 1:9, and optionally isolating said solid material from said resulting solvent mixture.

This process is advantageous for the manufacture of solid materials according to the invention that essentially consist of or preferably consist of the solvates according to the invention and especially essentially consist of or preferably consist of one or more of the crystalline forms S1, S2 and S3, preferably including mixed-water-alcohol solvates of various stoichiometries.

Preferred solvents or solvent mixtures, preferably polar and/or protic solvents or solid mixtures, pH values to be adjusted as well as temperatures for the above described processes are given and discussed herein.

A preferred example or embodiment of the process steps a), b) and/or c) is comprises the conditioning as described herein. More preferably, the contacting and/or converting steps can be regarded as conditioning or conditioning steps as described herein.

A preferred form of the process as described above comprises the conditioning or one or more conditioning steps as described herein.

A preferred form of the process as described above essentially consists of the conditioning or one or more conditioning steps as described herein.

Preferred parameters for a process for the manufacture of a solid according to the invention or a process for the transformation conversion of one or more crystalline forms according to the invention are presented by the below graphically depicted results of the following slurry conversion experiments.

Figure 37:
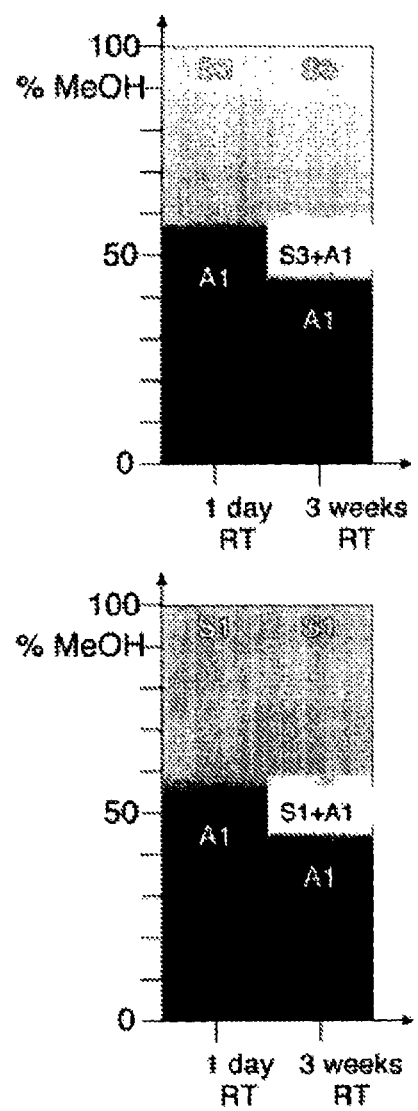
FIG. 37 shows the parameters and results of competitive slurries in MeOH/water-mixtures.

The first set of two diagrams shown in FIG. 37 shows the parameters and results of competitive slurries in MeOH/water-mixtures at RT (25° C.) as a function of the methanol content in the respective mixture and the respective processing time, i.e. after one day and after three weeks.

Figure 38:
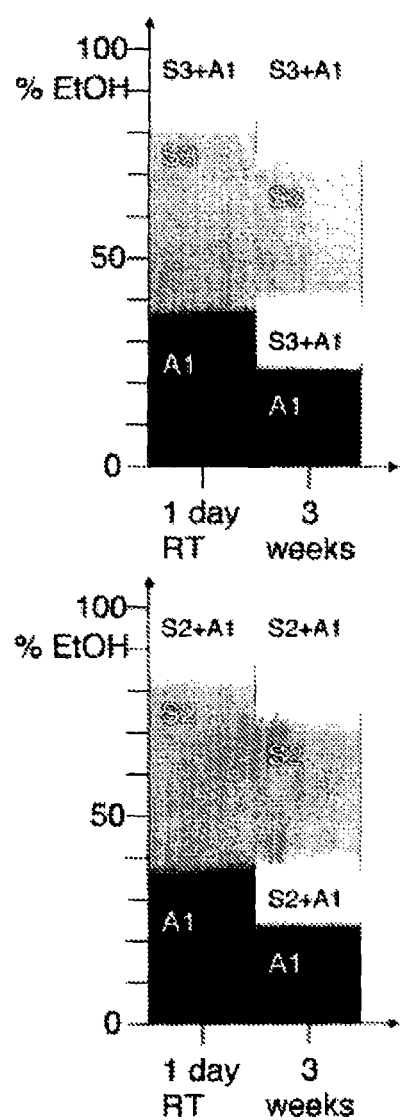
FIG. 38 shows the parameters and results of competitive slurries in EtOH/water-mixtures.

Based on additional PXRD investigations it has been shown that the residues obtained from the competitive slurries represented solvates including water and methanol. Accordingly, the residues have later been denominated S1 (indicated in the second diagram of FIG. 37) instead of S3 (indicated in the first diagram of FIG. 37). The set of two diagrams shown in FIG. 38 shows the parameters and results of competitive slurries in EtOH/water-mixtures at RT (25° C.) as a function of the ethanol content in the respective mixture and the respective processing time, i.e. after one day and after three weeks.

Based on additional PXRD investigations it has been shown that the residues obtained from the competitive slurries represented solvates including water and ethanol. Accordingly, the residues have later been denominated S2 (indicated in the second diagram of FIG. 38) instead of S3 (indicated in the first diagram of FIG. 38).

Especially preferred processes for the manufacture, processes for the transformation or conversion and additionally preferred temperatures, solvents, solvent mixtures, reaction times, starting materials and/or additional process parameters are given in the examples. Thus, the examples provide sufficient guidance, together with the description of the instant invention and/or the claims, to carry out the invention in its full breadth. However, processes and especially process parameters can be taken out of the examples, as well individually as in combinations of one or more of those processes and/or parameters, and used together with the disclosure in the description and/or claims.

Additionally, higher crystalline solvate forms could be obtained which contain up to about seven solvent molecules per molecule of the compound of formula I in the respective unit cells, and preferably the desolvates thereof. These higher crystalline solvate forms are preferably referred to as heptasolvates. The unit cell of these heptasolvates preferably contains about four molecules of the compound of formula I. Preferably, the solvent molecules contained in these heptasolvates are selected from water and alcohols and more preferably selected from water, methanol and ethanol, and mixtures thereof. Especially preferably, the solvent molecules in said heptasolvates consist essentially of water.

Thus, these higher crystalline solvate forms are preferably referred to as the heptasolvates (according to the invention), more preferably the heptahydrate (according to the invention), and the desolvates thereof, and especially as the crystalline form H1. The heptasolvates according to the invention are preferably characterised by a unit cell comprising of about four molecules of the compound according to formula I and up to about 7 solvent molecules per molecule of the compound of formula I. The heptasolvates according to the invention are more preferably represented by a unit cell comprising or preferably essentially consisting of about four molecules of the compound according to formula I and an upper limit of about 7 solvent molecules per molecule of the compound of formula I. Heptasolvates or heptahydrates according to the invention are preferably also the desolvates thereof, as long as the original crystal structure of the respective heptasolvate is essentially retained.

The heptasolvates according to the invention, more preferably the heptahydrates according to the invention and the desolvates thereof, and especially crystalline form H1 is preferably characterised, alternatively or additionally, by a unit cell with the unit cell lattice parameters (ULP) ULP3:

$a1=8.1\pm0.5$ Å, $b1=12.9\pm0.7$ Å and $c1=35.4\pm1.5$ Å, more preferably by a unit cell with the unit cell lattice parameters (ULP) ULP3:

$a1=8.1\pm0.3$ Å, $b1=12.9\pm0.5$ Å and $c1=35.4\pm1.0$ Å, and especially by a unit cell with the unit cell lattice parameters (ULP) ULP3:

$a1=8.1\pm0.1$ Å, $b1=12.9\pm0.1$ Å and $c1=35.4\pm0.1$ Å.

In the unit cell with lattice parameters ULP3, the angle $\alpha$ preferably is $90°\pm2°$, the angle $\beta$ preferably is $90°\pm2°$ and/or the angle $\gamma$ preferably is $90°\pm2°$.

Preferably, the unit cell with lattice parameters ULP3 can be characterised, alternatively or additionally, preferably additionally, by a content of about 4 molecules of the compound of formula I within said unit cell.

Preferably, the unit cell with lattice parameters ULP3 can be characterised, alternatively or additionally, preferably additionally, by an upper limit for the content of solvent molecules, preferably water molecules, of about 7 solvent molecules, preferably water molecules, per molecule of the compound of formula I within said unit cell.

Thus, said unit cell can preferably characterised, alternatively or additionally, by a total content of about four molecules of the compound of formula I and a total content or upper limit of 28 solvent molecules, preferably water molecules.

In the unit cell with lattice parameters ULP3, the angle $\alpha$ preferably is $90°\pm0.5°$, the angle $\beta$ preferably is $90°\pm0.5°$ and/or the angle $\gamma$ preferably is $90°\pm0.5°$. In the unit cell with lattice parameters ULP3, the angles $\alpha$, $\beta$ and $\gamma$ more preferably are $90°\pm0.1°$.

The heptasolvates according to the invention, more preferably the heptahydrates according to the invention and the desolvates thereof, and especially crystalline form H1 can be characterised, alternatively or additionally, by a melting/decomposition temperature.

The melting/decomposition temperatures and/or thermal behaviors can be preferably determined by DSC (Differential Scanning Calorimetry) and TGA (ThermoGravimetric Analysis). DSC and/or TGA methods or generally thermoanalysis methods and suitable devices for determining them are known in the art, for examples from European Pharmacopeia $6^{th}$ Edition chapter 2.02.34, wherein suitable standard techniques are described. More preferably, for the melting/decomposition temperatures or behaviors and/or the thermoanalysis in general, a Mettler Toledo DSC 821 and/or Mettler Toledo TGA 851 can be used, preferably as described in the European Pharmacopeia $6^{th}$ Edition chapter 2.02.34.

Preferably, the heptasolvates according to the invention, more preferably the heptahydrates according to the invention and the desolvates thereof, and especially crystalline form H1, can be characterised, alternatively or additionally, by Single Crystal X-Ray Structure Data, for example Single Crystal X-Ray Structure Data obtained on a diffractometer preferably equipped with a graphite monochromator and CCD Detector, preferably using Mo $K_\alpha$ radiation, preferably at a temperature of 302 K±5 K, and even more preferably on a XCalibur diffractometer from Oxford Diffraction equipped with graphite monochromator and CCD Detector using Mo $K_\alpha$ radiation at about 302 K.

According to the Single Crystal X-Ray Structure Data obtained, the heptasolvates according to the invention, more preferably the heptahydrates according to the invention and the desolvates thereof, and especially crystalline form H1 crystallises in the orthorhombic space group P $2_1\ 2_1\ 2_1$ with the lattice parameters a=8.1±0.1 Å, b=12.9±0.1 Å, c=35.4±0.1 Å, and the unit cell volume preferably is 3728 (±50) Å$^3$.

Even more preferably, a=8.135±0.001 Å, b=12.936±0.001 Å, and c=35.435±0.001 Å.

From the single crystal structure it is obvious that form H1 represents a heptasolvate and more specifically a heptahydrate.

Figure 33:
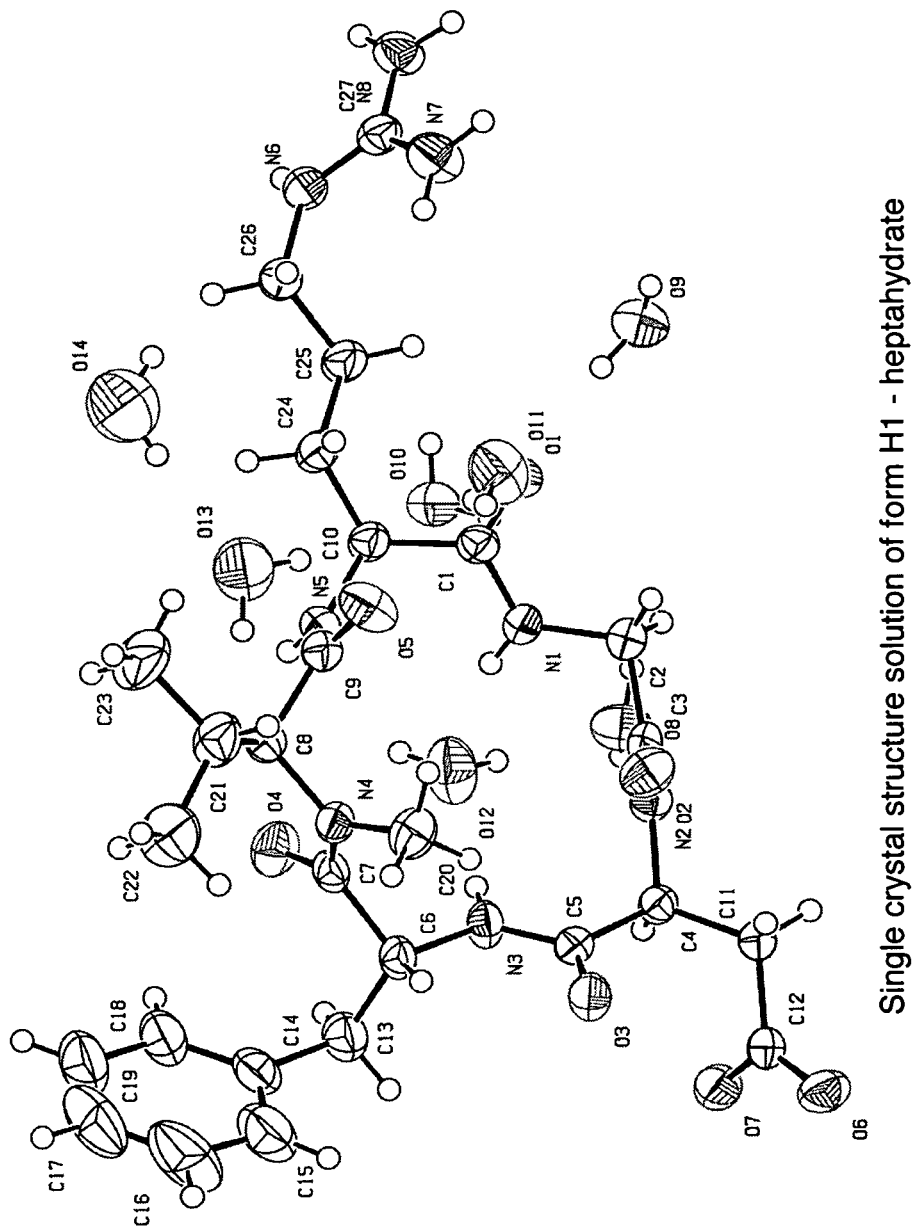
FIG. 33 depicts the single crystal structure solution of crystalline form H1.

The Single Crystal X-Ray Structure is depicted in FIG. 33.

The heptasolvates according to the invention, more preferably the heptahydrates according to the invention and the desolvates thereof, and especially crystalline form H1 can be characterised, alternatively or additionally, by Powder X-Ray Diffraction.

Preferably, the heptasolvates according to the invention, more preferably the heptahydrates according to the invention and the desolvates thereof, and especially crystalline form H1 can be characterised, alternatively or additionally, by Powder X-Ray Diffraction and more preferably by the Powder X-Ray Diffraction pattern comprising one or more of the Powder X-ray peaks given below, more preferably comprising 3 or more of the Powder X-ray peaks given below, even more preferably 6 or more of the Powder X-ray peaks given below, and especially comprising all of the of the Powder X-ray peaks given below:

| No. | D ± 0.1 [Å] | °2θ (Cu—K$\alpha_1$ radiation) ± 0.1° | Miller indices h | k | l |
| --- | --- | --- | --- | --- | --- |
| 1 | 17.7 | 5.0 | 0 | 0 | 2 |
| 3 | 10.4 | 8.5 | 0 | 1 | 2 |
| 5 | 7.4 | 12.0 | 1 | 0 | 2 |
| 6 | 7.3 | 12.1 | 0 | 1 | 4 |
| 8 | 6.8 | 13.1 | 1 | 1 | 1 |
| 9 | 6.7 | 13.2 | 1 | 0 | 3 |
| 11 | 5.9 | 14.9 | 1 | 1 | 3 |
| 12 | 5.4 | 16.3 | 1 | 1 | 4 |
| 13 | 5.0 | 17.7 | 1 | 2 | 1 |

-continued

| No. | D ± 0.1 [Å] | °2θ (Cu—Kα₁) radiation) ± 0.1° | Miller indices h | k | l |
|---|---|---|---|---|---|
| 15 | 4.7 | 19.1 | 1 | 2 | 3 |
| 18 | 4.0 | 22.4 | 2 | 0 | 2 |
| 21 | 3.4 | 26.1 | 0 | 1 | 10 |

More preferably, the heptasolvates according to the invention, more preferably the heptahydrates according to the invention and the desolvates thereof, and especially crystalline form H1 can be characterised, alternatively or additionally, by Powder X-Ray Diffraction and more preferably by the Powder X-Ray Diffraction pattern comprising one or more of the Powder X-ray peaks given below, more preferably comprising 5 or more of the Powder X-ray peaks given below, even more preferably 9 or more of the Powder X-ray peaks given below, and especially comprising all of the of the Powder X-ray peaks given below:

| No. | D [Å] | °2θ (Cu—Kα₁ radiation) ± 0.1° | Miller indices h | k | l |
|---|---|---|---|---|---|
| 1 | 17.7 | 5.0 | 0 | 0 | 2 |
| 2 | 12.2 | 7.3 | 0 | 1 | 1 |
| 3 | 10.4 | 8.5 | 0 | 1 | 2 |
| 4 | 8.9 | 10.0 | 0 | 0 | 4 |
| 5 | 7.4 | 12.0 | 1 | 0 | 2 |
| 6 | 7.3 | 12.1 | 0 | 1 | 4 |
| 7 | 6.9 | 12.8 | 1 | 1 | 0 |
| 8 | 6.8 | 13.1 | 1 | 1 | 1 |
| 9 | 6.7 | 13.2 | 1 | 0 | 3 |
| 10 | 6.4 | 13.8 | 1 | 1 | 2 |
| 11 | 5.9 | 14.9 | 1 | 1 | 3 |
| 12 | 5.4 | 16.3 | 1 | 1 | 4 |
| 13 | 5.0 | 17.7 | 1 | 2 | 1 |
| 15 | 4.7 | 19.1 | 1 | 2 | 3 |
| 17 | 4.1 | 21.8 | 1 | 1 | 7 |
| 18 | 4.0 | 22.4 | 2 | 0 | 2 |
| 19 | 3.9 | 22.8 | 1 | 0 | 8 |
| 21 | 3.4 | 26.1 | 0 | 1 | 10 |
| 22 | 3.4 | 26.2 | 2 | 1 | 5 |

Even more preferably, the heptasolvates according to the invention, more preferably the heptahydrates according to the invention and the desolvates thereof, and especially crystalline form H1 can be characterised, alternatively or additionally, by Powder X-Ray Diffraction and more preferably by the Powder X-Ray Diffraction pattern comprising one or more of the Powder X-ray peaks given below, more preferably comprising 8 or more of the Powder X-ray peaks given below, even more preferably 10 or more of the Powder X-ray peaks given below, and especially comprising all 12 of the of the Single Crystal X-ray peaks given below:

| No. | D ± 0.1 [Å] | °2θ (Cu—Kα₁) radiation) ± 0.1° | Miller indices h | k | L |
|---|---|---|---|---|---|
| 1 | 17.7 | 5.0 | 0 | 0 | 2 |
| 2 | 12.2 | 7.3 | 0 | 1 | 1 |
| 3 | 10.4 | 8.5 | 0 | 1 | 2 |
| 4 | 8.9 | 10.0 | 0 | 0 | 4 |
| 5 | 7.4 | 12.0 | 1 | 0 | 2 |
| 6 | 7.3 | 12.1 | 0 | 1 | 4 |
| 7 | 6.9 | 12.8 | 1 | 1 | 0 |
| 8 | 6.8 | 13.1 | 1 | 1 | 1 |
| 9 | 6.7 | 13.2 | 1 | 0 | 3 |
| 10 | 6.4 | 13.8 | 1 | 1 | 2 |
| 11 | 5.9 | 14.9 | 1 | 1 | 3 |
| 12 | 5.4 | 16.3 | 1 | 1 | 4 |
| 13 | 5.0 | 17.7 | 1 | 2 | 1 |
| 14 | 4.7 | 18.8 | 0 | 1 | 7 |
| 15 | 4.7 | 19.1 | 1 | 2 | 3 |
| 16 | 4.1 | 21.6 | 1 | 2 | 5 |
| 17 | 4.1 | 21.8 | 1 | 1 | 7 |
| 18 | 4.0 | 22.4 | 2 | 0 | 2 |
| 19 | 3.9 | 22.8 | 1 | 0 | 8 |
| 20 | 3.9 | 23.0 | 2 | 1 | 1 |
| 21 | 3.4 | 26.1 | 0 | 1 | 10 |
| 22 | 3.4 | 26.2 | 2 | 1 | 5 |
| 23 | 3.4 | 26.3 | 2 | 2 | 2 |

The Powder X-Ray Diffraction and more preferably the Powder X-Ray Diffraction pattern can preferably be performed or determined as described herein and especially performed or determined by standard techniques as described in the European Pharmacopeia 6$^{th}$ Edition chapter 2.9.33, and is even more preferably obtained with the parameters Cu—Kα₁ radiation and/or λ=1.5406 Å, preferably on a Stoe StadiP 611 KL diffractometer.

Preferably, the heptasolvates according to the invention, more preferably the heptahydrates according to the invention and the desolvates thereof, and especially crystalline form H1, can be characterised, alternatively or additionally, by the infrared-spectroscopy data. The IR-spectroscopy data can be preferably obtained by FT-IR-spectroscopy, The IR-spectroscopy data or FT-IR-spectroscopy data can be preferably obtained by standard techniques as described in the European Pharmacopeia 6$^{th}$ Edition chapter 2.02.24. For the measurement of the FT-IR-spectra, preferably a Bruker Vector 22 spectrometer can be used. FT-IR spectra are preferably baseline corrected, preferably using Bruker OPUS software.

Preferably, the heptasolvates according to the invention, more preferably the heptahydrates according to the invention and the desolvates thereof, and especially crystalline form H1, can be characterised, alternatively or additionally, by the Raman-spectroscopy data.

The Raman or FT-Raman spectrum is preferably obtained using Aluminium-cups as sample holders for the respective solid material.

The Raman-spectroscopy data is preferably obtained by FT-Raman-spectroscopy, The Raman-spectroscopy data or FT-Raman-spectroscopy data can be preferably obtained by standard techniques as described in the European Pharmacopeia 6$^{th}$ Edition chapter 2.02.48. For the measurement of the FT-Raman-spectra, preferably a Bruker RFS 100 spectrometer can be used. FT-Raman spectra are preferably baseline corrected, preferably using Bruker OPUS software.

Preferably, the heptasolvates according to the invention, more preferably the heptahydrates according to the invention and the desolvates thereof, and especially crystalline form H1, can be characterised, alternatively or additionally, by dynamic vapour sorption experiments. The results can be obtained by standard techniques as described in Rolf Hilfiker, 'Polymorphism in the Pharmaceutical Industry', Wiley-VCH. Weinheim 2006 (Chapter 9: Water Vapour Sorption, and references therein).

Thus, a preferred subject of the instant invention is a solid material of a compound according to formula I, cyclo-(Arg-Gly-Asp-DPhe-NMeVal)      (I)

wherein said solid material comprises one or more crystalline forms of the compound of formula I, characterised by a unit cell with the lattice parameters lattice parameters (ULP) ULP3:

$a1 = 8.1 \pm 0.5$ Å, $b1 = 12.9 \pm 0.7$ Å and $c1 = 35.4 \pm 1.5$ Å, more preferably by a unit cell with the unit cell lattice parameters (ULP) ULP3:

$a1 = 8.1 \pm 0.3$ Å, $b1 = 12.9 \pm 0.5$ Å and $c1 = 35.4 \pm 1.0$ Å, and especially by a unit cell with the unit cell lattice parameters (ULP) ULP3:

$a1 = 8.1 \pm 0.1$ Å, $b1 = 12.9 \pm 0.1$ Å and $c1 = 35.4 \pm 0.1$ Å.

Said unit cell is preferably a crystallographic unit cell or a crystallographically determined unit cell.

In said unit cell, the angle α preferably is 90°±2°, the angle β preferably is 90°±2° and/or the angle γ preferably is 90°±2°.

Preferably, the solid material comprises at least 10% by weight, more preferably at least 30% by weight, even more preferably 60% by weight and especially at least 90% by weight or at least 95% by weight, of one or more crystalline forms of the compound of formula I as defined above and/or below. For example, the solid material comprises about 25, about 50, about 75, about 95, about 99 or about 100% by weight of one or more crystalline forms of the compound of formula I as defined above and/or below.

Especially preferably, the solid material comprises at least 10 mole %, more preferably at least 30 mole %, even more preferably 60 mole % and especially at least 90 mole % or at least 95 mole %, of one or more crystalline forms of the compound of formula I as defined above and/or below. For example, the solid material comprises about 25, about 50, about 75, about 95, about 99 or about 100 mole % of one or more crystalline forms of the compound of formula I as defined above and/or below.

Especially preferred is a solid material as defined above that comprises the crystalline form H1 or a desolvate thereof, wherein the crystalline form H1 is characterised by one or more of the parameters given herein, said parameters preferably including the unit cell parameters ULP3 as given herein.

Especially preferred is a solid material as defined above that essentially consists of the crystalline form H1 or a desolvate thereof, wherein the crystalline form H1 is characterised by one or more of the parameters given herein, said parameters preferably including the unit cell parameters ULP3 as given herein.

Another preferred subject of the invention is thus a solid material that comprises one or more, preferably one, two, three or four, even more preferably one or two, crystalline forms of the compound of formula I, each having a unit cell with lattice parameters (ULP) selected from a group consisting of

ULP1:

$a1 = 9.5 \pm 0.5$ Å, $b1 = 26.0 \pm 1.5$ Å, and $c1 = 14.3 \pm 0.7$ Å,

ULP2:

$a2 = 9.8 \pm 0.5$ Å, $b2 = 20.0 \pm 1.5$ Å, and $c2 = 15.4 \pm 0.7$ Å, and

ULP3:

$a3 = 8.1 \pm 0.5$ Å, $b3 = 35.4 \pm 1.5$ Å, and $c3 = 12.9 \pm 0.7$ Å.

More preferably, the solid material comprises one or more, preferably one, two, three or four, even more preferably one or two, crystalline forms of the compound of formula I, each having a unit cell with lattice parameters (ULP) selected from a group consisting of

ULP1:

$a1 = 9.5 \pm 0.3$ Å, $b1 = 26.0 \pm 1.0$ Å, and $c1 = 14.3 \pm 0.5$ Å,

ULP2:

$a2 = 9.8 \pm 0.3$ Å, $b2 = 20.0 \pm 1.0$ Å, and $c2 = 15.4 \pm 0.5$ Å and

ULP3:

$a3 = 8.1 \pm 0.5$ Å, $b3 = 35.4 \pm 1.5$ Å, and $c3 = 12.9 \pm 0.7$ Å.

In the unit cell with lattice parameters ULP1, ULP2 and/or ULP3, the angle α preferably is 90°±2°, the angle β preferably is 90°±2° and/or the angle γ preferably is 90°±2°.

Preferably, the unit cell with lattice parameters ULP1, ULP2 and/or ULP3 can be characterised, alternatively or additionally, preferably additionally, by a content of about 4 molecules of the compound of formula I within said unit cell.

In the unit cell with lattice parameters ULP2 and/or ULP3, the angle α preferably is 90°±0.5°, the angle β preferably is 90°±0.5° and/or the angle γ preferably is 90°±0.5°. In the unit cell with lattice parameters ULP2 and/or ULP3, the angles α, β and γ more preferably are 90°±0.1°.

Preferably, the unit cell with lattice parameters ULP1, ULP2 and/or ULP3 can be characterised, alternatively or additionally, preferably additionally, by a content of about 4 molecules of the compound of formula I within said unit cell.

Preferably, the unit cell with lattice parameters ULP3 can be characterised, alternatively or additionally, preferably additionally, by a content of about 4 molecules of the compound of formula I within said unit cell.

More preferably, the solid material comprises one or more, preferably one, two, three or four, even more preferably one or two, crystalline forms of the compound of formula I, selected from
crystalline form A1, characterised by a unit cell with the lattice parameters a=9.8±0.1 Å, b=19.5±0.5 Å, and c=15.4±0.1 Å,
crystalline form S1, characterised by a unit cell with the lattice parameters a=9.4±0.1 Å, b=25.9±0.5 Å, and c=14.1±0.1 Å,
crystalline form S2, characterised by a unit cell with the lattice parameters a=9.3±0.1 Å, b=26.6±0.5 Å, and c=14.7±0.1 Å,
crystalline form S3, characterised by a unit cell with the lattice parameters a=9.6±0.1 Å, b=25.9±0.5 Å, and c=13.9±0.1 Å, and
crystalline form H1, characterised by a unit cell with the lattice parameters a=8.1±0.3 Å, b=35.4±1.0 Å, and c=12.9±0.5 Å

More preferably, the solid material comprises one or more, preferably one, two, three or four, even more preferably one or two, crystalline forms of the compound of formula I, selected from
crystalline form A1, characterised by a unit cell with the lattice parameters a=9.8±0.1 Å, b=19.5±0.5 Å, and c=15.4±0.1 Å, preferably with α=β=γ=90°±1° and especially with α=β=γ=90°;
crystalline form S1, characterised by a unit cell with the lattice parameters a=9.4±0.1 Å, b=25.9±0.5 Å, and c=14.1±0.1 Å, preferably with α=β=γ=90°±2°, and especially with α=90°±1°, β=91°±1, γ=90°±1° and especially with α=90°, β=91.2°, γ=90°;
crystalline form S2, characterised by a unit cell with the lattice parameters a=9.3±0.1 Å, b=26.6±0.5 Å, and c=14.7±0.1 Å, preferably with α=β=γ=90°±1° and especially with α=β=γ=90°; and
crystalline form S3, characterised by a unit cell with the lattice parameters a=9.6±0.1 Å, b=25.9±0.5 Å, and c=13.9±0.1 Å, preferably with α=β=γ=90°±1° and especially with α=β=γ=90°; and
crystalline form H1, characterized by a unit cell with the lattice parameters a=8.1±0.3 Å, b=35.4±1.0 Å, and c=12.9±0.5 Å, preferably with α=β=γ=90°±1° and especially with α=β=γ=90°

Preferably, the crystalline forms S1, S2 S3 and/or H1 can be characterised, alternatively or additionally, preferably additionally, by a content of about 4 molecules of the compound of formula I within said unit cells.

The crystalline forms S1, S2, S3 and/or H1 are preferably further characterised as solvates.

More preferably, the crystalline form H1 is further characterised as heptasolvate.

In the context of the present invention, solvates and/or heptasolvates preferably are crystalline solid adducts containing either stoichiometric or non-stoichiometric amounts of a solvent incorporated within the crystal structure, i.e. the solvent molecules preferably form a part of the crystal structure. If the incorporated solvent is water, the solvates are also commonly known as hydrates.

As a result, the solvent in the solvates preferably forms a part of the crystal structure and thus is in general detectable by X-ray methods and preferably detectable by X-ray methods as described herein.

Preferably, one or more claims 3 to 8 regarding the solid materials and the disclosure thereto as described herein for solid materials comprising one more crystalline forms as described herein other than crystalline form H1 are preferably also applicable to crystalline form H1 and/or solid materials comprising crystalline form H1. Especially preferred solid materials in this regard are subject of the claims 3 to 8 in this application, preferably including preferred embodiments given in the description in this regard.

Preferably, one or more methods of treating and the disclosure thereto as described herein for solid materials comprising one more crystalline forms as described herein other than crystalline form H1 is preferably also applicable to crystalline form H1 and/or solid materials comprising crystalline form H1. Especially preferred methods of treating in this regard are subject of the methods of treating claims in this application, preferably including preferred embodiments given in the description in this regard.

Preferably, one or more processes and the disclosure thereto as described herein for solid materials comprising one more crystalline forms as described herein other than crystalline form H1 is preferably also applicable to crystalline form H1 and/or solid materials comprising crystalline form H1. Especially preferred processes in this regard are subject of the process claims in this application, preferably including preferred embodiments given in the description in this regard.

Preferably, one or more uses and the disclosure thereto as described herein for solid materials comprising one more crystalline forms as described herein other than crystalline form H1 is preferably also applicable to crystalline form H1 and/or solid materials comprising crystalline form H1. Especially preferred uses in this regard are subject of the use claims in this application, preferably including preferred embodiments given in the description in this regard.

With regard to the compound according to formula I (cyclo-(Arg-Gly-Asp-DPhe-NMeVal)), the following kinds of writing the name are preferably to be regarded as equivalent:

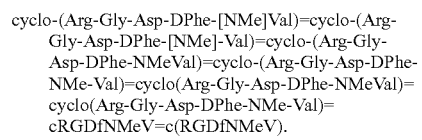

cyclo-(Arg-Gly-Asp-DPhe-[NMe]Val)=cyclo-(Arg-Gly-Asp-DPhe-[NMe]-Val)=cyclo-(Arg-Gly-Asp-DPhe-NMeVal)=cyclo-(Arg-Gly-Asp-DPhe-NMe-Val)=cyclo(Arg-Gly-Asp-DPhe-NMeVal)=cyclo(Arg-Gly-Asp-DPhe-NMe-Val)=cRGDfNMeV=c(RGDfNMeV).

Preferably, cyclo-(Arg-Gly-Asp-DPhe-NMeVal) is also referred to as Cilengitide, which is the INN (International Non-propriety Name) of said compound.

Cyclo-(Arg-Gly-Asp-DPhe-NMeVal) is preferably employed herein as a pharmaceutically acceptable salt, more preferably the pharmacologically acceptable hydrochloride salt, and especially preferably employed as the inner (or internal) salt, which is the compound cyclo-(Arg-Gly-Asp-DPhe-NMeVal) as such.

If not indicated otherwise, a reference to the compound of formula I preferably means a reference to the compound cyclo-(Arg-Gly-Asp-DPhe-NMe-Val) as such, which is preferably the inner salt of said compound. Accordingly, if not indicated otherwise, cyclo-(Arg-Gly-Asp-DPhe-NMe-Val) is preferably also meant to be the inner salt of cyclo-(Arg-Gly-Asp-DPhe-NMe-Val).

Especially preferred according to the invention are subjects as described herein, wherein the characteristics of two or more preferred, more preferred and/or especially preferred embodiments, aspects and/or subjects are combined into one embodiment, aspect and/or subject.

The term "about" as used herein with respect to numbers, figures, ranges and/or amounts is preferably meant to mean "circa" and/or "approximately". The meaning of those terms is well known in the art and preferably includes a variance, deviation and/or variability of the respective number, figure, range and/or amount of plus/minus 15% and especially of plus/minus 10%.

The invention is explained in greater detail below by means of examples. The invention can be carried out throughout the range claimed and is not restricted to the examples given here.

Moreover, the following examples are given in order to assist the skilled artisan to better understand the present invention by way of examplification. The examples are not intended to limit the scope of protection conferred by the claims. The features, properties and advantages exemplified for the compounds, compositions, methods and/or uses defined in the examples may be assigned to other compounds, compositions, methods and/or uses not specifically described and/or defined in the examples, but falling under the scope of what is defined in the claims.

Preferably, the features, properties and advantages exemplified for the compounds, compositions, methods and/or uses defined in the examples and/or claims may be assigned to other compounds, compositions, methods and/or uses not specifically described and/or defined in the examples and/or claims, but falling under the scope of what is defined in the specification and/or the claims.

EXPERIMENTAL

Analytic Methods
IR-Spectroscopy:
FT-IR spectra are preferably obtained on a Bruker Vector 22 spectrometer at room temperature. Therefore standard techniques as described in the European Pharmacopeia 6th Edition chapter 2.02.24 are preferably used. FT-IR spectra are preferably obtained using a KBr pellet as sample preparation technique. Therefore approximately 3 mg of the sample are grinded, mixed with KBr and consequently the mixture is grinded in a mortar. A spectral resolution of 2 cm–1 and 32 Scans are chosen for acquisition of the spectra. FT-IR spectra are preferably base-line corrected using Bruker OPUS software.
Raman-Spectroscopy:
FT-Raman spectra are preferably obtained on a Bruker RFS100 spectrometer equipped with a NdYAG laser (wavelength 1064 nm) at room temperature. Therefore standard techniques as described in the European Pharmacopeia 6th Edition chapter 2.02.48 are preferably used. FT-Raman spectra are preferably obtained using a Aluminium-cups as sample holder. About 5 mg of the samples are stuffed mechanically into the sample holders. A spectral resolution of 1 cm$^{-1}$ or 2 cm$^{-1}$, 500 Scans and a laser power of 500 mW are preferably chosen for acquisition of the Raman-spectra.
TG or TGA:
TG measurements are preferably carried out on a Mettler Toledo TG 851. Measurements are preferably realised by standard techniques as described in the European Pharmacopeia 6th Edition chapter 2.02.34. About 10-20 mg of the respective samples are preferably prepared in Aluminium 100 µL pans without lids. Measurements are preferably carried out in nitrogen atmosphere (50 mL/min) with a heating rate of 5 K/min.

DSC:
DSC measurements are preferably carried out on a Mettler Toledo DSC 821. Measurements are preferably realised by standard techniques as described in the European Pharmacopeia 6th Edition chapter 2.02.34. About 2-10 mg of the respective samples are preferably prepared in Aluminium 40 µL pans with pierced lids. Measurements are preferably carried out in nitrogen atmosphere (50 mL/min) with a heating rate of 5 K/min.
XRD:
Powder X-Ray Diffraction patterns are preferably obtained on a Stoe StadiP 611 KL equipped with a linear PSD detector at room temperature, preferably by standard techniques as described in the European Pharmacopeia 6th Edition chapter 2.9.33. Therefore Cu—Kα1 or Co—Kα1 radiation with a wavelength of 1.5406 Å respectively 1.7889 Å is preferably used. About 30 mg of the samples are preferably prepared in a capillary. Scans are preferably carried out from 5° to 72° with a step size of 0.02° and an integration time of 150 s.
DVS:
Dynamic Vapor Sorption measurements are preferably obtained on a SMS DVS Intrinsic system. The results are preferably obtained by standard techniques as described by Rolf Hilfiker "Polymorphism in the Pharmaceutical Industry" Wiley-VCH Weinheim 2006 (Chapter 9: Water Vapour Sorption, and references therein.) Approx. 2-10 mg of samples are preferably weighed into an Aluminium 100 µL pan and placed in the sample incubator of the DVS instrument with microbalance. A nitrogen overall flow rate of 200 mL/min (combined dry and humid stream) is preferably used for humidifcation. Water vapor sorption isotherms are preferably acquired at 25° C. in the range 0% relative humidity to 98% relative humidity mostly with 10% relative humidity steps. For all relative humidity steps, an equilibrium condition of dm/dt≤0.0005 wt %/min are preferably used, with a minimum relative humidity step time of 10 minutes and a maximum relative humidity step time of 360 minutes which is preferably used as a timeout if the dm/dt criteria mentioned above is not been reached.

Example A

Crystallization of the Inner Salt from the Hydrochloride 1.25 g of cyclo-(Arg-Gly-Asp-DPhe-NMeVal)×HCl are dissolved in 10 ml water. By use of conc. aqueous ammonia pH is adjusted to ~6.8. After standing over night at 4 C, crystals appear, which are separated by filtration, washed with ice-cold water, and dried on air. Mother liquor is concentrated to yield additional crystalline product.

Example B

Crystallization of the Inner Salt from the Trifluoroacetate 1.41 g cyclo-(Arg-Gly-Asp-DPhe-NMeVal)×TFA are dissolved in 10 ml water. By use of conc. aqueous ammonia pH is adjusted to ~6.8. After standing over night at ambient temperature, crystals appear, which are separated by filtration, washed with ice-cold water, and dried on air. Mother liquor is concentrated to yield addition crystalline product.

Example C

Chromatographic Production of the Inner Salt 5.04 g cyclo-(Arg-Gly-Asp-DPhe-NMeVal)×TFA are dissolved in 100 ml water and pH adjusted to ~7.0 with 25%

NH3 aq. The solution is infused with aid of pump A onto a 2-pump gradient system RP-HPLC column (Lichrosorb RP8 (10 um) 50×250 mm). First, column is eluted with water, second, chromatographic purification of compound is by elution with a gradient of 15-25% 2-propanol in water at 20 ml/min in 2 hrs. Detection is at 215/254 nm. Fractions are collected and pooled. During evaporation of 2-propanol from pool crystalline inner salt cyclo-(Arg-Gly-Asp-DPhe-NMe-Val) precipitates and is collected by filtration. Mother liquor is concentrated to yield additional crystalline product.

Example D

Production of Crystals of the Inner Salt from a Co-Solvent Mixture 1 g cyclo-(Arg-Gly-Asp-DPhe-NMeVal) is dissolved in 20 ml water/2-propanol 8:2 vol at 40° C. After 2 days at RT (25° C.) crystalline compound h as precipitated.

Example E

X-Ray Structure Determination of Inner Salt

A crystal from crystalline form S3 is selected for X-ray analysis. Correct covalent structure of the peptide and conformation of the compound in crystalline solid state shows a tetrahydrate is present with 4 molecules according to formula I per unit cell.

| | |
|---|---|
| mol formula | $C_{27}H_{40}N_8O_7 \times 4\,H_2O$ |
| mol weight | 661.25 g/mol |
| crystal size | $(0.65 \times 0.45 \times 0.08)\,mm^3$ |
| temperature | 298 K |
| diffractometer | Nonius - CAD4 |
| rays | Mo Kα |
| wavelength | 0.71093 Å |
| monochrome | graphit |
| crystal | orthorhombic |
| spacegroup | $P\,2_1\,2_1\,2_1$ |
| lattice | a    9.460(2) Å |
| | b   13.853(3) Å |
| | c   25.910(6) Å |
| | $\alpha = \beta = \gamma = 90°$ |
| number of molecules of the compound of formula I per unit cell | 4 |

Example F

X-Ray Structure Determination of the Anhydrate

A crystal from crystalline form A1 is selected for X-ray analysis. Correct covalent structure of the peptide and conformation of the compound in crystalline solid state shows an anhydrate is present with 4 molecules according to formula I per unit cell.

| | |
|---|---|
| mol formula | $C_{27}H_{40}N_8O_7$ |
| mol weight | 588.67 g/mol |
| crystal size | $(0.30 \times 0.24 \times 0.24)\,mm^3$ |
| temperature | 298 K |
| diffractometer | XCalibur - Oxford Diffration |
| rays | Mo Kα |
| wavelength | 0.71093 Å |
| monochrome | graphit |
| crystal | orthorhombic |
| spacegroup | $P\,2_1\,2_1\,2_1$ |
| lattice | a    9.7944(5) Å |
| | b   15.3877(7) Å |
| | c   19.5090(2) Å |
| | $\alpha = \beta = \gamma = 90°$ |
| number of molecules of the compound of formula I per unit cell | 4 |

Example G

X-Ray Structure Determination of the Dihydrate-Monoethanolate

A crystal from crystalline representing one specific example of form S2 is selected for X-ray analysis. Correct covalent structure of the peptide and conformation of the compound in crystalline solid state shows a dihydrate-monoethanolate is present with 4 molecules according to formula I per unit cell.

| | |
|---|---|
| mol formula | $C_{27}H_{40}N_8O_7 \times C_2H_5OH \times 2H_2O$ |
| mol weight | 669.75 g/mol |
| crystal size | $(0.24 \times 0.16 \times 0.04)\,mm^3$ |
| temperature | 298 K |
| diffractometer | XCalibur - Oxford Diffration |
| rays | Mo Kα |
| wavelength | 0.71093 Å |
| monochrome | graphit |
| crystal | orthorhombic |
| spacegroup | $P\,2_1\,2_1\,2_1$ |
| lattice | a    9.3212(4) Å |
| | b   13.7377(7) Å |
| | c   26.337(2) Å |
| | $\alpha = \beta = \gamma = 90°$ |
| number of molecules of the compound of formula I per unit cell | 4 |

Example H

Manufacture of Crystalline Form H1

Crystalline form H1 is obtained according to the following procedure: Crystalline form S2 is dissolved in 0.9% saline until a clear solution with a concentration of 15 mg/mL of the compound of formula I is obtained. The solution is stored at +5° C. under continuous shaking for 4 to 9 weeks, whereby small rodlike-shaped crystals precipitate. Single crystal X-ray diffraction of the thus obtained crystals prove to be crystalline form H1.

Example I

X-Ray Structure Determination of Crystalline Form H1

A crystal from crystalline form H1 is selected for X-ray analysis. Correct covalent structure of the peptide and conformation of the product in crystalline solid state shows a heptahydrate has formed with 4 cyclopeptides per crystal unit.

| | |
|---|---|
| mol formula | $C_{27}H_{40}N_8O_7 \times 7H_2O$ |
| mol weight | 714.81 |

-continued

| | |
|---|---|
| crystal size | (0.50 × 0.24 × 0.20)mm³ |
| temp | 298 K |
| diffractometer | XCalibur - Oxford Diffration |
| rays | Mo Kα |
| length | 0.71093 Å |
| monochrome | graphit |
| crystal group | orthorhombic |
| | P $2_1 2_1 2_1$ |
| lattice | a  8.1349(3) Å |
| | b  12.9357(4) Å |
| | c  35.435(10) Å |
| | α = β = γ = 90° |
| mols of the compound of formula I per unit cell | 4 |

1. Procedure to Obtain Pseudopolymorphic Forms by Stirring in Methanol/Water and Ethanol/Water Mixtures a) Crystalline tetrasolvates according to the invention and especially crystalline forms S1 and S2, can be obtained by slurry conversion from form A1 in a Methanol/Water mixture (70 v %:30 v %) at 25° C. for 2 days stirring time and Ethanol/Water mixture (60 v %:40 v %) at 25° C. for 18 days stirring time, respectively. General procedure:

Approx. 500 mg of form A1 of Cilengitide are dispersed in 5 ml solvent at room temperature. The dispersion is stirred for the mentioned time by a magnetic stirrer and finally filtered.

b) Additionally, crystalline tetrasolvates according invention and especially crystalline forms S1 and S2 can be manufactured by competitive slurry conversion experiments with a mixture of a pseudopolymorphic form (for example S1, S2, S3 or mixtures of these) with form A1 (1:1) in Water/Methanol and Water/Ethanol mixtures with different alcohol contents at different temperatures, respectively.

General Procedure:

Approx. 20 mg of a pseudopolymorphic form (for example S1, S2, S3 or mixtures of these) and 20 mg of form A1 of Cilengitide are dispersed in 300 µl Water/alcohol mixture at 0° C. or room temperature (25° C.). The dispersion is stirred for 24 h and additionally for 3 weeks at RT (25° C.) (long-term experiment) by a magnetic stirrer and finally filtered In the following table the conditions for the experiments leading to the respective tetrasolvate according to the invention are listed:

i) S1:

| solvent in the mixture with Water | 0° C. for 1 day | RT for 1 day | RT for 3 weeks |
|---|---|---|---|
| Methanol | 40-100 v % | 60-100 v % | 60-100 v % |
| Water | ad. 100 v % | ad. 100 v % | ad. 100 v % | ii) S2:

| solvent in the mixture with Water | 0° C. for 1 day | RT for 1 day | RT for 3 weeks |
|---|---|---|---|
| Ethanol | 20-80 v % | 40-80 v % | 40-70 v % |
| Water | ad. 100 v % | ad. 100 v % | ad. 100 v % | c) In contrast thereto, under the following conditions, none of the pseudopolymorphic forms could be obtained, but essentially pure anhydrate/ansolvate A1 is formed instead.

Approx. 20 mg of a pseudopolymorphic form (for example S1, S2, S3 or mixtures of these) and 20 mg of form A1 of Cilengitide are dispersed in 300 µl Water/alcohol mixture at 50° C. The dispersion is stirred for 24 h by a magnetic stirrer and finally filtered.

In the following table the conditions for the experiments leading to form A1 are listed.

| solvent in the mixture with Water | 50° C. for 1 day | solvent in the mixture with Water | 50° C. for 1 day |
|---|---|---|---|
| Methanol | 90-100 v % | Ethanol | 90-100 v % |
| Water | ad. 100 v % | Water | ad. 100 v % |

Water "ad. 100 v %" preferably means that water is added to the before specified amount of solvent other than water (in volume percent (v %)) in an amount to make up for 100 v % of the respective solvent/water mixture.

2. Procedure to Obtain Form S1 by Conditioning Experiments Under Methanol Atmosphere in an Desiccator Approx. 1 g of a pseudopolymorphic form (for example S2, S3 or mixtures of these) are dried in an dessicator above silica gel. Then the material is stored in an desiccator with 100% Methanol vapour atmosphere for 5 days.

3. Procedure to Obtain Form S2 by Conditioning Experiments Under Ethanol Atmosphere in an Desiccator Approx. 1 g of a pseudopolymorphic form (for example S3, S1, or mixtures of these) are dried in an dessicator above silica gel. Then the material is stored in an desiccator with 100% Ethanol vapour atmosphere for 5 days.

4. Procedure to Convert A1/S3 Polymorphic Mixtures to S2 by Stirring in Ethano/Water Mixtures Cilengitide (mixture of polymorph A1 and S3, 275.5 g) is suspended in a mixture of deionized water (700 ml) and ethanol (700 ml). The suspension is stirred at room temperature for 24 h and then cooled to 5° C. The product is isolated by succion filtration and washed with cold ethanol. Drying under vacuum for 72 h at 60° C. yields 270 g of Cilengiti de (crystal form S2), 3.6% EtOH, HPLC purity: 99.9%).

5. Manufacture of Crystalline Form A1 by Slurry Conversion

Form A1 of Cilengitide can be obtained by slurry conversion from pseudopolymorphic forms (for example S1, S2, S3 or mixtures of these) in Water at 25° C. An increased temperature (50° C.) accelerates the conversion to form A1.

Approx. 10 g of a pseudopolymorphic form (for example S1, S2, S3 or mixtures of these) of Cilengitide are dispersed in 50 ml deionised water at room temperature. The dispersion is stirred for 24 h by a magnetic stirrer and finally filtered.

6. Manufacture of Crystalline Form A1 by Competitive Slurry Conversion

Also the pure form A1 can be manufactured by competitive slurry conversion experiments with a mixture of a pseudopolymorphic form (for example S1, S2, S3 or mixtures of these) and A1 (1:1) in Acetone, Acetonitrile, Isopropanol, physiological NaCl solution, Phosphate buffer (pH 7.4) and 1:1 (v:v) mixtures of Acetone, Acetonitrile, Isopropanol with Water at RT (25° C.).

Approx. 20 mg of a pseudopolymorphic form (for example S1, S2, S3 or mixtures of these) and 20 mg of form A1 of Cilengitide are dispersed in 200-700 µl solvent at room temperature. The dispersion is stirred for 5 days and additionally 26 days (long-term experiment) at RT (25° C.) by a magnetic stirrer and finally filtered.

7. Competitive Slurry Conversion

Additionally form A1 can be manufactured by competitive slurry conversion experiments with a mixture of a pseudopolymorphic form (for example S1, S2, S3 or mixtures of these) and form A1 (1:1) in Water/Methanol and Water/Ethanol mixtures with different alcohol contents at different temperatures. In the following table the conditions for the experiments leading to the pure form A1 are listed.

| solvent in the mixture with Water | 0° C. for 1 day | RT for 1 day | RT for 3 weeks | 50° C. for 1 day |
|---|---|---|---|---|
| Methanol | 0 v % | 0-50 v % | 0-40 v % | 0-70 v % |
| water | 100 v % | ad. 100 v % | ad. 100 v % | ad. 100 v % |
| Ethanol | 0-10 v % | 0-30 v % | 0-20 v % | 0-80 v % |
| water | ad. 100 v % | ad. 100 v % | ad. 100 v % | ad. 100 v % |

Approx. 20 mg of a pseudopolymorphic form (for example S1, S2, S3 or mixtures of these) and 20 mg of form A1 of Cilengitide are dispersed in 300 µl Water/alcohol mixture at 0° C., room temperature and 50° C. The dispersion is stirred for 24 h and additionally for 3 weeks at RT (25° C.) (long-term experiment) by a magnetic stirrer and finally filtered.

8. Procedure to Obtain Crystalline Form S2 Including Crystallization from Ethanol/Water Mixtures Cyclo-(Arg-Gly-Asp-DPhe-NMeVal)×TFA×$H_2SO_4$ (400 g) is dissolved in water (1600 ml) at 59° C. The pH is adjusted to pH=6.8 by addition of aqueous ammonia (30%). Methanol (9600 ml) is added to the solution over a period of 3 h. The obtained mixture is cooled to 23° C. within 3 h and stirred at this temperature over night. Then, the mixture is cooled to 5° C. and stirred another 2 h. The precipitated raw product is isolated by sucction filtration and washed with cold methanol. Drying under vacuum for 48 h at 50° C. yields 335 g of Cilengitide (crystalline form S2, HPLC: 99.8%).

The raw material (335 g) is dissolved in water (1507 g) at 58° C. Methanol (8040 ml) is added to the solution over a period of 3 h. The thus formed suspension is then cooled to 23° C. within 3 h and stirred at this temperature over night. The suspension is then cooled to 5° C. and stirred for another 3 h. The product is isolated by sucction filtration and washed with methanol. Drying under vaccuum for 48 h at 60° C. yields 309 g of Cilengitide (crystalline form S1, HPLC: 99.9%, 3.8% MeOH, IC: <0.1% Cl⁻, 0.0007% TFA and 10.3% $SO_4^{2-}$).

The 150 g of the above obtained material are dissolved in water (600 ml) and ethanol (600 ml) at 56° C. The mixture is cooled to 23° C. within 3 h and stirred over night. The mixture (suspension) is cooled to 5° C. and stirred for 2 h at this temperature. The product is isolated by sucction filtration and washed with cold water. Drying under vaccuum for 48 h at 60° C. yields 115.4 g of Cilengitide (crystalline form S2, ≤0.05% Methanol, 5.3% EtOH IC: <0.01% Cl⁻, <0.0011% TFA, 0.34% $SO_4^{2-}$).

9. Manufacture of Crystalline Form A1 by Crystallization from Water

A preferred and very efficient method to obtain A1 is by crystallization from water starting from the raw material of Cilengitide as it evolves from the manufacturing processes:

Raw Cilengitide (300 g, either amorphous material, form S1 (?), form S2, form S3 or mixtures thereof) are dissolved in deionized water (1200 ml) at 58° C. The solution is cooled to 23° C. within 3 h and stirred at this temperature over night. The suspension is then cooled to 5° C. and stirred for 2 h at this temperature. The product is isolated by sucction filtration and washed with cold deionized water. Drying under vaccuum for 48 h at 50° C. yields about 230 g of Cilengitide (crystal form A1, <0.001% TFA, 0.22% $SO_4^{2-}$, 0.06% Ammonium, 99% HPLC purity, 0.027% water).

10. Dynamic Vapour Sorption Experiments of Crystalline Form S3

A SMS DVS I system is used for the dynamic vapour experiments regarding crystalline form S3. The results have been obtained by standard techniques as described in Rolf Hilfiker, 'Polymorphism in the Pharmaceutical Industry', Wiley-VCH. Weinheim 2006 (Chapter 9: Water Vapour Sorption, and references therein). Water Vapour Sorption behaviour shows a loss of water molecules (ca. 9 wt %) within the initial drying step (0% rh). During the water adsorption cycle there is shown an assembly of water molecules (ca. 10 wt %) in the lattice at elevated rh. In the second desorption cycle there is a loss of this amount of water. Water Vapor Sorption isotherm (25° C.) of form S3 is displayed in FIG. 29.

11. Dynamic Vapour Sorption Experiments of Crystalline Form S1

A SMS DVS Intrinsic is used for the dynamic vapour experiments. The results are obtained by standard techniques as described in Rolf Hilfiker, 'Polymorphism in the Pharmaceutical Industry', Wiley-VCH. Weinheim 2006 (Chapter 9: Water Vapour Sorption, and references therein). Water Vapour Sorption behaviour shows a mass loss of approx. 8 wt % in the first desorption cycle, which is slightly lower than the observed Methanol mass gain in the Methanol Vapour Sorption experiment. Upon water vapour adsorption, an assembly of water molecules in the lattice is observed, with a maximum weight gain of approx. 8 wt % at elevated rh. In the second desorption cycle a total mass loss of approx. 9.9 wt % is observed. For a Cilengitide Dihydrate Di-Methanolate, the calculated Methanol content equals 9.3 wt %. Water Vapor Sorption isotherm (25° C.) of form S1 is displayed in FIG. 13.

12. Dynamic Vapour Sorption Experiments of Crystalline Form S2

A SMS DVS Intrinsic is used for the dynamic vapour experiments. The results are obtained by standard techniques as described in Rolf Hilfiker, 'Polymorphism in the Pharmaceutical Industry', Wiley-VCH. Weinheim 2006 (Chapter 9: Water Vapour Sorption, and references therein). Water Vapour Sorption behaviour shows a mass loss of approx. 6.5 wt % in the first desorption cycle, which is lower than the observed Ethanol mass gain in the Ethanol Vapour Sorption experiment. Upon water vapour adsorption, an assembly of water molecules in the lattice is observed, with a maximum weight gain of approx. 6.4 wt % at elevated rh. In the second desorption cycle a total mass loss of approx. 9.2 wt % is observed. For a Cilengitide Dihydrate Di-Ethanolate, the calculated Ethanol content equals 12.5 wt %. Water Vapor Sorption isotherm (25° C.) of form S2 is displayed in FIG. 20.

13. Conditioning Experiments a)

Conditioning of amorphous Cilengitide (abbreviated: Cil; Cilengitide=Cyclo-(Arg-Gly-Asp-DPhe-NMeVal)) under mixed water-ethanol atmospheres—representing different water and alcohol partial pressures (adjusted with different EtOH contents (volume %, v %) in the liquid phase) yielded solvates exhibiting different stoichiometries with up to 4 molecules of water and up to 2 molecules of ethanol per molecule of Cilengitide. Stoichiometries as determined by Karl-Fischer titration (KF) for quantification of water and head space gas-chromatography (HS-GC) (and nuclear magnetic resonance spectroscopy (NMR)) for quantification of ethanol are depicted in Table 3. In the table also points representing stochiometries with more than 4 molecules of water per molecule of Cilengitide are visible. As there is no space for more than 4 molecules of water in the crystal lattice excess amounts of more than 4 molecules of water represent adsorbed moisture.

Also the modifications and the lattice parameters from indexing of the diffractograms are compiled in Table 3.

TABLE 3

| EtOH liquid phase [v %] | H$_2$O KF [wt %] | EtOH HS- GC [wt %] | Σ TG [wt %] | Cil | H$_2$O KF [mol] | EtOH HS- GC [mol] | EtOH NMR | PXRD Form | lattice parameters a [Å] | b [Å] | c [Å] | V [Å$^3$] |
|---|---|---|---|---|---|---|---|---|---|---|---|---|
| 0 | 13.1 | — | 11.7 | 1 | 4.9 | 0.0 | — | S3 | | | | |
| 1 | 14.1 | 0.5 | 13.2 | 1 | 5.4 | 0.1 | — | S3 | 9.5 | 26.0 | 13.9 | 3416 |
| 2.5 | 12.5 | 1.2 | 13.3 | 1 | 4.7 | 0.2 | 0.2 | S3 | 9.5 | 26.1 | 13.9 | 3431 |
| 5 | 11.3 | 2.0 | 12.7 | 1 | 4.2 | 0.3 | — | S3 | 9.5 | 26.1 | 13.9 | 3436 |
| 10 | 9.5 | 3.2 | 12.5 | 1 | 3.6 | 0.5 | 0.5 | S2 | 9.4 | 26.2 | 13.9 | 3438 |
| 20 | 8.4 | 4.3 | 13.0 | 1 | 3.1 | 0.6 | 0.7 | S2 | 9.5 | 26.3 | 13.9 | 3456 |
| 50 | 7.8 | 6.9 | 13.7 | 1 | 3.0 | 1.0 | 1.0 | S2 | 9.4 | 26.4 | 13.9 | 3470 |
| 50 | 6.8 | 6.2 | 12.6 | 1 | 2.5 | 0.9 | — | S2 | 9.5 | 26.5 | 14.0 | 3512 |
| 70 | 6.2 | 6.4 | 12.4 | 1 | 2.3 | 0.9 | — | S2 | 9.4 | 26.4 | 13.9 | 3479 |
| 80 | 5.9 | 6.7 | 12.8 | 1 | 2.2 | 1.0 | — | S2 | 9.5 | 26.5 | 13.9 | 3492 |
| 85 | 4.1 | 9.1 | 12.9 | 1 | 1.5 | 1.3 | — | S2 | | | | |
| 90 | 1.7 | 12.5 | 13.8 | 1 | 0.6 | 1.9 | — | S2 | 9.3 | 26.6 | 14.7 | 3636 |
| 90 | 1.2 | 12.5 | 13.6 | 1 | 0.5 | 1.9 | — | S2 | | | | |
| 95 | 0.4 | 13.1 | 13.7 | 1 | 0.2 | 1.9 | — | S2 | | | | |
| 100 | 0.7 | 13.6 | 14.0 | 1 | 0.3 | 2.0 | 2.0 | S2 | 9.3 | 26.6 | 14.7 | 3648 |

In the Table 3 it is shown that there is a floating transition from the hydrate form S3 into the mixed water-ethanol or waterless ethanol solvate form S2 with increasing ethanol vapour pressure. According to the X-ray-data obtained from the respective solvates, all solvates (including the hydrates) have similar lattice parameters, which only slightly and continuously increase with the assembly of ethanol molecules. b)

Conditioning of amorphous Cilengitide (abbreviated: Cil; Cilengitide=Cyclo-(Arg-Gly-Asp-DPhe-NMeVal) under methanol atmosphere yielded a solvate with 2 molecules methanol per molecule Cilengitide.

| MeOH liquid phase [v %] | H$_2$O KF [wt %] | MeOH HS- GC [wt %] | Σ TG [wt %] | Cil | H$_2$O KF [mol] | EtOH HS- GC [mol] | PXRD Form | lattice parameters a [Å] | b [Å] | c [Å] | V [Å$^3$] |
|---|---|---|---|---|---|---|---|---|---|---|---|
| 100 | 0.3 | 10.0 | 10.4 | 1 | 0.1 | 2.1 | S1 | 9.5 | 25.9 | 13.9 | 3407 |

The invention claimed is:

1. A solid material of a compound according to formula I, cyclo-(Arg-Gly-Asp-DPhe-N-Me-Val)  (I)

wherein said solid material essentially consists of one or more monoclinic and/or orthorhombic crystals of an internal salt of the compound of formula I, the crystals having unit cell dimensions of:

$a=9.5\pm0.5$ Å, $b=23.0\pm5.0$ Å, and $c=14.7\pm1.0$ Å.

2. The solid material according to claim 1, wherein the one or more crystals comprise a solvate.

3. The solid material according to claim 2, wherein the solvate is selected from the group consisting of hydrate, methanolate ethanolate, mixed water-methanol, mixed water-ethanol, and mixed water-methanol-ethanol.

4. The solid material according to claim 1, wherein the one or more crystals comprise no solvate.

5. A process for the manufacture of a solid material according to claim 1, comprising
   a) dissolving or suspending cyclo-(Arg-Gly-Asp-DPhe-NMe-Val) and/or a salt thereof in a polar solvent or solvent mixture,
   b) crystallising the internal salt of cyclo-(Arg-Gly-Asp-DPhe-NMe-Val) in said polar solvent or solvent mixture, and
   c) optionally isolating a solid material according to claim 1, wherein step b) is performed at a pH at about the isoelectric point of the compound of formula I.

6. The process according to claim 5, wherein said step b) is performed at a pH value in the range of 5.5 to 8.

7. The process according to claim 5, wherein said step a), b) and/or c) is performed in a temperature range between −5 and 150° C.

8. The process according to claim 5, wherein the solvent or solvent mixture of step a) and/or b) is selected from the group consisting of water, methanol and ethanol, and mixtures thereof.

9. The process according to claim 5, wherein the solvent or solvent mixture of step a) and/or b) comprises
   i) 5 to 90% by weight of at least one alcohol, selected from the group consisting of methanol and ethanol, and
   ii) 10 to 95% by weight of water.

10. The process according to claim 5, wherein the solvent of step a) and/or b) essentially consists of water, methanol and ethanol.

11. The process according to claim 5, wherein step a) is performed at a temperature above +60° C.

12. The process of claim 5, wherein the polar solvent or solvent mixture comprises a polar aprotic solvent.

13. A method for treating a disorder, comprising administering to a patient the solid material according to claim 1.

14. The method according to claim 13, wherein the disorder is cancer.

15. The method of claim 14, wherein the cancer is selected from the group consisting of brain, lung, head and neck, breast and prostate, and metastases thereof.

\* \* \* \* \*